US010172880B2

(12) United States Patent
Osborn et al.

(10) Patent No.: US 10,172,880 B2
(45) Date of Patent: Jan. 8, 2019

(54) TALEN-BASED GENE CORRECTION

(71) Applicant: Regents of the University of Minnesota, Minneapolis, MN (US)

(72) Inventors: Mark Osborn, Minneapolis, MN (US); Jakub Tolar, Minneapolis, MN (US); Bruce Robert Blazar, Golden Valley, MN (US); Daniel Voytas, Falcon Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 237 days.

(21) Appl. No.: 15/182,773

(22) Filed: Jun. 15, 2016

(65) Prior Publication Data

US 2016/0367588 A1 Dec. 22, 2016

Related U.S. Application Data

(62) Division of application No. 14/193,037, filed on Feb. 28, 2014, now Pat. No. 9,393,257.

(60) Provisional application No. 61/771,735, filed on Mar. 1, 2013.

(51) Int. Cl.
*A61K 31/713* (2006.01)
*A61K 31/7088* (2006.01)
*C12N 9/16* (2006.01)

(52) U.S. Cl.
CPC ........ *A61K 31/713* (2013.01); *A61K 31/7088* (2013.01); *C12N 9/16* (2013.01)

(58) Field of Classification Search
CPC ..... A61K 31/713; A61K 31/7088; C12N 9/16
See application file for complete search history.

(56) References Cited

U.S. PATENT DOCUMENTS

| 2004/0161817 A1 | 8/2004 | Benton et al. |
| 2011/0145940 A1* | 6/2011 | Voytas .................... C12N 9/22 800/13 |
| 2013/0177960 A1 | 7/2013 | Rebar |

FOREIGN PATENT DOCUMENTS

| WO | 2012033462 A1 | 3/2012 |
| WO | 2012065143 A1 | 5/2012 |

OTHER PUBLICATIONS

Woodley et al. (J Invest Dermatol. 2003; 121:1021-1028). (Year: 2003).*
Japanese Patent Application 2015-560341 Translation of Office Action dated Feb. 6, 2018.
International Search Report and Written Opinion of PCT/US2014/ 019322 dated Jun. 2, 2014.
Muzny, et al., Homo sapiens 3 pac rp4-751E10 complete sequence. Gen Bank direct submission AC005923 (Jan. 8, 2003); retrieved on May 20, 2014). Retrieved from the Internet: http/ww.ncbi.nih.gov/ nuccore/AC005923.
Woodley, et al., Intradermal injection of lentiviral vectors corrects regenerated human dystrophic epidermolysis bullosa skin tissue in vivo. Mol Ther. (Aug. 2004) vol. 10, No. 2, pp. 318-326.
Ning Sun et al, Optimized TAL effector nucleases (TALENs) for use in treatment of sickle cell disease, Molecular Biosystems, vol. 8, No. 4, Jan. 1, 2012 (Jan. 1, 2012), p. 1255, XP055081815.
Osborn Mark et al., Transcription Activator-like Effector Nuclease based Genome Editing for Fanconi Anemia (FA), Human Gene Therapy, Mary Ann Liebert, Inc. Publishers, US, [Online] vol. 23, No. 10, Oct. 1, 2012 (Oct. 1, 2012), p. A109.
Zou Jizhong, et al., "Generation of Integration-Free iPSCs from an an X-CGD Patient's blood Cells as Clinically relevant Target for Gene-Repair Using Designer ZFN or TALEN", Molecular Therapy, Nature Publishing Group, GB, [Online] vol. 20, No. Supplement 1, May 1, 2012 (May 1, 2012), pp. S110-S111.
Ousterout Davied G et al: "Genetic Correction of Dystrophin by Engineered Nucleases", Molecular Therapy, Nature Publishing Group, GB, vol. 20, No. Supplement 1, May 1, 2012 (May 1, 2012), pp. S26-S27.
Turczynski Sandrina et al, "Antisense-mediated exon skipping to reframe transcripts", Jan. 1, 2012 (Jan. 1, 2012), Jan. 1, 2012 (Jan. 1, 2012), Exon Skipping: Methods and Protocols, [Methods in Molecular Biology; ISSN 1940-6029; vol. 867], Humana Pr, New York [U.S.], pp. 221-238.
Valerie Pendaries et al; "siRNA-Mediated Allele-Specific Inhibition of Mutant Type VII Collagen in Dominant Dystrophic Epidermolysis Bullosa", Journal of Investigative Dermatology, Feb. 16, 2012 (Feb. 16, 2012).
J. Keith Joung, et al, "Talens: a widely applicable technology for targeted genome editing", Nat Rev Mol Cell Biol., Nov. 21, 2012 (Nov. 21, 2012), pp. 1-16.
Osborn, et al, TALEN-based Gene Correction for Epidermolysis Bullosa, Molecular therapy vol. 21, No. 6, 1151-1159, Jun. 2013.
Extended Search Report of EP14756449.6.-1401/2961262 PCT/ US2014019322 dated Sep. 13, 2016.
Sun, et al. Mol.BioSyst., 2012, vol. 8,p. 1255-1263.
Ousterout et al. Molecular Therapy, 2012, vol. 20, supplement 1, S26-S27.
Zou et al., Molecular Therapy, 2012, vol. 20, Supplement 1, S110-S111.
Jarviallio et al. Human Mutation, 1997, vol. 10, p. 338-347.
Cernak et al. Nucleic Acids Research, 2011, vol. 39, e82.
Reyon et al. Nature Biotechnology, 2012, vol. 30, p. 460-465, Online Methods.
Doyle, et al., Nucleic Acids Research, 2012, vol. 40, W117-W122.
Miller et al. Nature Biotechnology, 2011, vol. 29, p. 143-148, Online Methods.
Mussolino et al, Nucleic Acids Research, 2011, vol. 39, p. 9283-9293.

* cited by examiner

*Primary Examiner* — Scott Long
(74) *Attorney, Agent, or Firm* — Caesar Rivise, PC

(57) ABSTRACT

The invention is directed to transcription activator-like effector nuclease (TALEN)-mediated DNA editing of disease-causing mutations in the context of the human genome and human cells to treat patients with compromised genetic disorders.

6 Claims, 14 Drawing Sheets
Specification includes a Sequence Listing.

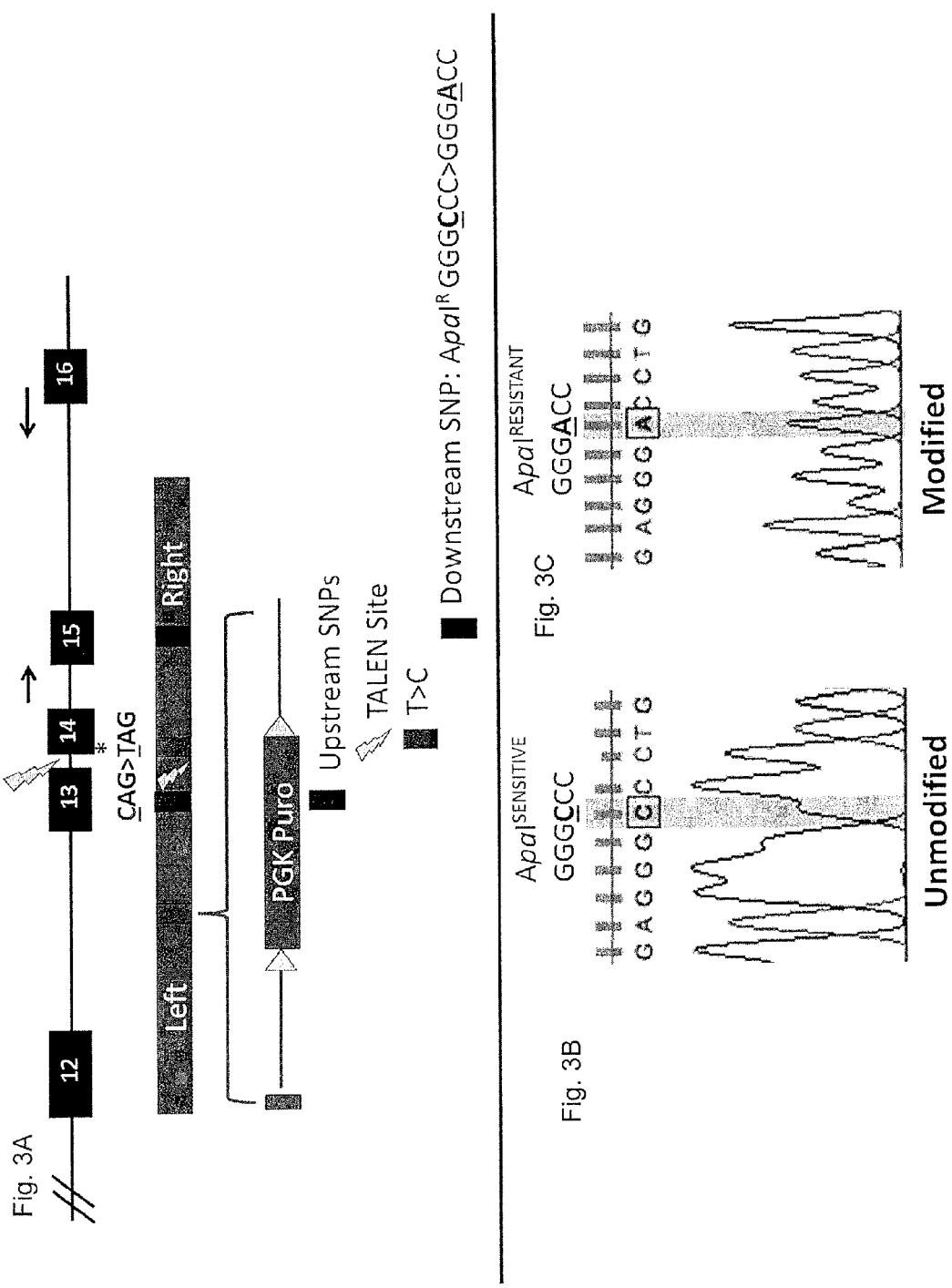

Fig. 5A

↑ Upstream SNPs

∗ ▬ T>C REDB Premature Stop Codon

→ Downstream SNP: ApaI$^R$ GGGCC>GGGACC

Fig. 5B

GGGTGGAGAGAACCCTGGTGCTTCCTGGAGCCAGACGGCATTGGACTTGGATGACGTTC
||||||||||||||||||||||||||||||||||||||||||||||||||||||||||
GGGTGGAGAGAACCCTGGTGCTTCCTGGAGCCAGACGGCATTGGACTTGGATGACGTTC
←
←
←

Fig. 5C

ACTCCACTTGCTGTTCCAGGCTGCGGGGTTGTGGTGTCAGATGCAACGCGAGTGAGGGTG
||||||||||||||||||||||||||||||||||||||||||||||||||||||||||||
ACTCCACTTGCTGTTCCAGGCTGCGGGGTTGTGGTGTCAGATGCAACGTGAGTGAGGGTG
                                                ∗      ▬

Fig. 5D

GTGGCTGTGTCGGTACTGCGAGGCAGAGAGGAGGACCT
|||||||||||||||||||||||||||||||||||||
GTGGCTGTGTCGGTACTGCGAGGCAGAGAGGAGGGCCCT
                                  →

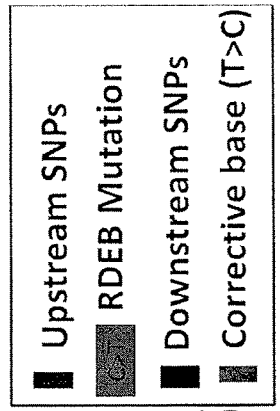
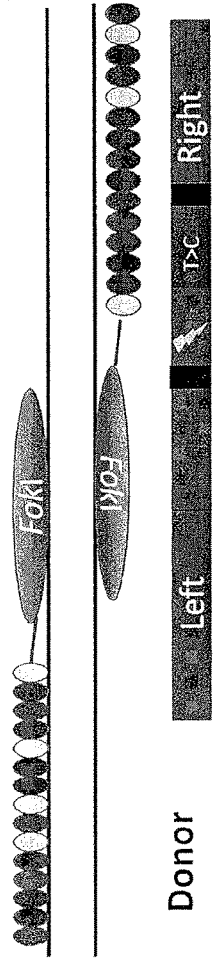
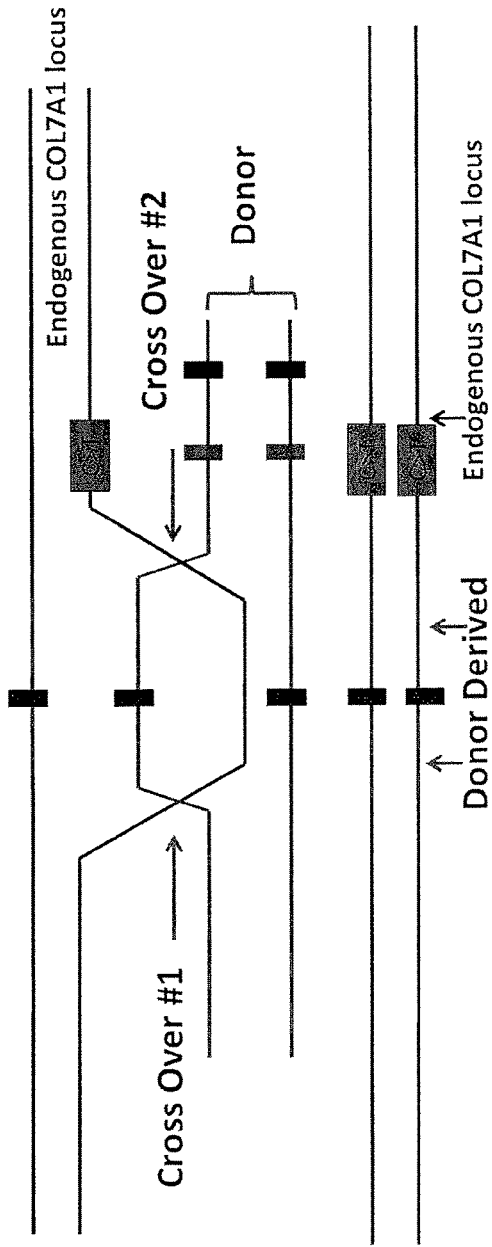
Fig. 6A
Fig. 6B
Fig. 6C
Fig. 6D

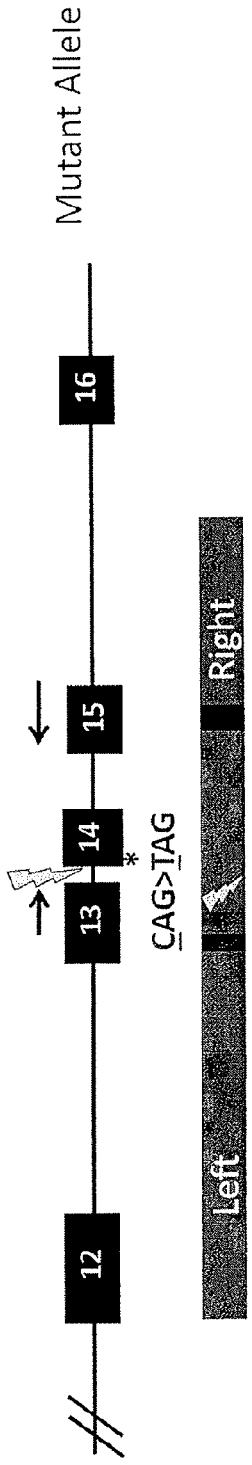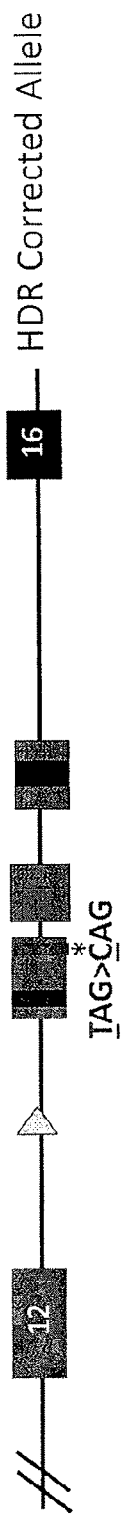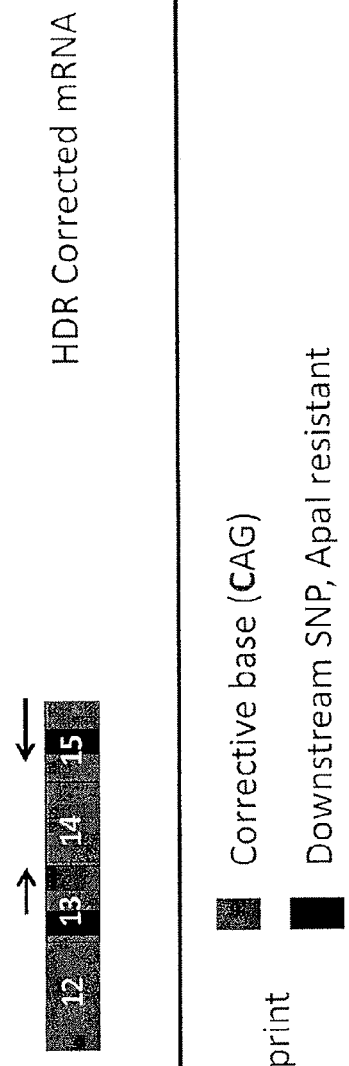
Fig. 7A
Fig. 7B
Fig. 7C

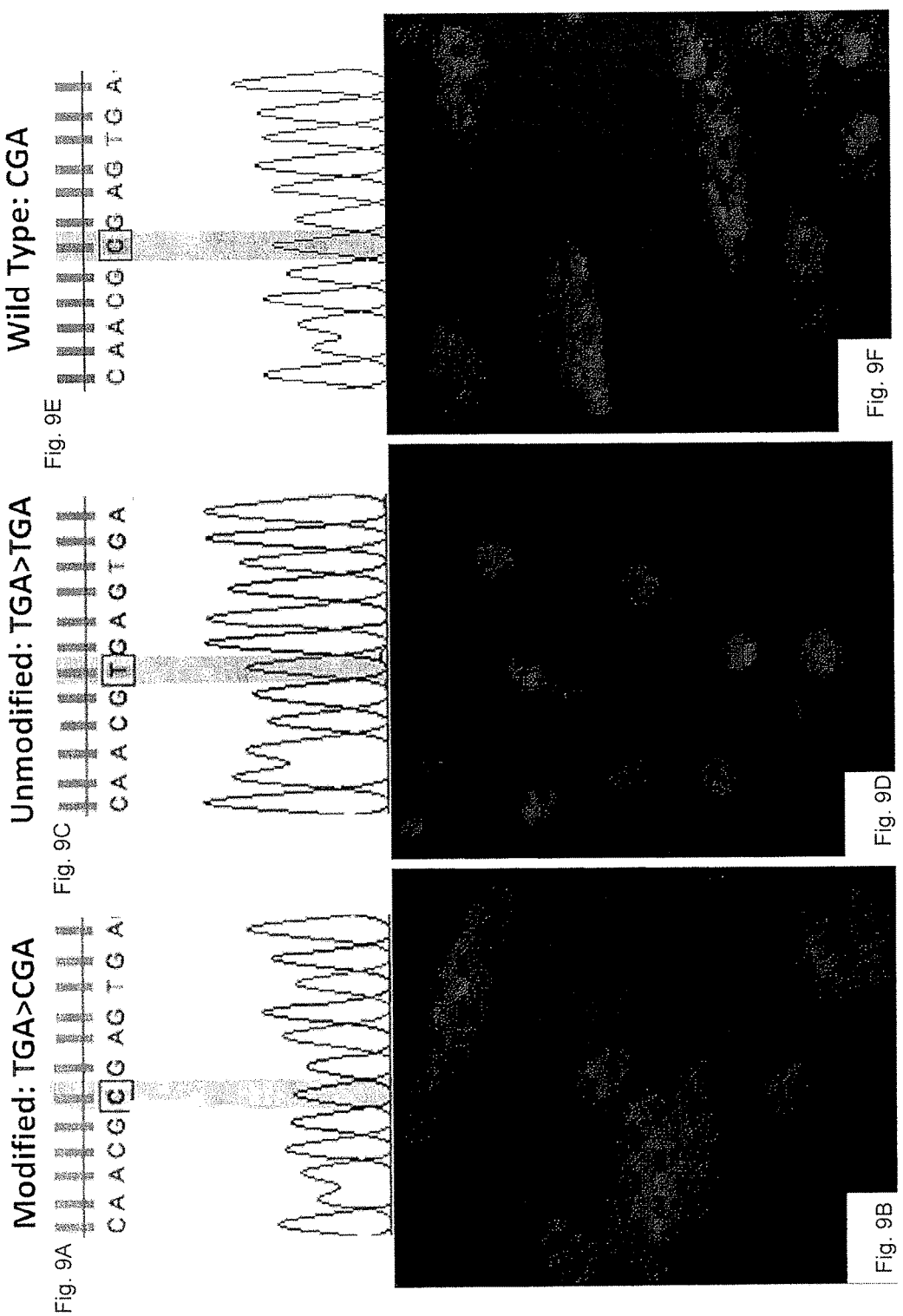

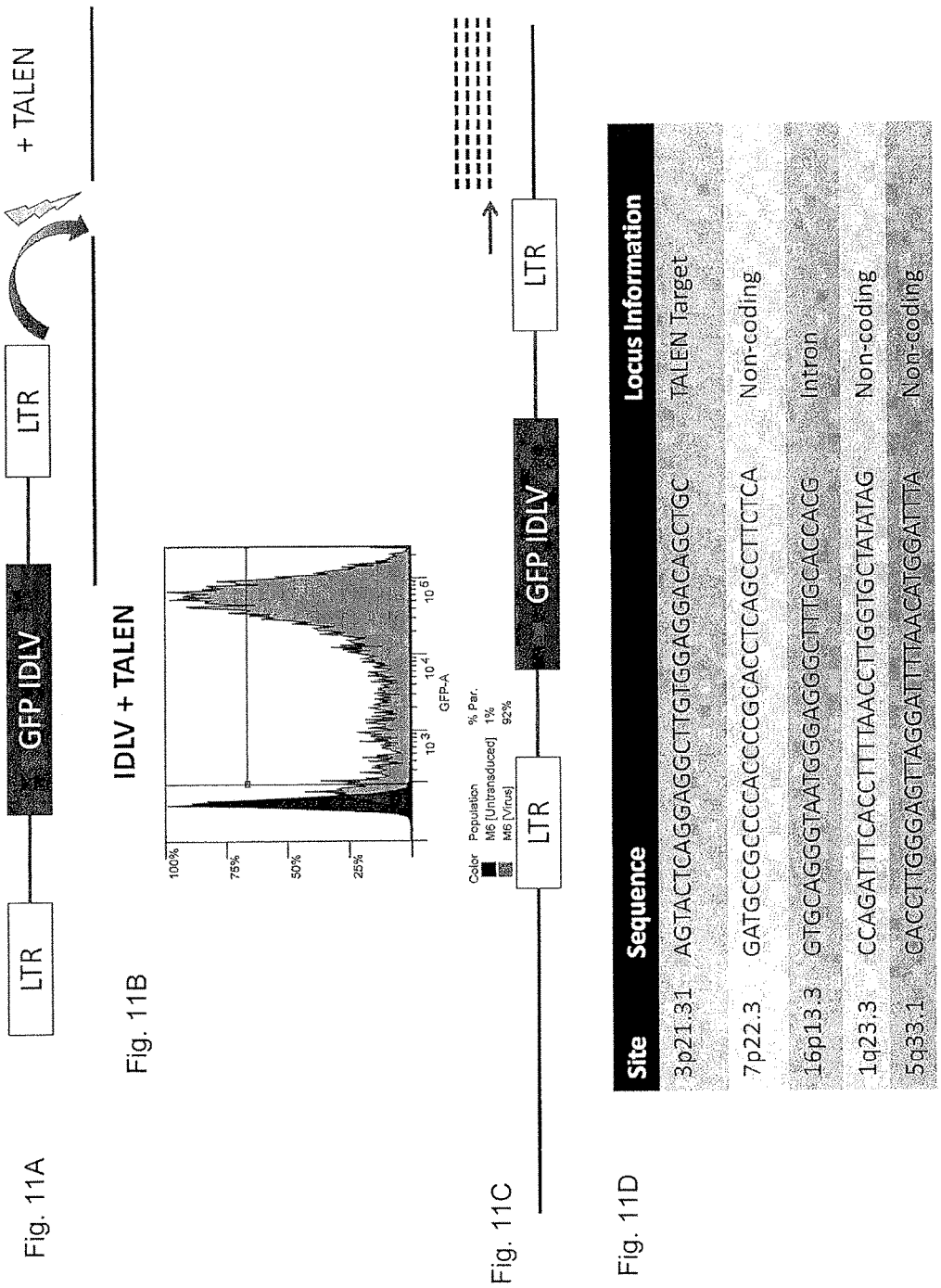

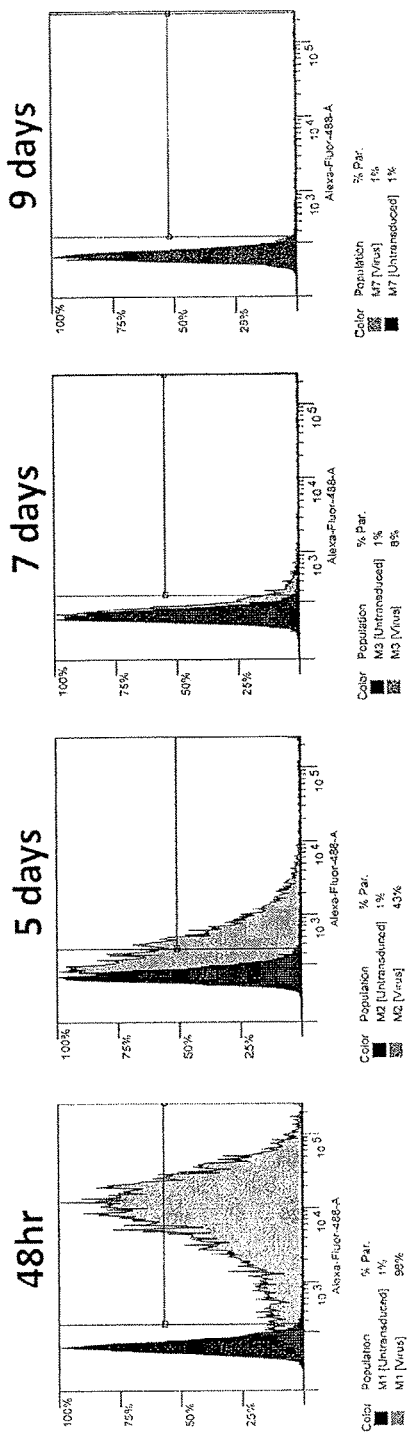
Fig. 12A
Fig. 12B

TALEN-BASED GENE CORRECTION

This application is a divisional of application Ser. No. 14/193,037 filed on Feb. 28, 2014 which claims benefit of U.S. Provisional Patent Application No. 61/771,735, filed Mar. 1, 2013, the entirety of which is incorporated herein.

STATEMENT OF GOVERNMENT SUPPORT

This invention was made with government support under GM098861 and AR063070 awarded by the National Institutes of Health. The government has certain rights in the invention.

SEQUENCE LISTING

The instant application contains a sequence listing which has been submitted in ascii format via efs-web and is hereby incorporated by reference in its entirety. Said ascii copy, created on Feb. 27, 2014, is named J110020004_st25.txt and is 74,494 byte in size.

BACKGROUND OF THE INVENTION

Epidermolysis bullosa (EB) is a group of genetic conditions that cause the skin to be very fragile and to blister easily. Blisters and skin erosions form in response to minor injury or friction, such as rubbing or scratching. Recessive dystrophic epidermolysis bullosa (RDEB), the most severe and classical form of the disease, is characterized by extensive blistering and scarring of the skin and mucosal membranes. The COL7A1 mutations associated with RDEB impair the ability of collagen 7 to connect the epidermis and dermis; and subsequent separation of the epidermis and dermis as a result of friction or minor injury causes the severe blistering and extensive scarring of the skin associated with RDEB. People with RDEB exhibit incurable, often fatal skin blistering and are at increased risk for aggressive squamous cell carcinoma1. Gene augmentation therapies are promising, but run the risk of insertional mutagenesis. Current gene therapy tools (e.g., viral-mediated gene-addition) rely on the provision of functional copies of a therapeutic gene that integrate at random or semi-random into the genome. The consequences of the random integration are perturbation of the locus where the cargo lands and potential gene inactivation or dysregulation (off target effects). These can result in life threatening side effects to the patient. It is therefore described herein engineered transcription activator like effector nucleases (TALENs) for precision genome-editing in cells of patients with, for example, RDEB, and other genetic disorders.

All references cited herein are incorporated by reference in their entireties.

SUMMARY OF THE INVENTION

The present invention overcomes the off target effects by providing site specific correction of the mutation. The correction of the mutation may be accomplished by transformation or transfection of a cell. The cell may be selected from the group consisting of a fibroblast, keratinocyte, inducible pluripotent stem cell, hematopoietic stem cell, mesenchymal stem cell, embryonic stem cell, hematopoietic progeny cell, T-cell, B-cell, glial cell, neural cell, neuroglial progenitor cell, neuroglial stem cell, muscle cell, lung cell, pancreatic cell, liver cell and a cell of the reticular endothelial system One embodiment provides a method to treat a genetic disease or disorder caused by a genetic mutation comprising contacting a cell with one or more nucleic acids encoding a TALEN and a nucleic acid donor sequence, wherein TALEN protein is expressed in the cell and induces a site-specific double stranded DNA break in a target gene, wherein the donor sequence is a template for DNA repair resulting in a correction of the genetic mutation and provides correct gene expression, so as to treat the genetic disease or disorder. In one embodiment, the cell is a fibroblast, keratinocyte, inducible pluripotent-, hematopoietic-, mesenchymal-, or embryonic stem cell, hematopoietic progeny cell (such as a T-cell or B-cell), glia and neural cell, neuroglial progenitor and stem cell, muscle cell, lung cell, pancreatic and/or liver cell and/or a cell of the reticular endothelial system. The invention further provides for the use of one or more nucleic acids to treat a genetic disease or disorder caused by a genetic mutation, where said one or more nucleic acids encode a transcription activator like effector nuclease (TALEN) and a nucleic acid donor sequence, wherein when TALEN protein is expressed in a cell and induces a site-specific double stranded DNA break in a target gene, and wherein the donor sequence is a template for DNA repair, results in a correction of the genetic mutation and provides correct gene expression, so as to treat the genetic disease or disorder.

In the one embodiment, the TALEN is a left TALEN and further comprising a right TALEN that cooperates with the left TALEN to make the double strand break in the target gene. In another embodiment, the nucleic acid encoding the TALEN and/or the nucleic acid donor sequence is part of a vector or plasmid. In one embodiment, the TALEN includes a spacer (e.g., the spacer sequence is 12 to 30 nucleotides in length).

In one embodiment, the target gene is a gene with a genetic alteration/mutation. For example, in one embodiment, the target gene is COL7A1 (one with a mutation causing, for example, aberrant expression of the protein).

In one embodiment, the genetic disease is epidermolysis bullosa, osteogenesis imperfecta, dyskeratosis congenital, the mucopolysaccharidoses, muscular dystrophy, cystic fibrosis (CFTR), fanconi anemia, the sphingolipidoses, the lipofuscinoses, adrenoleukodystrophy, severe combined immunodeficiency, sickle-cell anemia or thalassemia.

One embodiment provides a method to treat a genetic disease or disorder caused by a genetic mutation comprising a) introducing into a cell (i) a first nucleic acid encoding a first transcription activator-like (TAL) effector endonuclease monomer, (ii) a second nucleic acid encoding a second TAL effector endonuclease monomer, and (iii) and a donor sequence, wherein each of said first and second TAL effector endonuclease monomers comprises a plurality of TAL effector repeat sequences and a FokI endonuclease domain, wherein each of said plurality of TAL effector repeat sequences comprises a repeat-variable diresidue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences, wherein said donor sequence comprises homology to the target at least at the 5' and 3's ends of the target sequence and the preselected genetic alteration and is a template for DNA repair resulting in a correction of the genetic mutation; and (b) culturing the cell under conditions in which the first and second TAL effector endonuclease monomers are expressed, so as to correct the mutation and restores correct gene expression. Each of the first and second nucleic acids may comprise a spacer (distinct from the spacer sequence). The spacer sequence may be located between the plurality of TAL effector repeat sequences and the FokI endonuclease domain. The spacer sequence may be 12 to 30 nucleotides. In a further embodiment, the invention provides for the use of one or more nucleic acids to treat a genetic disease or disorder caused by a genetic mutation, wherein (i) a first nucleic acid encodes a first transcription activator-like (TAL) effector endonuclease monomer, (ii) a second nucleic acid encodes a second TAL effector endonuclease monomer, and (iii) and a donor sequence, wherein each of said first and second TAL effector endonuclease monomers comprises a plurality of TAL effector repeat sequences and a FokI endonuclease domain, wherein each of said plurality of TAL effector repeat sequences comprises a repeat-variable diresidue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences, wherein said donor sequence comprises homology to the target at least at the 5' and 3's ends of the target sequence and the preselected genetic alteration and is a template for DNA repair resulting in a correction of the genetic mutation; and wherein (b) culturing the cell under conditions in which the first and second TAL effector endonuclease monomers are expressed, so as to correct the mutation and restore correct gene expression.

Another embodiment provides a nucleic acid comprising a donor sequence, wherein the donor sequence is a template for site specific DNA repair resulting in a correction of a genetic mutation, wherein the donor sequence comprises homology to at least the 5' and 3' ends of the target sequence, wherein a portion of the donor sequence comprises a repair sequence to correct the target sequence for use in conjunction with a TALEN protein. In one embodiment, the donor comprises SEQ ID NO:22. In another embodiment, the target is COL7A1 (a gene with a mutation). In one embodiment, the 5' and 3' ends of the donor each have at least 100 bases of sequence identity to the target.

In another embodiment, the nucleic acid comprises SEQ ID NO:29 or 30. One embodiment provides the proteins coded for or expressed by the TALEN nucleic acids.

One embodiment provides a vector or plasmid comprising a donor sequence, wherein the donor sequence is a template for site specific DNA repair resulting in a correction of a genetic mutation, wherein the donor sequence comprises homology to at least the 5' and 3' ends of the target sequence, wherein a portion of the donor sequence comprises a repair sequence to correct the target sequence for use in conjunction with a TALEN protein. In one embodiment, the donor comprises SEQ ID NO:22. In one embodiment, the target is COL7A1 (with a mutation). In one embodiment, the 5' and 3' ends of the donor each have at least 100 bases of sequence identity to the target. One embodiment provides a vector or plasmid comprising one or more of SEQ ID NOs: 22, 31, 28, 29 or 30. Another embodiment provides an isolated host cell comprising one or more of exogenous SEQ ID NOs: 22, 31, 28, 29 or 30 or the proteins expressed from such sequences. Another embodiment provides a transfected cell line comprising SEQ ID NOs: 22, 31, 28, 29 or 30 or the proteins expressed from such sequences.

One embodiment provides a method to treat a genetic disease or disorder caused by a genetic mutation comprising contacting a cell with a nucleic acid encoding a TALEN, wherein the TALEN corrects the mutation and for example, restores correct gene expression, or enhances gene expression. In one embodiment, the cell is a fibroblast. In another embodiment, the TALEN is a left TALEN and further comprising a right TALEN that cooperates with the left TALEN to make a double strand cut in a DNA. In one embodiment, the nucleic acid molecule is a vector. In another embodiment, the nucleic acid molecule is a plasmid. In one embodiment, the TALEN includes a spacer, such as 12 to 30 nucleotides in length. In one embodiment, the genetic disease is epidermolysis bullosa.

Another embodiment provides a method to treat a genetic disease or disorder caused by a genetic mutation comprising a) introducing into a cell (i) a first nucleic acid encoding a first transcription activator-like (TAL) effector endonuclease monomer, and (ii) a second nucleic acid encoding a second TAL effector endonuclease monomer, wherein each of said first and second TAL effector endonuclease monomers comprises a plurality of TAL effector repeat sequences and a FokI endonuclease domain, wherein each of said plurality of TAL effector repeat sequences comprises a repeat-variable di-residue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences; and (b) culturing the cell under conditions in which the first and second TAL effector endonuclease monomers are expressed, so as to correct the mutation and restores correct gene expression.

The invention provides a nucleic acid encoding a TALEN and a nucleic acid donor sequence, wherein when the TALEN protein is expressed in a cell it induces a site-specific double stranded DNA break in a target gene, and further wherein the donor sequence is a template for DNA repair, which results in a correction of the genetic mutation and provides correct gene expression, so as to treat the genetic disease or disorder. The invention provides the nucleic acid, wherein the cell is a fibroblast, keratinocyte, inducible pluripotent-, hematopoietic-, mesenchymal-, or embryonic stem cell, hematopoietic progeny cell (such as a T-cell or B-cell), glia and neural cell, neuroglial progenitor and stem cell, muscle cell, lung cell, pancreatic and/or liver cell and/or a cell of the reticular endothelial system. The invention provides the nucleic acid, wherein the TALEN is a left TALEN and further comprising a right TALEN that cooperates with the left TALEN to make the double strand break in the target gene. The right TALEN may be encoded by the nucleic acid or a second nucleic acid. The left TALEN and the right TALEN may comprise a plurality of TAL effector repeat sequences and an endonuclease domain. Each of the left and right TALENS may comprise a spacer (distinct from the spacer sequence). The spacer sequence may be located between the plurality of TAL effector repeat sequences and the endonuclease domain. The spacer sequence may be encoded by a sequence of 12 to 30 nucleotides. The invention provides the nucleic acid, wherein said nucleic acid encoding the TALEN and/or the nucleic acid donor sequence is part of a vector or plasmid. The invention provides the nucleic acid, wherein the target gene is a gene with a genetic alteration/mutation. The invention provides the nucleic acid, wherein the target gene is COL7A1. The invention provides the nucleic acid, wherein the TALEN includes a spacer. The invention provides the nucleic acid wherein the spacer sequence is 12 to 30 nucleotides in length. The invention provides the nucleic acid, wherein the genetic disease is epidermolysis bullosa, osteogenesis imperfecta, dyskeratosis congenital, the mucopolysaccharidoses, muscular dystrophy, cystic fibrosis (CFTR), fanconi anemia, the sphingolipidoses, the lipofuscinoses, adrenoleukodystrophy, severe combined immunodeficiency, sickle-cell anemia or thalassemia. The invention provides the nucleic acid, where in the genetic disease is epidermolysis bullosa. The invention provides at least one nucleic acid comprising (i) a first nucleic acid encoding a first transcription activator-like (TAL) effector endonuclease monomer, (ii) a second nucleic acid encoding a second TAL effector endonuclease monomer, and (iii) and a donor sequence, wherein each of said first and second TAL effector endonuclease monomers comprises a plurality of TAL effector repeat sequences and a FokI endonuclease domain, wherein each of said plurality of TAL effector repeat sequences comprises a repeat-variable diresidue, wherein said first TAL effector endonuclease monomer comprises the ability to bind to a first half-site sequence of a target DNA within said cell and comprises the ability to cleave said target DNA when said second TAL effector endonuclease monomer is bound to a second half-site sequence of said target DNA, wherein said target DNA comprises said first half-site sequence and said second half-site sequence separated by a spacer sequence, and wherein said first and second half-sites have the same nucleotide sequence or different nucleotide sequences, wherein said donor sequence comprises homology to the target at least at the 5' and 3's ends of the target sequence and the preselected genetic alteration and is a template for DNA repair resulting in a correction of the genetic mutation; and (b) culturing the cell under conditions in which the first and second TAL effector endonuclease monomers are expressed, so as to correct the mutation and restores correct gene expression. The invention provides a protein coded for or expressed by the nucleic acid. The invention provides a vector or plasmid comprising the nucleic acid. The invention provides an isolated host cell comprising the nucleic acid.

The invention provides for the use of the nucleic acids, vectors, host cells, and proteins of the invention to treat a genetic disease or disorder caused by a genetic mutation.

BRIEF DESCRIPTION OF THE DRAWINGS

FIG. 1A COL7A1 target site on chromosome 3 and TALEN array binding. A schematic of human chromosome three and the region in exon 13 that was targeted is shown. Arrows refer to primer sets used for subsequent analyses, and the line with mottled grey box is the donor used in (f). FIG. 1B COL7A1 target site and the core constituents of the nuclease complex. The TALEN is comprised of an N-terminal deletion of 152 residues of *Xanthomonas* TALEs, followed by the repeat domain, and a +63 C-terminal subregion fused to the catalytic domain of the FokI nuclease. (SEQ ID NO: 33; SEQ ID NO: 34) FIG. 1C Repeat Variable Diresidue (RVD) base recognition. The RVDs NN, NI, HD, and NG (that bind guanine, adenine, cytosine, and thymine, respectively) are coded to the corresponding full array in 1b. FIG. 1D Sketch of TALEN-generated (lightning bolt) double-stranded DNA break (DSB) and possible cellular repair mechanisms used for break repair. (SEQ ID NO: 35; SEQ ID NO: 36). FIG. 1E Error-prone non-homologous end-joining assessment by Sanger sequencing of TALEN-treated cells. Limiting cycle PCR was performed, followed by shotgun cloning; 75 clones were sequenced, with 64 showing 100% alignment to the genome database and 11 exhibiting non-homologous end joining (NHEJ)-induced deletions that are represented as dashes. The TALEN left and right target sites are in bold capital letters, and the spacer sequence is in lower-case letters. Total bases deleted are represented at right and signified as "del" followed by numbers of bases lost. FIG. 1F Homology-directed repair (HDR). The single-stranded oligonucleotide donor (ssODN) contained 65 bp of COL7A1 gene homology on the left arm and 101 bp on the right with a short, foreign sequence that serves as a unique primer site (mottled, grey box). Three primer PCR results in amplification with endogenous primer pairs (indicated with arrows labeled i. and iii.). TALEN insertion of the ODN results in a second, smaller PCR product size generated by primer pairs ii. and iii. The number at the bottom of the TALEN-treated cells indicates the rate of HDR determined by densitometry. (SEQ ID NOS: 37 to (SEQ ID NO: 48).

FIGS. 3A-3C. TALEN COL7A1 donor design and homology-directed repair. FIG. 3A COL7A1 locus with mutation indicated by asterisk. Below is the donor, in alignment to its relation with the endogenous locus that is comprised of COL7A1 genomic sequences of a left arm 706 bp long and 100% homologous to the genomic locus. In between the left and right arms, designed so that it would be knocked into the intron between exons 12 and 13, is a floxed PGK puromycin cassette (box, loxp sites indicated by flanking arrows). The right arm was 806 bp long and contained 5 base changes. Four of these were silent point mutation polymorphisms (SPMPs) (referred to as upstream and downstream) that served as markers for identification of HDR-based events; the last was the normalized base that corrects the premature termination codon. The box represents three of the SPMPs that were located within 10 bp of one another. The normal (i.e., mutation reversion) base is denoted by the box and the terminal (downstream) SPMP that removes an ApaI restriction enzyme site is represented by a black box. Lightning bolt indicates the TALEN target site and the PCR primers (black arrows), designed so one was in the donor arm and the other outside it; utilized for analyses as shown. (SEQ ID NO: 49). SPMP detection in RDEB fibroblasts. TALEN treatment and PCR amplification followed by digestion with ApaI and Sanger sequencing shows the FIG. 3B presence of the ApaI-resistant SPMP that is derived from the donor and can only be present following TALEN cutting and homology-directed repair using the exogenous donor as the template, (SEQ ID NO: 50) FIG. 3C the unmodified base (ApaI sensitive) showing that a heterozygous HDR event occurred (SEQ ID NO: 51).

FIG. 4A Sketch of donor with floxed PGK puromycin. Introduction of a Cre-recombinase plasmid into puromycin resistant fibroblasts resulted in removal of the puromycin transgene. FIG. 4B Genomic loxp/COL7A1 junction. PCR was used to demonstrate the presence of a loxP footprint (triangle/sequence below) in the intron between exons 12 and 13 in the RDEB TALEN/donor treated cells. (SEQ ID NO: 52).

FIGS. 5A-5D. Early crossover event sequence analysis. FIG. 5A key for marker sequences introduced into the donor. Arrow=upstream SPMPs, line=the 1837 base causative for RDEB, arrow=downstream SPMPs. (SEQ ID NO: 53). Upstream crossover event. Sanger sequencing showing the incorporation of the upstream SPMPs FIG. 5B the maintenance of the mutation at base 1837 (SEQ ID NO: 54; (SEQ ID NO: 55) FIG. 5C and the absence of the downstream SPMP (SEQ ID NO: 56; (SEQ ID NO: 57) FIG. 5D indicating that HDR occurred from the donor but failed to correct the mutation. Legend has been fixed to include D (SEQ ID NO: 58; (SEQ ID NO: 59).

FIGS. 6A-6D. Sketch of putative early cross over event. FIG. 6A TALEN arrays are shown binding to the target sequence and the donor is shown below. FIG. 6B binding to target site and TALEN dimerization mediate a double stranded DNA break (lightning) and stimulation of HDR using the donor as the repair template. FIG. 6C Theoretical cross-over events. Alignment of the endogenous DNA and the donor results in a cross over event (Cross Over #1) where genetic material is exchanged in a manner where the upstream SPMPs (box) are incorporated while the second crossover (arrow/Cross Over #2) event happens upstream of the corrective base and downstream SPMP. FIG. 6D Resolved genomic sequence containing partial donor sequences (lines and box) with maintenance of the mutated base (box).

FIGS. 7A-7C. Schematic of HDR and normal mRNA production. FIG. 7A Mutated endogenous COL7A1 locus with TALEN target site indicated by lightning. Mutated base is shown and underneath is the donor that results in the FIG. 7B repair of the locus with permanent presence of donor-derived sequences from exon 12 through the intron between exons 15 and 16. FIG. 7C mRNA analysis. The indicated primers amplified a product that contains the corrective base (box and the ApaI SPMP black box) in the same amplicon.

FIGS. 9A-9F. TALEN-mediated gene editing of COL7A1 with HDR and resultant normalized gene and protein expression. FIG. 9A TALEN-corrected cells with conversion of the mutation to wild-type status, (SEQ ID NO: 64) and FIG. 9B restoration of collagen type VII production assessed by immunofluorescence. FIG. 9C Homozygous RDEB premature termination codon cDNA sequencing, (SEQ ID NO: 65) and FIG. 9D absence of type VII collagen protein production. FIG. 9E Sanger sequencing of wild-type COL7A1 locus, (SEQ ID NO: 66) and FIG. 9F type VII collagen expression. Cells were stained simultaneously and confocal microscopy exposure times and instrument setting were identical. Nuclei are stained with DAPI and show as blue.

FIG. 10A Fibroblast clone 1-19 (SEQ ID NO: 67; SEQ ID NO: 68) and FIG. 10B 1-21 showed the presence of the corrected base (line) and the downstream SPMP (arrow). (SEQ ID NO:69; SEQ ID NO: 70).

FIGS. 11A-11D. TALEN integration mapping profile. FIG. 11A Schematic of TALEN-induced DNA break that accepts the GFP cargo, permanently marking the genomic locus. FIG. 11B TALEN and IDLV co-expression in 293 cells resulted in stable GFP cells (flow cytometry analysis performed 6 weeks post TALEN and IDLV delivery). FIG. 11C Schema for linear amplification-mediated PCR. Blue arrow denotes the LAM PCR primer, and the dashed lines represent the products of linear amplification that were subsequently cloned and mapped to determine the TALEN-induced IDLV genomic fusion fragment. FIG. 11D (nr)LAM PCR/PCR identified integrants. LAM PCR sequence recovery and genome database search revealed five sites into which the IDLV integrated. Sequences mapped to the spacer region of the COL7A1 target site and four off-target sites at chromosomes 7, 16, 1, and 5 (none of the latter sequences were derived from a coding exon). (SEQ ID NOs: 71-75).

FIG. 12A-12B. Integrase deficient lentivirus. FIG. 12A sketch of GFP viral cassette that was produced with a defective integrase. FIG. 12B 293 IDLV GFP expression time course in the absence of TALENs over sequential analyses over 9 days showing rapid loss of GFP.

DETAILED DESCRIPTION OF THE INVENTION

Figure 1:
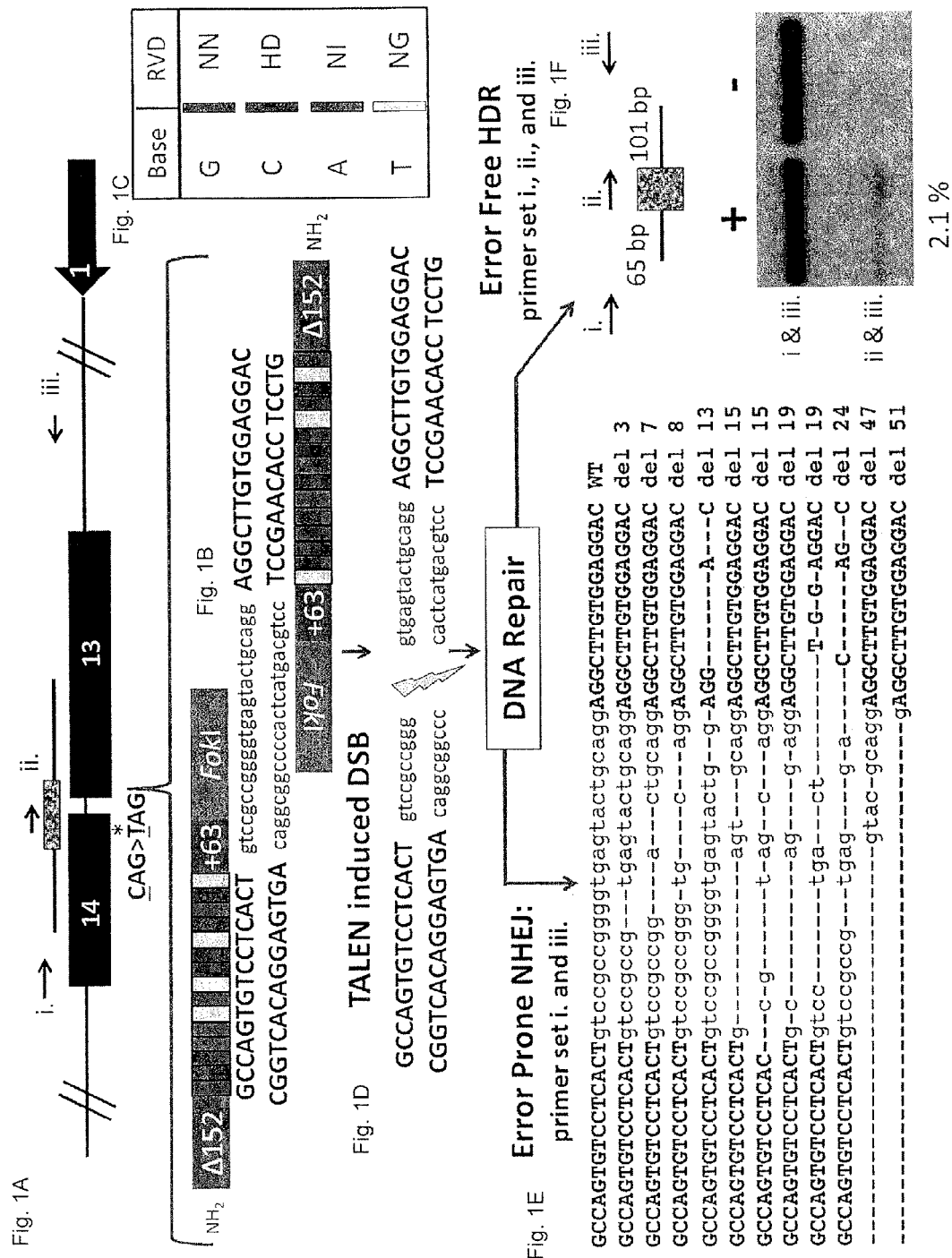
FIGS. 1A-1F. TALEN targeting, nuclease architecture and modification of COL7A1 gene.

The invention is directed to transcription activator-like effector nuclease (TALEN)-mediated DNA editing of disease-causing mutations in the context of the human genome and human cells to treat patients with compromised genetic disorders. This is an advance over previous gene therapy trials/tools that rely on the provision of functional copies of a therapeutic gene that integrate at random or semi-random into the genome. The consequences of the previous gene therapy methods are perturbation of the locus where the cargo lands and potential gene inactivation or dysregulation. These can result in life threatening side effects. The approach described herein maximizes safety and efficacy by employing a tailor made TALEN for, for example, the human genes that corrects the mutation spot alone while preserving the remainder of the genome in pristine condition—in other words, there is no disruption of the remaining genome, thus eliminating the off targets effects associated with the existing technology (e.g., viral-mediated gene-addition). This is a novel approach and is the first personalized gene therapy with TALEN-mediated transgene-free correction of disease causing mutation in cells, for example, human cells. Thus, the technology can be used in cells, such as human cells, such that a loss-of-function mutation can be seamlessly corrected with restoration of normal cellular function. In other embodiments, gene expression can be enhanced.

Definitions

In describing and claiming the invention, the following terminology will be used in accordance with the definitions set forth below. Unless defined otherwise, all technical and scientific terms used herein have the same meaning as commonly understood by one of ordinary skill in the art to which this invention belongs. Any methods and materials similar or equivalent to those described herein can be used in the practice or testing of the present invention. Specific and preferred values listed below for radicals, substituents, and ranges are for illustration only; they do not exclude other defined values or other values within defined ranges for the radicals and substituents.

As used herein, the articles "a" and "an" refer to one or to more than one, i.e., to at least one, of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

The term "isolated" refers to a factor(s), cell or cells which are not associated with one or more factors, cells or one or more cellular components that are associated with the factor(s), cell or cells in vivo.

"Cells" include cells from, or the "subject" is, a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, or orangutan), rat, sheep, goat, cow and bird.

A "control" subject is a subject having the same characteristics as a test subject, such as a similar type of disease, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated.

A "disease" is a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. However, the definitions of "disease" and "disorder" as described above are not meant to supersede the definitions or common usage related to specific addictive diseases or disorders.

A disease, condition, or disorder is "alleviated" if, for example, the severity of a symptom of the disease or disorder, the frequency with which such a symptom is experienced by a patient, or both, are reduced.

As used herein, an "effective amount" means, for example, an amount sufficient to produce a selected effect, such as alleviating symptoms of a disease or disorder.

The term "measuring the level of expression" or "determining the level of expression" as used herein refers to, for example, any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present.

As used herein, the term "pharmaceutically acceptable carrier" includes, for example, any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "pharmaceutically-acceptable salt" refers to, for example, salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

By the term "specifically binds," as used herein, is meant, for example, a molecule which recognizes and binds a specific molecule, but does not substantially recognize or bind other molecules in a sample.

The term "symptom," as used herein, refers to, for example, any morbid phenomenon or departure from the normal in structure, function, or sensation, experienced by the patient and indicative of disease.

As used herein, the term "treating" may include prophylaxis of the specific disease, disorder, or condition, or alleviation of the symptoms associated with a specific disease, disorder or condition and/or preventing or eliminating the symptoms. A "prophylactic" treatment is, for example, a treatment administered to a subject who does not exhibit signs of a disease or exhibits only early signs of the disease for the purpose of decreasing the risk of developing pathology associated with the disease. "Treating" is used interchangeably with "treatment" herein.

A "therapeutic" treatment is, for example, a treatment administered to a subject who exhibits symptoms of pathology for the purpose of diminishing or eliminating those symptoms.

A "therapeutically effective amount" of a compound is, for example, that amount of compound which is sufficient to provide a beneficial effect to the subject to which the compound is administered.

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |

-continued

| Full Name | Three-Letter Code | One-Letter Code |
|---|---|---|
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids may be classified into seven groups on the basis of the side chain R: (1) aliphatic side chains; (2) side chains containing a hydroxyl (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp As used herein, the term "nucleic acid" encompasses RNA as well as single, double and triple stranded DNA and cDNA. Furthermore, the terms, "nucleic acid," "DNA," "RNA" and similar terms also include nucleic acid analogs, i.e. analogs having other than a phosphodiester backbone. For example, the so called "peptide nucleic acids," which are known in the art and have peptide bonds instead of phosphodiester bonds in the backbone, are considered within the scope of the present invention. By "nucleic acid" is also meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using, for example, the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The terms "comprises," "comprising," and the like can have the meaning ascribed to them in U.S. Patent Law and can mean "includes," "including" and the like. As used herein, "including" or "includes" or the like means including, without limitation.

TALENs

Transcription Activator-Like Effector Nucleases (TALENs) are artificial restriction enzymes generated by fusing the TAL effector DNA binding domain to a DNA cleavage domain. These reagents enable efficient, programmable, and specific DNA cleavage and represent powerful tools for genome editing in situ. Transcription activator-like effectors (TALEs) can be quickly engineered to bind practically any DNA sequence. The term TALEN, as used herein, is broad and includes a monomeric TALEN that can cleave double stranded DNA without assistance from another TALEN. The term TALEN is also used to refer to one or both members of a pair of TALENs that are engineered to work together to cleave DNA at the same site. TALENs that work together may be referred to as a left-TALEN and a right-TALEN, which references the handedness of DNA. See U.S. Ser. No. 12/965,590; U.S. Ser. No. 13/426,991 (U.S. Pat. No. 8,450,471); U.S. Ser. No. 13/427,040 (U.S. Pat. No. 8,440,431); U.S. Ser. No. 13/427,137 (U.S. Pat. No. 8,440,432); and U.S. Ser. No. 13/738,381, all of which are incorporated by reference herein in their entirety.

TAL effectors are proteins secreted by *Xanthomonas* bacteria. The DNA binding domain contains a highly conserved 33-34 amino acid sequence with the exception of the 12th and 13th amino acids. These two locations are highly variable (Repeat Variable Diresidue (RVD)) and show a strong correlation with specific nucleotide recognition. This simple relationship between amino acid sequence and DNA recognition has allowed for the engineering of specific DNA binding domains by selecting a combination of repeat segments containing the appropriate RVDs.

The non-specific DNA cleavage domain from the end of the FokI endonuclease can be used to construct hybrid nucleases that are active in a yeast assay. These reagents are also active in plant cells and in animal cells. Initial TALEN studies used the wild-type FokI cleavage domain, but some subsequent TALEN studies also used FokI cleavage domain variants with mutations designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. The number of amino acid residues between the TALEN DNA binding domain and the FokI cleavage domain may be modified by introduction of a spacer (distinct from the spacer sequence) between the plurality of TAL effector repeat sequences and the FokI endonuclease domain. The spacer sequence may be 12 to 30 nucleotides.

The relationship between amino acid sequence and DNA recognition of the TALEN binding domain allows for designable proteins. In this case artificial gene synthesis is problematic because of improper annealing of the repetitive sequence found in the TALE binding domain. One solution to this is to use a publicly available software program (DNAWorks) to calculate oligonucleotides suitable for assembly in a two step PCR; oligonucleotide assembly followed by whole gene amplification. A number of modular assembly schemes for generating engineered TALE constructs have also been reported. Both methods offer a systematic approach to engineering DNA binding domains that is conceptually similar to the modular assembly method for generating zinc finger DNA recognition domains.

Once the TALEN genes have been assembled they are inserted into plasmids; the plasmids are then used to transfect the target cell where the gene products are expressed and enter the nucleus to access the genome. TALENs can be used to edit genomes by inducing double-strand breaks (DSB), which cells respond to with repair mechanisms. In this manner, they can be used to correct mutations in the genome which, for example, cause disease.

Vectors and Nucleic Acids

A variety of nucleic acids may be introduced into cells to obtain expression of a gene. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

Nucleic acid sequences can be operably linked to a regulatory region such as a promoter. Regulatory regions can be from any species. As used herein, operably linked refers to positioning of a regulatory region relative to a nucleic acid sequence in such a way as to permit or facilitate transcription of the target nucleic acid. Any type of promoter can be operably linked to a nucleic acid sequence. Examples of promoters include, without limitation, tissue-specific promoters, constitutive promoters, and promoters responsive or unresponsive to a particular stimulus (e.g., inducible promoters).

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

Nucleic acid constructs can be introduced into cells of any type using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

Therapeutic Uses

TALEN-based gene correction has many clinical and preclinical (e.g., research) applications. For example, TALEN-based gene correction can used to correct genes in which mutations lead to disease. For example, any disease characterized by small base alterations including insertions and deletions such as, but not restricted to, epidermolysis bullosa, osteogenesis imperfecta, dyskeratosis congenital, the mucopolysaccharidoses, muscular dystrophy, cystic fibrosis (CFTR), fanconi anemia, the sphingolipidoses, the lipofuscinoses, adrenoleukodystrophy, severe combined immunodeficiency, sickle-cell anemia, thalassemia, and the like.

In one embodiment, the disease is Epidermolysis Bullosa. Recessive dystrophic epidermolysis bullosa (RDEB) is characterized by a functional deficit of the type VII collagen protein due to gene defects in the type VII collagen (COL7A1) gene. This gene encodes the alpha chain of type VII collagen. The type VII collagen fibril, composed of three identical alpha collagen chains, is restricted to the basement zone beneath stratified squamous epithelia. It functions as an anchoring fibril between the external epithelia and the underlying stroma. Mutations in this gene are associated with all forms of dystrophic epidermolysis bullosa.

COL7A1 is located on the short arm of human chromosome 3, in the chromosomal region denoted 3p21.31 (Ensembl No: ENSG00000114270). The gene is approximately 31,000 base pairs in size and its coding sequence is fragmented into 118 exons, see SEQ ID NO: 32.

COL7A1 is transcribed into an mRNA of 9,287 base pairs (Accession Nos. for human mRNA and protein are NM_000094 and NP_000085, respectively). In the skin, the type VII collagen protein is synthesized by keratinocytes and dermal fibroblasts. The symbol for the orthologous gene in the mouse is Col7a1 (Accession No for Mouse mRNA and protein are NM_00738 and NP_031764, respectively).

People with RDEB exhibit incurable, often fatal skin blistering and are at increased risk for aggressive squamous cell carcinoma[1]. Gene augmentation therapies are promising, but run the risk of insertional mutagenesis. It is therefore described herein engineered transcription activator like effector nucleases (TALENs) for precision genome-editing in cells of patients with RDEB. It is described herein the ability of TALENs to induce site-specific double-stranded DNA breaks (DSB) leading to homology-directed repair (HDR) from an exogenous donor template. This process resulted in COL7A1 gene mutation correction and restoration of normal gene and protein expression. This study provides proof-of-concept for personalized genomic medicine and is the first TALEN-mediated in situ correction of an endogenous human gene in fibroblasts.

Cells to be modified by TALEN-based gene correction can be obtained from the patient or from a donor. The cells can be of any type, such as fibroblast cells, keratinocytes, inducible pluripotent-, hematopoietic-, mesenchymal-, and embryonic stem cells, hematopoietic progeny cells, such as T-cells, B-cells, glia and neurons, neuroglial progenitor and stem cells, muscle cells, lung cells, pancreatic and liver cells and/or cells of the reticular endothelial system). Once modified by TALEN-based gene correction, the cells can be expanded and/or administered to a patient to treat the disease.

Matrices can be used to deliver cells of the present invention to specific anatomic sites, where particular growth factors may or may not be incorporated into the matrix, or encoded on plasmids incorporated into the matrix for uptake by the cells, can be used to direct the growth of the initial cell population. Plasmid DNA encoding cytokines, growth factors, or hormones can be trapped within a polymer gene-activated matrix carrier. The biodegradable polymer is then implanted near the site where treatment is desired.

For the purposes described herein, either autologous, allogeneic or xeongenic cells of the present invention can be administered to a patient by direct injection to a preselected site, systemically, on or around the surface of an acceptable matrix, or in combination with a pharmaceutically acceptable carrier.

Additionally, nucleic acid constructs or proteins can be injected locally or systemically into a subject, with, for example, a pharmaceutically acceptable carrier.

Growth/Expansion of Cells

Cells to be modified by TALEN-based gene correction can be obtained from the patient or from a donor. The cells can be of any type, such as fibroblast cells. Once modified by TALEN-based gene correction, the cells can be expanded and/or administered to a patient to treat the disease.

The cells can be cultured in culture medium that is established in the art and commercially available from the American Type Culture Collection (ATCC), Invitrogen and other companies. Such media include, but are not limited to, Dulbecco's Modified Eagle's Medium (DMEM), DMEM F12 medium, Eagle's Minimum Essential Medium, F-12K medium, Iscove's Modified Dulbecco's Medium, Knockout D-MEM, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are needed for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements (including, but not limited to, KnockOut Serum Replacement (KSR, Invitrogen)), and bovine embryonic fluid. It is understood that sera can be heat-inactivated at 55-65° C. if deemed needed to inactivate components of the complement cascade. Modulation of serum concentrations, or withdrawal of serum from the culture medium can also be used to promote survival of one or more desired cell types. In one embodiment, the cells are cultured in the presence of FBS/serum specific for the species cell type. For example, cells can be isolated and/or expanded with total serum (e.g., FBS) or serum replacement concentrations of about 0.5% to about 5% or greater including about 5% to about 15% or greater, such as about 20%, about 25% or about 30%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution™ (HBSS), Earle's Salt Solution™, antioxidant supplements, MCDB-201™ supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone™), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel™, thrombospondin, and/or vitronectin.

Cells can be cultured at different densities, e.g., cells can be seeded or maintained in the culture dish at different densities. For example, at densities, including, but not limited to, densities of less than about 2000 cells/well of a 12-well plate (for example, 12-well flat-bottom growth area: 3.8 cm2 well volume: 6.0 ml or well ID×depth (mm) 22.1×17.5; well capacity (ml) 6.5, growth area (cm2) 3.8), including less than about 1500 cells/well of a 12-well plate, less than about 1,000 cells/well of a 12-well plate, less than about 500 cells/well of a 12-well plate, or less than about 200 cells/well of a 12-well plate. The cells can also be seeded or maintained at higher densities, for example, great than about 2,000 cells/well of a 12-well plate, greater than about 2,500 cells/well of a 12-well plate, greater than about 3,000 cells/well of a 12-well plate, greater than about 3,500 cells/well of a 12-well plate, greater than about 4,000 cells/well of a 12-well plate, greater than about 4,500 cells/well of a 12-well plate, greater than about 5,000 cells/well of a 12-well plate, greater than about 5,500 cells/well of a 12-well plate, greater than about 6,000 cells/well of a 12-well plate, greater than about 6,500 cells/well of a 12-well plate, greater than about 7,000 cells/well of a 12-well plate, greater than about 7,500 cells/well of a 12-well plate or greater than about 8,000 cells/well of a 12-well plate.

EXAMPLES

The following example is provided in order to demonstrate and further illustrate certain embodiments and aspects of the present invention and is not to be construed as limiting the scope thereof.

Example 1

Materials and Methods.
Research Subject and Cell Line Derivation.

After obtaining informed parental consent we obtained a punch biopsy from the skin of a male RDEB patient with a homozygous c.1837 C>T premature termination codon mutation. Approval for research on human subjects was obtained from the University of Minnesota Institutional Review Board. A primary fibroblast cell line was derived and maintained in low oxygen concentration conditions.

TALEN and Donor Construction.

The TALEN candidate described in FIG. 1A was generated via the Golden Gate Assembly method and inserted into a homodimeric form of a CAGGs promoter driven FokI endonuclease as described [1, 2]. The left donor arm was amplified with the LAF and LAR primers shown in Table 1. The right arm was synthesized in two fragments (inner and outer) using an overlapping oligonucleotide assembly strategy as described [3, 4]. All primer sets are shown in Table 1; the left and right arms were cloned into a floxed PGK puromycin cassette.

Gene Transfer.

All TALEN treatments consisted of delivery of 2.5 μg of each TALEN and 10 μg amount of donor via the Neon Transfection System (Life Sciences) with the following instrument settings: 1500 V, 20 ms pulse width, and a single pulse. For 48 hours post gene transfer the cells were incubated at 31 C[5].

Cell Culture.

Cells were maintained in growth media comprised of DMEM supplemented with 20 FBS, 100 U/mL nonessential amino acids, and 0.1 mg/ml each of penicillin and streptomycin, respectively (invitrogen) and cultured at 2% $O_2$, 5% $CO_2$, and 37 C.

Surveyor Nuclease.

Genomic DNA was isolated 48 hours post TALEN gene transfer and amplified for 30 cycles with Surveyor F and Surveyor R primers and subjected to Surveyor nuclease treatment as described [6]. Products were resolved on a 10% TBE PAGE gel (Invitrogen). For off target amplicons the PCR reaction proceeded for 35 cycles and all primers are listed in Table 1.

Homology Directed Repair Analysis.

For quantification of HDR, TALENs and 5 μl of a 40 μM single stranded oligonucleotide donor were transfected into

TABLE 1

(SEQ ID NOs: 1-21)
TALEN correction for RDEB

| | | |
|---|---|---|
| C06 | outer fragment 1-12 | TCACGGGTAGCCAACGCTATGTCCTGATAGCGGTCCGCTTAGGAGAGAAGCGGAGGAATC |
| C07 | C7GT1 | Atcgtcccacatccctgtctctt |
| C08 | C7APAF | CAAAGGGACCAATGAGGGTA |
| C09 | C7GT2 | tctagtggggagaggcaatg |
| C10 | RT1 | TCGACTTGGATGACGTTCAG |
| C11 | RT2 | GTTCGAGCCACGATGACTG |
| C12 | Surveyor F | tttcagccatatcccagctc |
| D01 | Surveyor R | tgctccagctaatccgaaat |
| D02 | Oligo Duplex Top | G*T*CCGTACGGATCCAAGCTTCGTCGACCTAGCC |
| D03 | Oligo Duplex Bottom | CATGCCTAGGTTCGAAGCAGCTGGATCGGGG*A*C |
| D04 | Linker F | GGATCCAAGCTTCGTCGACCTAGCC |
| D05 | ssODN donor (PAGE purified) | tctgcgtccc tgtccatcac tgccatcgtc ccacatccct gtctctttct |
| D06 | | gacccctgcccacct agtagtgtgtgcccgtctgt t gt gtgactctggtaa ctagag acttctcagacccttttagtc acttggatgac gttcaggccg ggcttagctc cactgtgcgg gtgtctgctc gagtgggtcc ccgtgacggg a |
| D07 | Off target surveyor primers | |
| D08 | 1q23.3 FWD | TCTCAGGCAAGAAAATTGGA |
| D09 | 1q23.3 REV | TGTGCATTTATTCTGTGTCTTGTT |
| D10 | 5q33.1 FWD | GAGTTCCCTTGGGCCTATTC |
| D11 | 5q33.1 REV | GGCTGCAGTGAGCTATGATG |
| D12 | 7q21.3 FWD | ACTCCAAGTCACAGGGGATG |
| E01 | 7q21.3 REV | CAGCTCTGACTGCTGTTTGC |
| E02 | 16p13.3 FWD | TTGCTCACAGAAGGACCACA |
| E03 | 16p13.3 REV | ACGTGGGTGTGACGGTTATT | cells and screened by PCR at 48 hours using three primers: Surveyor F, Surveyor R, and linker forward primers. Densitometry was performed as described [6]. For gene correction, 10 μg of the donor plasmid was introduced along with the 2.5 μg each of TALEN DNA and selection was performed as described subsequently.

Selection.

Cells were selected in bulk in 0.2 μg/mL puromycin, segregated into sub-pools, screened for HDR, and then plated at low density (250-750 total cells) in a 10 cm² dish. A cloning disk with silicone grease (all from Corning) was placed over single cells in the presence of base media supplemented with 10 ng/mL epidermal growth factor and 0.5 ng/mL fibroblast growth factor. Cells were expanded to sequentially larger vessels. An adenoviral cre recombinase was added at an MOI of 20 to remove the PGK puromycin cassette (Vector BioLabs).

Cell Correction Molecular Screening.

C7GT1 and C7GT2 primer pairs were employed to amplify a junction from the donor into the endogenous locus (upstream SPMP screening). The ApaI SPMP region was assessed on genomic DNA treated with ApaI pre- and post-PCR amplification with C7APAF and C7GT2. Messenger RNA from clonal isolates was converted to cDNA and screened with RT1 and RT2 and then digested with ApaI. ApaI-resistant amplicons were cloned and Sanger sequenced.

Cell Expansion Analysis.

Gene corrected fibroblasts were expanded in T150 flasks and trypsinized to obtain single cell suspensions. Cells were then resuspended in 100 ul PBS+0.5% BSA+propidium iodide (eBiosciences), followed by addition of an equal volume of PKH26 reference microbeads (SIGMA). Five thousand bead events were collected and absolute viable cell number was calculated as per manufacturer protocol (SIGMA).

iPSC Generation and Teratoma Assay.

Gene corrected fibroblasts (or un-corrected cells as a control) were reprogrammed to iPSCs as described [7, 8] and then placed in the flank of a SCID mouse until a visible mass formed. The mass was excised for embedding and staining.

Immunofluorescence.

Gene corrected cells were plated on a chamber slide and were fixed 24 hours later with 4% paraformaldehyde, permeabilized with 0.2% Triton X, blocked with 1% BSA and stained with a polyclonal anti-type VII collagen antibody (1:1500; generously provided by Drs David Woodley and Mei Chen). Secondary antibody staining was performed with donkey anti-rabbit IgG Cy3 (1:500; Jackson Immunoresearch). Isotype control staining was done using whole molecule rabbit IgG (Jackson Immunoresearch). Nuclei were stained with 4',6-diamidino-2-phenylindole (Vector Laboratories). Images were taken using a PMT voltage of 745 on an Olympus BX61 FV500 confocal microscope (Olympus Optical Co LTD) and analyzed using the Fluoview software version 4.3. Light microscopy was performed on a Leica microscope. IDLV and LAM-PCR/nrLAM PCR.

Integrase-defective lentiviral (IDLV) particles were produced in 293T cells via lipid based co-transfection (Lipofectamine 2000, Invitrogen) of the CMV-GFP transfer vector, the pCMV-ΔR8.2 packaging plasmid harboring the D64V integrase mutation [9, 10], and the pMD2.VSV-G envelope-encoding plasmid. Gene tagging was performed by nucleofection of HEK 293 cells with the TALENs followed 24 hours later by a transduction of GFP IDLV at an MOI of 7. 100 ng of genomic DNA was analyzed in duplicate by LAM-PCR [11] using enzymes MscI and Tsp509I and nrLAM-PCR [12] to ensure genome-wide recovery of IDLV integration sites. (nr)LAM-PCR amplicons were sequenced by the Roche/454 pyrosequencing platform and integration site data were analyzed using the HISAP pipeline [13, 14],[15]. Genomic position harboring >1 IS in close distance were scanned for potential TALEN off-target binding sites using the pattern matcher scan-for-matches [13].

Results/Discussion

Lack of type VII collagen protein at the dermal-epidermal junction (DEJ) results in loss of the structural integrity of the skin. Restoration of deposition of the type VII collagen at the DEJ by allogeneic systemic hematopoietic cell or localized fibroblast transplantation can alleviate symptoms [16-18]. However, suboptimal efficacy of allogeneic cell transplantation due to risks of toxicity, infection, and graft failure provides impetus to develop new autologous cell-based therapies. Therefore, a genome-editing strategy for COL7A1 correction based on TALEN technology is described herein. Fibroblasts are an ideal cell type due to their ease of derivation and low susceptibility to growth arrest in culture as well as their ability to deposit type VII collagen at the DEJ [18, 19]. TALENs are engineered nucleases that can induce a double-stranded DNA break at a user-defined genomic locus, thus stimulating HDR, and are superior to other nucleases in their targeting capacity and ease of generation [20, 21].

Figure 2:
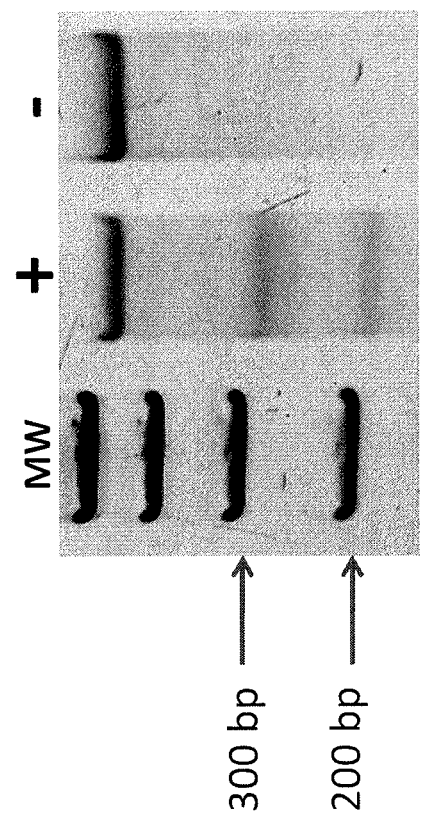
FIG. 2. TALEN modification of COL7A1 gene assessed by Surveyor nuclease assay. NHEJ assessment by Surveyor nuclease in RDEB fibroblasts. Limiting cycle PCR of a ~350 bp fragment was performed followed by Surveyor mismatch assay. TALEN induced NHEJ is evidenced by the predictable banding pattern of ~200 and 300 bp (arrows). At right is the unmodified COL7A1 locus in control cells.

The TAL Effector-Nucleotide Targeter software [22, 23] identified 68 potential TALEN sites for the human COL7A1 locus and support recent experimental data on a large series of human genes [21] emphasize the high targeting capacity for TALENs, a consideration for RDEB and other diseases that exhibit heterogeneity in the location and number of mutated sequences. The Golden Gate cloning methodology was used to generate a patient-specific nuclease proximal to a premature termination codon in exon 14 of the COL7A1 gene (FIG. 1A). A TALEN is composed of an engineered TALE repeat array fused to the FokI nuclease domain (FIG. 1B); the binding specificities of TALE repeats in the array are dictated by the identities of two hypervariable residues within each repeat (FIG. 1C). TALEN-treated RDEB fibroblasts were analyzed for evidence of repair by the two major DNA repair pathways: error-prone non-homologous end-joining (NHEJ) and HDR. Surveyor nuclease assay and Sanger sequencing that showed 11 mutated alleles out of 75 total analyzed were consistent with NHEJ (FIGS. 2A and 2E). TALEN cleavage also resulted in the capture of an oligonucleotide duplex at the DNA break site (FIGS. 2B-F) [24]. These data established that the nuclease is active at the target site. It was next ascertained whether RDEB cells could undergo HDR following co-delivery of TALENs and an oligonucleotide donor (ODN) containing a unique primer sequence flanked by short donor arms (FIG. 1F). RDEB fibroblasts transfected with TALEN plasmids and the ODN were then analyzed with a three-primer PCR approach that simultaneously detects the modified and unmodified alleles. This assay showed that TALENs in RDEB cells can stimulate HDR to incorporate an exogenous sequence from the ODN donor (FIG. 1G) and the 14.6% rate of NHEJ and 2.1% rate of HDR show the efficacy of TALEN use for high-level modification of human fibroblasts.

Figure 4A:
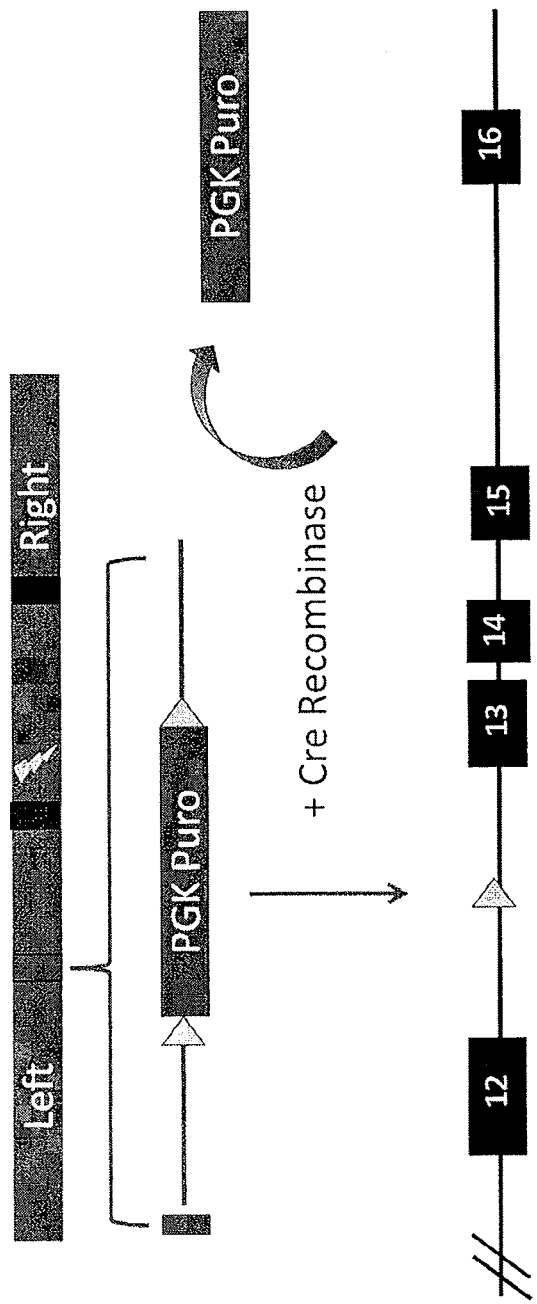
FIG. 4A-4B. Cre recombinase excision of PGK-puromycin.
Figure 4B:
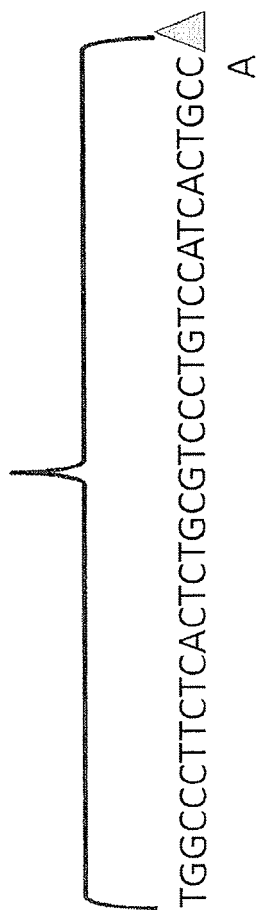

To determine whether a COL7A1 mutation causing RDEB could be corrected and a population of genetically corrected cells subsequently expanded, an exogenous donor plasmid was generated that would allow for selective detection and expansion of gene-corrected cells. This donor consisted of homology arms that spanned ~1 kb of the COL7A1 locus between exons 12 and 16 (FIG. 3A). Within the donor was a floxed-PGK-puromycin cassette oriented so that it would be inserted into the intron between exons 12 and 13. The flanking loxP sites allow for removal of the selectable marker with Cre recombinase, leaving a small loxP "footprint" in the intron (FIG. 4). Within the right donor arm, five single base pair alterations were engineered: the normal base at the site of the mutation that restores a normal genotype and four silent point mutation polymorphisms (SPMPs) that allowed for delineation of HDR-modified alleles versus unmodified ones (FIG. 3A). Three of these SPMPs are upstream of the target base and the one downstream removes an ApaI restriction site (alterations hereafter referred to as upstream or downstream SPMPs).

Of the nine clones analyzed, four were obtained that showed evidence of HDR. In one clone, the presence of the upstream SPMPs was evident; however, the RDEB-pathogenic COL7A1 mutation persisted and the downstream SPMP was not found (FIG. 5). These data suggest that an HDR crossover event occurred within the donor arm upstream of the region that restores a normal genotype (FIG. 6). For the remaining three clones, however, the downstream donor-inserted SPMP was detectable, indicating that one allele underwent HDR and the other did not, resulting in a heterozygous COL7A1 locus (FIGS. 3B and 3C).

Figure 8:
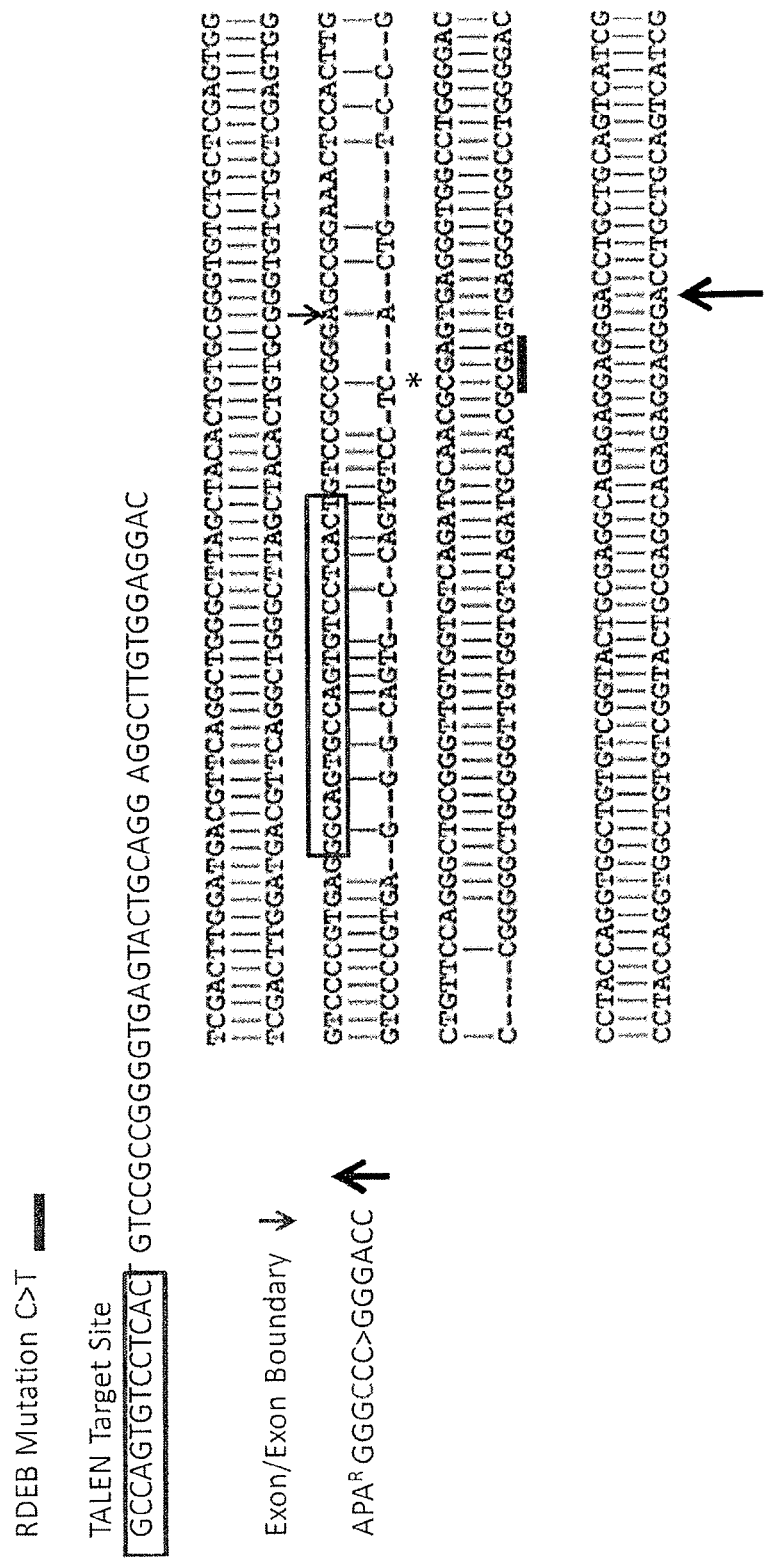
FIG. 8. Sequence analysis of TALEN cutting of donor. (SEQ ID NO: 60). cDNA from TALEN treated RDEB fibroblasts was analyzed by direct Sanger sequencing. The TALEN site is outlined in a red box (note that it is a partial TALEN sequence as the remainder of the site is within the adjacent intron. Arrow shows an exon/exon boundary). The RDEB mutation is underlined and showed a reversion to the wild type status (mutant=T, normal=C). The downstream ApaI SPMP is present and shown. Sequence alignment is of the cDNA sequence expected to be encoded by the donor on top and the recovered sequence on the bottom. The dashes/gaps show the deletions likely due to post-HDR TALEN cutting that induced subsequent NHEJ (non-homologous end joining). (SEQ ID NO:61; SEQ ID NO: 62).
Figure 10A:
FIGS. 10A-10B. Sanger sequencing of mRNA from TALEN corrected fibroblasts.
Figure 10B:
Figure 13:
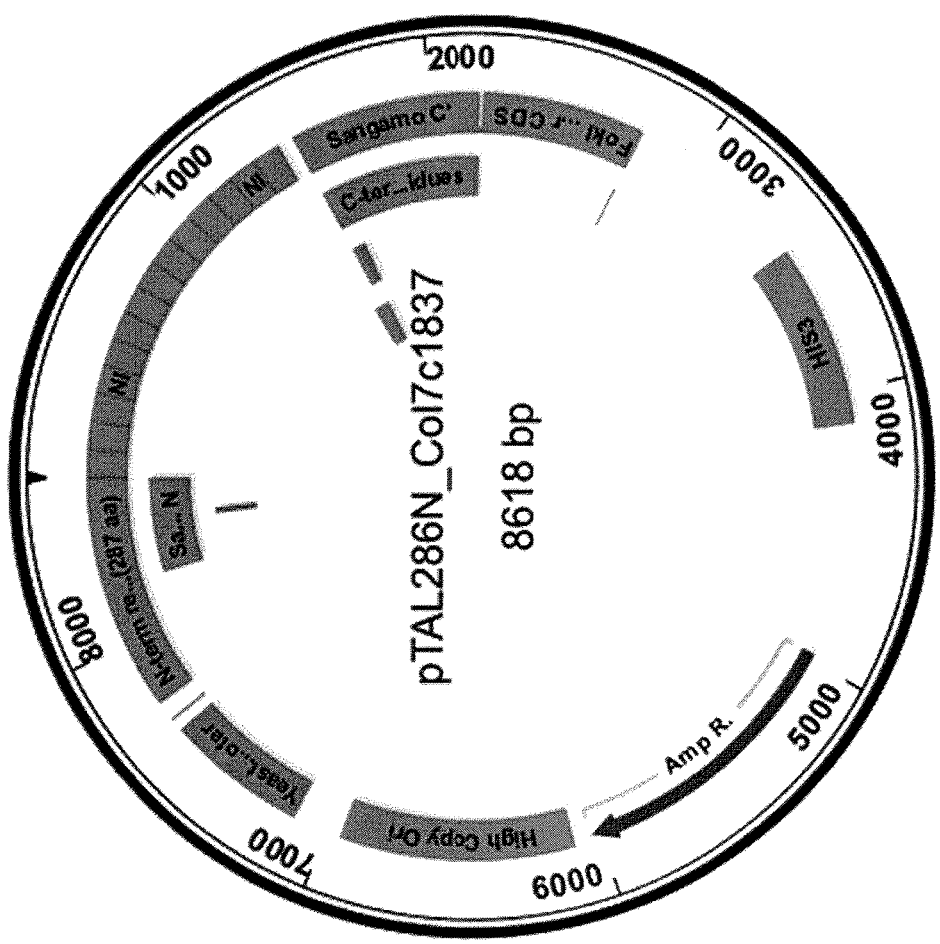
FIGS. 13 and 14 depict constructs.
Figure 14:
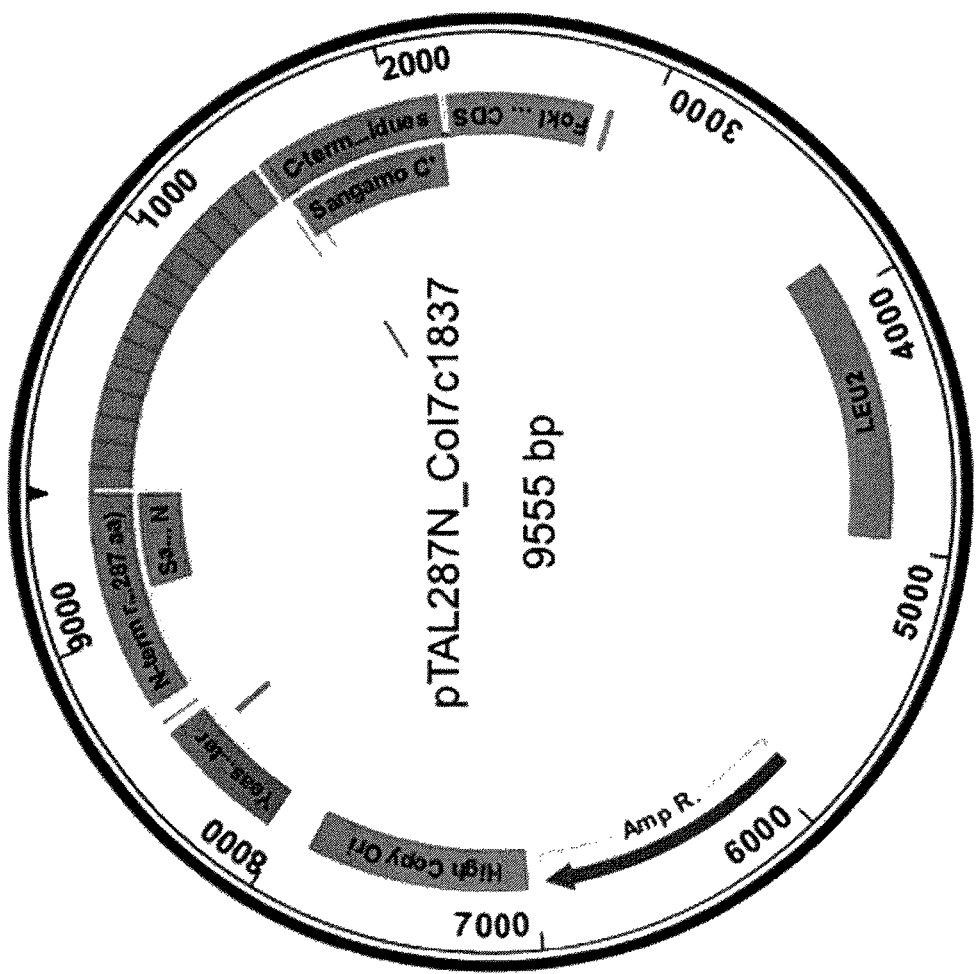

HDR should revert the mutant base and restore normal gene expression. Accordingly, this was assessed with an RT-PCR strategy for the detection of the normal base and the downstream SPMPs in the same transcript following splicing out of the intervening intron (FIG. 7). Interestingly, direct sequencing of the cDNA in one clone showed a deletion of sequences at the TALEN target site (FIG. 8). These data indicate that the TALEN was active after HDR and induced an additional NHEJ-mediated mutation. Previous studies with zinc finger endonucleases (ZFNs) show that silent mutations in the donor sequence can reduce the frequency of this undesired event[12]; however, this was not possible in this experiment because the TALEN site was at an intron/exon boundary and it was opted to leave the donor TALEN sequence unperturbed so as not to disrupt splicing. This negatively impacted the recovery of one clone; however, two clones exhibited the desired HDR-based, donor-derived, normal transcripts (FIG. 9A). It was next ascertained whether TALEN treatment restored type VII collagen protein expression compared to untreated RDEB mutant or wild-type cells bearing abnormal or normal transcripts, respectively (FIGS. 9C and 9E). Immunofluorescence-based detection of type VII collagen revealed a rescue of type VII collagen production in TALEN-treated cells and a complete absence in untreated control RDEB fibroblasts (FIGS. 9B and 9D). These results confirm the ability of TALENs to mediate a genetic modification at a disease-specific target site with restoration of normal mRNA and protein production.

The risk of off-target effects is a consideration in the clinical use of genome-editing reagents. Options for mapping off-target sites of gene-editing nucleases include: (i) performing in vitro Systematic Evolution of Ligands by Exponential Enrichment (SELEX) with monomeric DNA-binding proteins of each nuclease in a pair and then using this data to predict potential off target sites[25], (ii) performing an in vitro cleavage site selection using dimeric nucleases and then interrogating sites from this selection that occur in the genome of cells of interest for nuclease-induced mutations, (iii) utilizing the propensity of an integration-defective lentivirus (IDLV) to integrate into nuclease-induced DSBs and then identifying points of insertion by LAM-PCR[9]. Although methods (ii) and (iii) appear to be better at identifying nuclease off-target sites than method (i), the former methods fail to identify off-target sites predicted by the other, suggesting that no method is comprehensive in its detection of off-target events. Method (iii) was utilized with an IDLV with green fluorescent protein (GFP) gene that can be trapped into a nuclease-generated DSB (FIG. 11A)[9, 26]. Human embryonic kidney (293) cells were used due to their accelerated proliferative capacity, which should promote rapid dilution of non-integrated IDLV and minimize random integration. In addition, it was hypothesized that, due to the open chromatin structure of 293 cells, any off-target effects will manifest to a greater degree than in primary cells and will allow for a more sensitive mapping of off-target events. Introduction of the GFP IDLV alone resulted in a rapid loss of GFP expression in 293 cells (FIG. 12). The co-introduction of IDLV and TALENs resulted in a stable population of GFP cells (FIG. 11B), which were used for mapping the integration sites with nonrestrictive linear amplification-mediated PCR ((nr)LAM-PCR) (FIG. 11C). Five sites were recovered that showed a junction between the IDLV and adjacent genomic sequence (FIG. 11D). These events are not unexpected, as even nucleases used in clinical trials show off-target effects [9] and the non-coding regions recovered suggest that this TALEN possesses a safety profile that is not predicted to negatively impact gene expression.

At the resolution of the LAM-PCR methodology, the TALEN described herein shows a high rate of on-target activity. In addition, these studies, like others, show that a potential target for engineered nucleases is the donor construct itself and they highlight the benefits of the inclusion of a marker sequence that can aid in selection of the desired HDR event [27].

In summary, skin cells from an RDEB patient were obtained and the donor and TALEN reagents (sequences are included below) were designed and rapidly constructed to specifically target this unique mutation. The application of the gene editing tools resulted in correction of the RDEB mutation in diploid human fibroblasts—cells that are suitable for therapeutic use after direct expansion or reprogramming into pluripotency followed by expansion [7, 8]—and provide the first-ever demonstration of TALEN-mediated correction of a disease gene in the human genome. These studies provide the proof that TALENs can be used in the development of clinically relevant individualized therapies.

Example 2

An example of a Donor Plasmid Sequence is set forth in SEQ ID NO: 22. An example of the Left Arm of the Donor Sequence is set forth in SEQ ID NO:31. An example of the Loxp site of Donor is set forth in SEQ ID NO:23. An example of the PGK Promoter of Donor is set forth in SEQ ID NO:24. An example of the Puromycin Gene of the Donor sequence is set forth in SEQ ID NO:25. An example of the Bovine Growth Hormone polyadenylation signal of Donor is set forth in SEQ ID NO:26. An example of the Loxp Site Of Donor is set forth in SEQ ID NO:27. An example of the Right Arm of Donor is set forth in SEQ ID NO:28. An example of TALEN Left (pTAL 286) is set forth in SEQ ID NO:29. An example of TALEN Right (pTAL 287) is set forth in SEQ ID NO:30.

BIBLIOGRAPHY

1. Carlson, D. F., et al. Efficient TALEN-mediated gene knockout in livestock. *Proceedings of the National Academy of Sciences of the United States of America* 109: 17382-17387.

2. Cermak, T., et al. Efficient design and assembly of custom TALEN and other TAL effector-based constructs for DNA targeting. *Nucleic acids research* 39: e82.
3. Osborn, M. J., Defeo, A. P., Blazar, B. R., and Tolar, J. Synthetic Zinc Finger Nuclease Design and Rapid Assembly. *Human gene therapy*.
4. Gibson, D. G., Young, L., Chuang, R. Y., Venter, J. C., Hutchison, C. A., 3rd, and Smith, H. O. (2009). Enzymatic assembly of DNA molecules up to several hundred kilobases. *Nature methods* 6: 343-345.
5. Doyon, Y., Choi, V. M., Xia, D. F., Vo, T. D., Gregory, P. D., and Holmes, M. C. Transient cold shock enhances zinc-finger nuclease-mediated gene disruption. *Nature methods* 7: 459-460.
6. Guschin, D. Y., Waite, A. J., Katibah, G. E., Miller, J. C., Holmes, M. C., and Rebar, E. J. A rapid and general assay for monitoring endogenous gene modification. *Methods in molecular biology* (Clifton, N.J. 649: 247-256.
7. Tolar, J., et al. Keratinocytes from Induced Pluripotent Stem Cells in Junctional Epidermolysis Bullosa. *The Journal of investigative dermatology*.
8. Tolar, J., et al. Induced pluripotent stem cells from individuals with recessive dystrophic epidermolysis bullosa. *The Journal of investigative dermatology* 131: 848-856.
9. Gabriel, R., et al. An unbiased genome-wide analysis of zinc-finger nuclease specificity. *Nature biotechnology* 29: 816-823.
10. Vargas, J., Jr., Gusella, G. L., Najfeld, V., Klotman, M. E., and Cara, A. (2004). Novel integrase-defective lentiviral episomal vectors for gene transfer. *Human gene therapy* 15: 361-372.
11. Schmidt, M., et al. (2007). High-resolution insertion-site analysis by linear amplification-mediated PCR (LAM-PCR). *Nat Methods* 4: 1051-1057.
12. Paruzynski, A., et al. (2010). Genome-wide high-throughput integrome analyses by nrLAM-PCR and next-generation sequencing. *Nat Protoc* 5: 1379-1395.
13. Dsouza, M., Larsen, N., and Overbeek, R. (1997). Searching for patterns in genomic data. *Trends Genet* 13: 497-498.
14. Arens, A., et al. Bioinformatic clonality analysis of next-generation sequencing-derived viral vector integration sites. *Human gene therapy methods* 23: 111-118.
15. Arens, A., et al. (2012). Bioinformatic clonality analysis of next-generation sequencing-derived viral vector integration sites. *Hum Gene Ther Methods* 23: 111-118.
16. Wagner, J. E., et al. Bone marrow transplantation for recessive dystrophic epidermolysis bullosa. *The New England journal of medicine* 363: 629-639.
17. Tolar, J., et al. (2009). Amelioration of epidermolysis bullosa by transfer of wild-type bone marrow cells. *Blood* 113: 1167-1174.
18. Wong, T., et al. (2008). Potential of fibroblast cell therapy for recessive dystrophic epidermolysis bullosa. *The Journal of investigative dermatology* 128: 2179-2189.
19. Goto, M., et al. (2006). Fibroblasts show more potential as target cells than keratinocytes in COL7A1 gene therapy of dystrophic epidermolysis bullosa. *The Journal of investigative dermatology* 126: 766-772.
20. Cermak, T., et al. Efficient design and assembly of custom TALEN and other TAL effector-based constructs for DNA targeting. *Nucleic acids research*.
21. Reyon, D., Tsai, S. Q., Khayter, C., Foden, J. A., Sander, J. D., and Joung, J. K. FLASH assembly of TALENs for high-throughput genome editing. *Nature biotechnology* 30: 460-465.
22. Sander, J. D., Zaback, P., Joung, J. K., Voytas, D. F., and Dobbs, D. (2007). Zinc Finger Targeter (ZiFiT): an engineered zinc finger/target site design tool. *Nucleic acids research* 35: W599-605.
23. Doyle, E. L., et al. TAL Effector-Nucleotide Targeter (TALE-NT) 2.0: tools for TAL effector design and target prediction. *Nucleic acids research* 40: W117-122.
24. Orlando, S. J., et al. Zinc-finger nuclease-driven targeted integration into mammalian genomes using donors with limited chromosomal homology. *Nucleic acids research* 38: e152.
25. Pattanayak, V., Ramirez, C. L., Joung, J. K., and Liu, D. R. Revealing off-target cleavage specificities of zinc-finger nucleases by in vitro selection. *Nature methods* 8: 765-770.
26. Paruzynski, A., et al. Genome-wide high-throughput integrome analyses by nrLAM-PCR and next-generation sequencing. *Nature protocols* 5: 1379-1395.
27. Zou, J., et al. (2009). Gene targeting of a disease-related gene in human induced pluripotent stem and embryonic stem cells. *Cell stem cell* 5: 97-110.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method to treat a genetic disease or disorder caused by a genetic mutation in a target gene comprising: contacting a cell with
 a composition comprising a nucleic acid encoding at least one TALEN protein, wherein the at least one TALEN protein is capable of inducing a site-specific double stranded DNA break in a target gene in a cell, wherein the target gene is a COL7A1 gene; and
 a nucleic acid donor sequence,
 wherein the donor sequence is a template for correction of a genetic mutation in the Col7A1 target gene, and
 further wherein the genetic mutation is capable of causing epidermolysis bullosa,
 thereby treating the genetic disease or disorder caused by the genetic mutation in the target gene.

2. The method of claim 1, wherein the cell is selected from the group consisting of a fibroblast, keratinocyte, inducible pluripotent stem cell, hematopoietic stem cell, mesenchymal stem cell, embryonic stem cell, hematopoietic progeny cell, T-cell, B-cell, glial cell, neural cell, neuroglial progenitor cell, neuroglial stem cell, muscle cell, lung cell, pancreatic cell, liver cell and a cell of the reticular endothelial system.

3. The method of claim 1, wherein the composition comprises a nucleic acid which encodes a first TALEN protein which is a left TALEN and the composition compromises a nucleic acid which encodes a second TALEN which is a right TALEN that cooperates with the left TALEN to make a site-specific double stranded DNA break in the target gene.

4. The method of claim 1, wherein the nucleic acid encoding the TALEN or the nucleic acid donor sequence is part of a vector or plasmid.

5. The method of claim 3, wherein the first TALEN and/or the second TALEN comprise a plurality of TAL effector repeat sequences and the endonuclease domain and a spacer between the plurality of TAL effector repeat sequences and the endonuclease domain includes a spacer.

6. The method of claim 5, wherein the spacer is 12 to 30 nucleotides in length.

* * * * *

SEQUENCE LISTING

```
<160> NUMBER OF SEQ ID NOS: 75

<210> SEQ ID NO 1
<211> LENGTH: 61
<212> TYPE: DNA
<213> ORGANISM: Artificial Sequence
<220> FEATURE:
<223> OTHER INFORMATION: Outer Fragment 1-12

<400> SEQUENCE: 1
tcacgggtag ccaacgctat ggtcctgata gcggtccgct taggagagaa gcggaggaat     60
c                                                                      61
```

```
<210> SEQ ID NO 2
<211> LENGTH: 22
<212> TYPE: DNA
<213> ORGANISM: Artificial Sequence
<220> FEATURE:
<223> OTHER INFORMATION: C7GT1

<400> SEQUENCE: 2
atcgtccaca tccctgtctc tt                                                  22

<210> SEQ ID NO 3
<211> LENGTH: 20
<212> TYPE: DNA
<213> ORGANISM: Artificial Sequence
<220> FEATURE:
<223> OTHER INFORMATION: C7APAF

<400> SEQUENCE: 3
caaagggacc aatgagggta                                                     20

<210> SEQ ID NO 4
<211> LENGTH: 21
<212> TYPE: DNA
<213> ORGANISM: Artificial Sequence
<220> FEATURE:
<223> OTHER INFORMATION: C7GT2

<400> SEQUENCE: 4
tctagtgggg agaggccaat g                                                   21

<210> SEQ ID NO 5
<211> LENGTH: 20
<212> TYPE: DNA
<213> ORGANISM: Artificial Sequence
<220> FEATURE:
<223> OTHER INFORMATION: RT1

<400> SEQUENCE: 5
tcgacttgga tgacgttcag                                                     20

<210> SEQ ID NO 6
<211> LENGTH: 19
<212> TYPE: DNA
<213> ORGANISM: Artificial Sequence
<220> FEATURE:
<223> OTHER INFORMATION: RT2

<400> SEQUENCE: 6
gttcgagcca cgatgactg                                                      19

<210> SEQ ID NO 7
<211> LENGTH: 21
<212> TYPE: DNA
<213> ORGANISM: Artificial Sequence
<220> FEATURE:
<223> OTHER INFORMATION: Surveyor F

<400> SEQUENCE: 7
ttttcagcca tatcccagct c                                                   21

<210> SEQ ID NO 8
<211> LENGTH: 20
<212> TYPE: DNA
<213> ORGANISM: Artificial Sequence
<220> FEATURE:
<223> OTHER INFORMATION: Surveyor R
```

```
<400> SEQUENCE: 8
tgctccagct aatccgaaat                                              20

<210> SEQ ID NO 9
<211> LENGTH: 33
<212> TYPE: DNA
<213> ORGANISM: Artificial Sequence
<220> FEATURE:
<223> OTHER INFORMATION: Oligo Duplex Top

<400> SEQUENCE: 9
gtccgtacgg atccaagctt cgtcgaccta gcc                               33

<210> SEQ ID NO 10
<211> LENGTH: 33
<212> TYPE: DNA
<213> ORGANISM: Artificial Sequence
<220> FEATURE:
<223> OTHER INFORMATION: Oligo Duplex Bottom

<400> SEQUENCE: 10
catgcctagg ttcgaagcag ctggatcggg gac                               33

<210> SEQ ID NO 11
<211> LENGTH: 25
<212> TYPE: DNA
<213> ORGANISM: Artificial Sequence
<220> FEATURE:
<223> OTHER INFORMATION: Linker F

<400> SEQUENCE: 11
ggatccaagc ttcgtcgacc tagcc                                        25

<210> SEQ ID NO 12
<211> LENGTH: 64
<212> TYPE: DNA
<213> ORGANISM: Artificial Sequence
<220> FEATURE:
<223> OTHER INFORMATION: ssODN Donor (PAGE Purified)

<400> SEQUENCE: 12
tctgcgtccc tgtcatcact gccatcgtcc cacatccctg tctctttctg accctgccc   60 acct                                                               64

<210> SEQ ID NO 13
<211> LENGTH: 133
<212> TYPE: DNA
<213> ORGANISM: Artificial Sequence
<220> FEATURE:
<223> OTHER INFORMATION: Primers

<400> SEQUENCE: 13
agtagtgtgt gccagctgtt gtgtgactct ggtaactaga gatccctcag acccttttag  60
tcacttggat gacgttcagg ctgggcttag ctacactgtg cgggtgtctg ctcgagtggt 120
ccccgtgagg gca                                                    133

<210> SEQ ID NO 14
<211> LENGTH: 20
<212> TYPE: DNA
<213> ORGANISM: Artificial Sequence
<220> FEATURE:
<223> OTHER INFORMATION: Primers
```

```
<400> SEQUENCE: 14
tctcaggcaa gaaaattgga                                                    20

<210> SEQ ID NO 15
<211> LENGTH: 24
<212> TYPE: DNA
<213> ORGANISM: Artificial Sequence
<220> FEATURE:
<223> OTHER INFORMATION: 1Q23.3 REV

<400> SEQUENCE: 15
tgtgcattta ttctgtgtct tgtt                                               24

<210> SEQ ID NO 16
<211> LENGTH: 20
<212> TYPE: DNA
<213> ORGANISM: Artificial Sequence
<220> FEATURE:
<223> OTHER INFORMATION: 5q33.1 FWD

<400> SEQUENCE: 16
gagttccctt gggcctattc                                                    20

<210> SEQ ID NO 17
<211> LENGTH: 20
<212> TYPE: DNA
<213> ORGANISM: Artificial Sequence
<220> FEATURE:
<223> OTHER INFORMATION: 5q33.1 REV

<400> SEQUENCE: 17
ggctgcagtg agctatgatg                                                    20

<210> SEQ ID NO 18
<211> LENGTH: 20
<212> TYPE: DNA
<213> ORGANISM: Artificial Sequence
<220> FEATURE:
<223> OTHER INFORMATION: 7q21.3 FWD

<400> SEQUENCE: 18
actccaagtc acagggatg                                                     20

<210> SEQ ID NO 19
<211> LENGTH: 20
<212> TYPE: DNA
<213> ORGANISM: Artificial Sequence
<220> FEATURE:
<223> OTHER INFORMATION: 7q21.3 REV

<400> SEQUENCE: 19
cagctctgac tgctgtttgc                                                    20

<210> SEQ ID NO 20
<211> LENGTH: 20
<212> TYPE: DNA
<213> ORGANISM: Artificial Sequence
<220> FEATURE:
<223> OTHER INFORMATION: 16p13.3 FWD

<400> SEQUENCE: 20
ttgctcacag aaggaccaca                                                    20
```

```
<210> SEQ ID NO 21
<211> LENGTH: 20
<212> TYPE: DNA
<213> ORGANISM: Artificial Sequence
<220> FEATURE:
<223> OTHER INFORMATION: 16p13.3 REV

<400> SEQUENCE: 21
acgtgggtgt gacggttatt                                              20

<210> SEQ ID NO 22
<211> LENGTH: 2950
<212> TYPE: DNA
<213> ORGANISM: Artificial Sequence
<220> FEATURE:
<223> OTHER INFORMATION: Donor Plasmid Sequence

<400> SEQUENCE: 22
gcctgtgagc cctgtaacag acctgcaagc caccgagctg cccgggcagc gggtgcgagt    60
gtcctggagc ccagtccctg gtgccaccca gtaccgcatc attgtgcgca gcacccaggg   120
tgaggtggac gcagccagca cccccaccac acacactgaa gttccagcct gagggtctg    180 agtgtacctc cagccctctc cttccacacc tgggtcccta gtctcctc cctgtctcgt    240 tatccatctg cttcccaaga tggcactgag ccctgaactg tcaacagggt gtgtctgccc    300
ctaccctacc ccaaccaatc tcctccctgc cccacacccc atccacggct ttcacctctg   360
cacagccaca agctcaatca cctgtctttc tgttacccta gtggtgacca ctgtacacca   420
acctctcatt gcatgtcccc atccagcact gacctctgcc atcccacatc agtgtctgtc   480
aatggctcat cagttctcac tgcagtccac tgactcctgt catcctacat gctaagatcc   540
cacagactcc tgtcctccag tgtccctgac catcactggc ccctttcatc ctatgtcctt   600
gtcttgcact cactttttc agccatatcc cagctctctg gtccccacca ccccacatcc    660 ccaccccat ggcccttctc actctgcgtc cctgtccatc actgccataa cttcgtataa    720
tgtatgctat acgaagttat caaggcagtc tggagcatgc gctttagcag ccccgctggg   780
cacttggcgc tacacaagtg gcctctggcc tcgcacacat tccacatcca ccggtaggcg   840
ccaaccggct ccgttctttg gtggccccctt cgcgccacct tctactcctc ccctagtcag   900
gaagttcccc cccgccccgc agctcgcgtc gtgcaggacg tgacaaatgg aagtagcacg   960
tctcactagt ctcgtgcaga tggacagcac cgctgagcaa tggaagcggg taggcctttg  1020
gggcagcggc caatagcagc tttgctcctt cgctttctgg gctcagaggc tgggaagggg  1080
tgggtccggg ggcgggctca ggggcgggct caggggcggg gcgggcgccc gaaggtcctc  1140
cggaggcccg gcattctgca cgcttcaaaa gcgcacgtct gccgcgctgt tctcctcttc  1200
ctcatctccg ggccttttcga cctgcagccc aagcttacca tgaccgagta caagcccacg  1260
gtgcgcctcg ccacccgcga cgacgtcccc agggccgtac gcaccctcgc cgccgcgttc  1320
gccgactacc ccgccacgcg ccacaccgtc gatccggacc gccacatcga gcgggtcacc  1380
gagctgcaag aactcttcct cacgcgcgtc gggctcgaca tcggcaaggt gtgggtcgcg  1440
gacgacggcg ccgcggtggc ggtctggacc acgccggaga gcgtcgaagc gggggcggtg  1500
ttcgccgaga tcggcccgcg catggccgag ttgagcggtt cccggctggc cgcgcagcaa  1560 cagatgaag gcctcctggc gccgcaccgg cccaaggagc ccgcgtggtt cctggccacc  1620
gtcggcgtct cgcccgacca ccagggcaag ggtctgggca gcgccgtcgt gctccccgga  1680
gtggaggcgg ccgagcgcgc cggggtgccc gccttcctgg agacctcgcg ccccgcaac  1740
```

-continued

```
ctccccttct acgagcggct cggcttcacc gtcaccgccg acgtcgaggt gcccgaagga   1800
ccgcgcacct ggtgcatgac ccgcaagccc ggtgcccatc atcaccatca ccattgagtt   1860
taaacccgct gatcagcctc gactgtgcct tctagttgcc agccatctgt tgtttgcccc   1920 tccccgtgc cttccttgac cctggaaggt gccactccca ctgtcctttc ctaataaaat    1980
gaggaaattg catcgcattg tctgagtagg tgtcattcta ttctgggggg tggggtgggg   2040
caggacagca aggggagga ttgggaagac aatagcaggc atgctgggga tgcggtgggc    2100
tctatggctt ctgaggcgga agaaccagc tataacttcg tataatgtat gctatacgaa    2160
gttatctcga gatcgtccca catccctgtc tctttctgac ccctgcccac ctaccctgac   2220
ttctctctta ggggttgagc ggaccctggt gcttcctggg agtcagacag cattcgactt   2280
ggatgacgtt caggctgggc ttagctacac tgtgcgggtg tctgctagag tgggtccccg   2340
tgagggcagc gctagcgtgc tgaccgtccg ccggggtgag tactgcagga ggcttgtgga   2400
ggacagctgc ctgcctcact ctggtcctgg ttctgacttc tgacttctgt ctgtaactcc   2460
tagagccgga aactccactt gctgttccag ggctgcgggt tgtggtgtca gatgcaacgc   2520
gagtgagggt ggcctgggga cccgtccctg gagctagtgg atttcggatt agctggagca   2580
caggcagtgg tcagtgtggg gtgtgtgggg gactgccaaa gggaccaatg agggtatggg   2640
tgccagaggg gacaggcagg agccatgcca gcatttccct ctgacctcag gtccggagtc   2700
cagccagaca ctgcccccag actctactgc cacagacatc acagggctgc agcctggaac   2760
cacctaccag gtggctgtgt cggtactgcg aggcagagag gagggacctg ctgcagtcat   2820
cgtggctcga acgggtcagg ccctgccccc gtcccttggc tctctgcctc cattgctctt   2880 tcagacccc atgccttccc ttgcagaccc ttgcttctcc ccagaactcc tgcctccccc    2940
ttcagaatcc                                                         2950

<210> SEQ ID NO 23
<211> LENGTH: 34
<212> TYPE: DNA
<213> ORGANISM: Artificial Sequence
<220> FEATURE:
<223> OTHER INFORMATION: Loxp site of Donor

<400> SEQUENCE: 23
ataacttcgt ataatgtatg ctatacgaag ttat                              34

<210> SEQ ID NO 24
<211> LENGTH: 484
<212> TYPE: DNA
<213> ORGANISM: Artificial Sequence
<220> FEATURE:
<223> OTHER INFORMATION: PGK Promoter of Donor

<400> SEQUENCE: 24
caaggcagtc tggagcatgc gctttagcag ccccgctggg cacttggcgc tacacaagtg     60
gcctctggcc tcgcacacat tccacatcca ccggtaggcg ccaaccggct ccgttctttg    120
gtggcccctt cgcgccacct tctactcctc ccctagtcag gaagttcccc cccgccccgc    180
agctcgcgtc gtgcaggacg tgacaaatgg aagtagcacg tctcactagt ctcgtgcaga    240
tggacagcac cgctgagcaa tggaagcggg taggcctttg gggcagcggc caatagcagc    300
tttgctcctt cgctttctgg gctcagaggc tgggaagggg tgggtccggg ggcgggctca    360
ggggcgggct caggggcggg gcgggcgccc gaaggtcctc cggaggcccg gcattctgca    420
```

```
cgcttcaaaa gcgcacgtct gccgcgctgt tctcctcttc ctcatctccg ggcctttcga    480
cctg                                                                 484
```

<210> SEQ ID NO 25
<211> LENGTH: 612
<212> TYPE: DNA
<213> ORGANISM: Artificial Sequence
<220> FEATURE:
<223> OTHER INFORMATION: Puromycin Gene of Donor

<400> SEQUENCE: 25

```
cagcccaagc ttaccatgac cgagtacaag cccacggtgc gcctcgccac ccgcgacgac     60
gtccccaggg ccgtacgcac cctcgccgcc gcgttcgccg actacccngc cacgcgccac    120
accgtcgatc cggaccgcca catcgagcgg gtcaccgagc tgcaagaact cttcctcacg    180
cgcgtcgggc tcgacatcgg caaggtgtgg gtcgcggacg acggcgccgc ggtggcggtc    240
tggaccacgc cggagagcgt cgaagcgggg gcggtgttcg ccgagatcgg cccgcgcatg    300
gccgagttga gcggttcccg gctggccgcg cagcaacaga tggaaggcct cctggcgccg    360
caccggccca aggagcccgc gtggttcctg gccaccgtcg gcgtctcgcc cgaccaccag    420
ggcaagggtc tgggcagcgc cgtcgtgctc cccggagtgg aggcggccga gcgcgccggg    480
gtgcccgcct tcctggagac ctccgcgccc cgcaacctcc ccttctacga gcggctcggc    540
ttcaccgtca ccgccgacgt cgaggtgccc gaaggaccgc gcacctggtg catgacccgc    600
aagcccggtg cc                                                        612
```

<210> SEQ ID NO 26
<211> LENGTH: 295
<212> TYPE: DNA
<213> ORGANISM: Artificial Sequence
<220> FEATURE:
<223> OTHER INFORMATION: Bovine Growth Hormone polyadenylation signal of
      donor

<400> SEQUENCE: 26

```
catcatcacc atcaccattg agtttaaacc cgctgatcag cctcgactgt gccttctagt     60
tgccagccat ctgttgtttg cccctccccc gtgccttcct tgaccctgga aggtgccact    120
cccactgtcc tttcctaata aaatgaggaa attgcatcgc attgtctgag taggtgtcat    180
tctattctgg ggggtggggt ggggcaggac agcaaggggg aggattggga agacaatagc    240
aggcatgctg gggatgcggt gggctctatg gcttctgagg cggaaagaac cagct         295
```

<210> SEQ ID NO 27
<211> LENGTH: 34
<212> TYPE: DNA
<213> ORGANISM: Artificial Sequence
<220> FEATURE:
<223> OTHER INFORMATION: Loxp Site of Donor

<400> SEQUENCE: 27

```
ataacttcgt ataatgtatg ctatacgaag ttat                                 34
```

<210> SEQ ID NO 28
<211> LENGTH: 785
<212> TYPE: DNA
<213> ORGANISM: Artificial Sequence
<220> FEATURE:
<223> OTHER INFORMATION: Right Arm of Donor

<400> SEQUENCE: 28

```
ctcgagatcg tcccacatcc ctgtctcttt ctgacccctg cccacctacc ctgacttctc      60
tcttaggggt tgagcggacc ctggtgcttc ctgggagtca gacagcattc gacttggatg     120
acgttcaggc tgggcttagc tacactgtgc gggtgtctgc tagagtgggt ccccgtgagg     180
gcagcgctag cgtgctgacc gtccgccggg gtgagtactg caggaggctt gtggaggaca     240
gctgcctgcc tcactctggt cctggttctg acttctgact tctgtctgta actcctagag     300
ccggaaactc cacttgctgt tccagggctg cgggttgtgg tgtcagatgc aacgcgagtg     360
agggtggcct ggggacccgt ccctggagct agtggatttc ggattagctg agcacaggc     420
agtggtcagt gtggggtgtg tgggggactg ccaaagggac caatgagggt atgggtgcca     480
gaggggacag gcaggagcca tgccagcatt tccctctgac ctcaggtccg gagtccagcc     540
agacactgcc cccagactct actgccacag acatcacagg gctgcagcct ggaaccacct     600
accaggtggc tgtgtcggta ctgcgaggca gagaggaggg acctgctgca gtcatcgtgg     660
ctcgaacggg tcaggccctg cccccgtccc ttggctctct gcctccattg ctctttcaga     720
cccccatgcc ttcccttgca gacccttgct ctccccaga actcctgcct cccccttcag     780
aatcc                                                                785
```

```
<210> SEQ ID NO 29
<211> LENGTH: 3656
<212> TYPE: DNA
<213> ORGANISM: Artificial Sequence
<220> FEATURE:
<223> OTHER INFORMATION: TALEN Left
```

<400> SEQUENCE: 29

```
gatcccattc gtccgcgcag gccaagtcct gcccgcgagc ttctgcccgg accccaaccg      60
gatagggttc agccgactgc agatcgtggg gtgtctgcgc ctgctggcag ccctctggat     120
ggcttgcccg ctcggcggac ggtgtccgg accggctgc catctccccc tgcgccctca     180
cctgcgttct cggcgggcag cttcagcgat ctgctccgtc cgttcgatcc gtcgcttctt     240
gatacatcgc ttcttgattc gatgcctgcc gtcggcacgc cgcatacagc ggctgcccca     300
gcagagtggg atgaggcgca atcggctctg cgtgcagccg atgacccgcc acccaccgtg     360
cgtgtcgctg tcactgccgc gcggccgccg cgcgccaagc cggccccgcg acggcgtgct     420
gcgcaaccct ccgacgcttc gccggccgcg caggtggatc tacgcacgct cggctacagt     480
cagcagcagc aagagaagat caaaccgaag gtgcgttcga cagtggcgca gcaccacgag     540
gcactggtgg gccatgggtt tacacacgcg cacatcgttg cgctcagcca cacccggca     600
gcgttaggga ccgtcgctgt cacgtatcag cacataatca cggcgttgcc agaggcgaca     660
cacgaagaca tcgttggcgt cggcaaacag tggtccggcg cacgcgccct ggaggccttg     720
ctcacggatg cggggagtt gagaggtccg ccgttacagt tggacacagg ccaacttgtg     780
aagattgcaa acgtggcggc gtgaccgca atggaggcag tgcatgcatc gcgcaatgca     840
ctgacggtg ccccctgaa cctgacccg gaccaagtgg tggctatcgc cagcaacaag     900
ggcggcaagc aagcgctcga aacggtgcag cggctgttgc cggtgctgtg ccaggaccat     960
ggcctgactc cggaccaagt ggtggctatc gccagccacg atggcggcaa gcaagcgctc    1020
gaaacggtgc agcggctgtt gccggtgctg tgccaggaca tggcctgac tccggaccaa    1080
gtggtggcta tcgccagcca cgatggcggc aagcaagcgc tcgaaacggt gcagcggctg    1140
ttgccggtgc tgtgccagga ccatggcctg accccggacc aagtggtggc tatcgccagc    1200
```

-continued

```
aacattggcg gcaagcaagc gctcgaaacg gtgcagcggc tgttgccggt gctgtgccag    1260
gaccatggcc tgaccccgga ccaagtggtg gctatcgcca gcaacaaggg cggcaagcaa    1320
gcgctcgaaa cggtgcagcg gctgttgccg gtgctgtgcc aggaccatgg cctgaccccg    1380
gaccaagtgg tggctatcgc cagcaacggt ggcggcaagc aagcgctcga acggtgcag     1440
cggctgttgc cggtgctgtg ccaggaccat ggcctgaccc cggaccaagt ggtggctatc    1500
gccagcaaca agggcggcaa gcaagcgctc gaaacggtgc agcggctgtt gccggtgctg    1560
tgccaggacc atggcctgac cccggaccaa gtggtggcta tcgccagcaa cggtggcggc    1620
aagcaagcgc tcgaaacggt gcagcggctg ttgccggtgc tgtgccagga ccatggcctg    1680
actccggacc aagtggtggc tatcgccagc cacgatggcg gcaagcaagc gctcgaaacg    1740
gtgcagcggc tgttgccggt gctgtgccag gaccatggcc tgactccgga ccaagtggtg    1800
gctatcgcca gccacgatgg cggcaagcaa gcgctcgaaa cggtgcagcg gctgttgccg    1860
gtgctgtgcc aggaccatgg cctgaccccg gaccaagtgg tggctatcgc cagcaacggt    1920
ggcggcaagc aagcgctcga aacggtgcag cggctgttgc cggtgctgtg ccaggaccat    1980
ggcctgactc cggaccaagt ggtggctatc gccagccacg atggcggcaa gcaagcgctc    2040
gaaacggtgc agcggctgtt gccggtgctg tgccaggacc atggcctgac cccggaccaa    2100
gtggtggcta tcgccagcaa cattggcggc aagcaagcgc tcgaaacggt gcagcggctg    2160
ttgccggtgt tgtgccagga ccatggcctg actccggacc aagtggtggc tatcgccagc    2220
cacgatggcg gcaagcaagc gctcgaaacg gtgcagcggc tgttgccggt gctgtgccag    2280
gaccatggcc tgaccccgga ccaagtggtg gctatcgcca gcaacggtgg cggcaagcaa    2340
gcgctcgaaa gcattgtggc ccagctgagc cggcctgatc cggcgttggc cgcgttgacc    2400
aacgaccacc tcgtcgcctt ggcctgcctc ggcggacgtc ctgccatgga tgcagtgaaa    2460
aagggattgc cgcacgcgcc ggaattgatc agaagagtca atcgccgtat tggcgaacgc    2520
acgtcccatc gcgttgccga ctacgcgcaa gtggttcgcg tgctggagtt tttccagtgc    2580
cactcccacc cagcgtacgc atttgatgag gccatgacgc agttcgggat gagcaggaac    2640
gggttggtac agctctttcg cagagtgggc gtcaccgaac tcgaagcccg cggtggaacg    2700
ctccccccag cctcgcagcg ttgggaccgt atcctccagg catcagggat gaaaagggcc    2760
aaaccgtccc ctacttcagc tcaaacaccg gatcaggcgt cttttgcatgc attgccgat   2820
tcgctggagc gtgaccttga tgcgcccagc ccaatgcacg agggagatca gacgcgggca    2880
agcagccgta acggtcccg atcggatcgt gctgtcaccg gccctccgc acagcaggct     2940
gtcgaggtgc gcgttcccga acagcgcgat gcgctgcatt tgcccctcag ctggagggta    3000
aaacgcccgc gtaccaggat ctggggcggc ctcccggatc cgatatctag atcccagcta    3060
gtgaaatctg aattggaaga gaagaaatct gaacttagac ataaattgaa atatgtgcca    3120
catgaatata ttgaattgat tgaaatcgca agaaattcaa ctcaggatag aatccttgaa    3180
atgaaggtga tggagttctt tatgaaggtt tatggttatc gtggtaaaca tttgggtgga    3240
tcaaggaaac cagacggagc aatttatact gtcggatctc ctattgatta cggtgtgatc    3300
gttgatacta aggcatattc aggaggttat aatcttccaa ttggtcaagc agatgaaatg    3360
caaagatatg tcgaagagaa tcaaacaaga aacaagcata tcaaccctaa tgaatggtgg    3420
aaagtctatc catcttcagt aacagaattt aagttcttgt tgtgagtgg tcatttcaaa     3480
ggaaactaca aagctcagct tacaagattg aatcatatca ctaattgtaa tggagctgtt    3540
```
cttagtgtag aagagctttt gattggtgga gaaatgatta aagctggtac attgacactt    3600
gaggaagtga aaggaaatt taataacggt gagataaact tttaatagga gctcga    3656

<210> SEQ ID NO 30
<211> LENGTH: 3645
<212> TYPE: DNA
<213> ORGANISM: Artificial Sequence
<220> FEATURE:
<223> OTHER INFORMATION: TALEN Right

<400> SEQUENCE: 30
gatcccattc gtccgcgcag gccaagtcct gcccgcgagc ttctgcccgg accccaaccg    60 gataggggttc agccgactgc agatcgtggg gtgtctgcgc ctgctggcag ccctctggat    120
ggcttgcccg ctcggcggac ggtgtcccgg acccggctgc catctccccc tgcgccctca    180
cctgcgttct cggcgggcag cttcagcgat ctgctccgtc cgttcgatcc gtcgcttctt    240
gatacatcgc ttcttgattc gatgcctgcc gtcggcacgc cgcatacagc ggctgcccca    300
gcagagtggg atgaggcgca atcggctctg cgtgcagccg atgacccgcc acccaccgtg    360
cgtgtcgctg tcactgccgc gcggccgccg cgcgccaagc cggccccgcg acggcgtgct    420
gcgcaaccct ccgacgcttc gccggccgcg caggtggatc tacgcacgct cggctacagt    480
cagcagcagc aagagaagat caaaccgaag gtgcgttcga cagtggcgca gcaccacgag    540
gcactggtgg gccatgggtt tacacacgcg cacatcgttg cgctcagcca cacccggca    600 gcgttaggga ccgtcgctgt cacgtatcag cacataatca cggcgttgcc agaggcgaca    660
cacgaagaca tcgttggcgt cggcaaacag tggtccggcg cacgcgccct ggaggccttg    720
ctcacggatg cgggggagtt gagaggtccg ccgttacagt tggacacagg ccaacttgtg    780
aagattgcaa acgtggcgg cgtgaccgca atggaggcag tgcatgcatc gcgcaatgca    840
ctgacgggtg cccccctgaa cctgaccccg gaccaagtgg tggctatcgc cagcaacaag    900
ggcggcaagc aagcgctcga aacggtgcag cggctgttgc cggtgctgtg ccaggaccat    960
ggcctgaccc cggaccaagt ggtggctatc gccagcaacg gtggcggcaa gcaagcgctc    1020
gaaacggtgc agcggctgtt gccggtgctg tgccaggacc atggcctgac tccggaccaa    1080
gtggtggcta tcgccagcca cgatggcggc aagcaagcgc tcgaaacggt gcagcggctg    1140
ttgccggtgt gtgccagga ccatggcctg actccggacc aagtggtggc tatcgccagc    1200
cacgatggcg gcaagcaagc gctcgaaacg gtgcagcggc tgttgccggt gctgtgccag    1260
gaccatggcc tgaccccgga ccaagtggtg gctatcgcca gcaacggtgg cggcaagcaa    1320
gcgctcgaaa cggtgcagcg gctgttgccg gtgctgtgcc aggaccatgg cctgactccg    1380
gaccaagtgg tggctatcgc cagccacgat ggcggcaagc aagcgctcga acggtgcag    1440 cggctgttgc cggtgctgtg ccaggaccat ggcctgactc cggaccaagt ggtggctatc    1500
gccagccacg atggcggcaa gcaagcgctc gaaacggtgc agcggctgtt gccggtgctg    1560
tgccaggacc atggcctgac cccggaccaa gtggtggcta tcgccagcaa cattggcggc    1620
aagcaagcgc tcgaaacggt gcagcggctg ttgccggtgc tgtgccagga ccatggcctg    1680
actccggacc aagtggtggc tatcgccagc cacgatggcg gcaagcaagc gctcgaaacg    1740
gtgcagcggc tgttgccggt gctgtgccag gaccatggcc tgaccccgga ccaagtggtg    1800
gctatcgcca gcaacattgg cggcaagcaa gcgctcgaaa cggtgcagcg gctgttgccg    1860
gtgctgtgcc aggaccatgg cctgaccccg gaccaagtgg tggctatcgc cagcaacatt    1920
ggcggcaagc aagcgctcga aacggtgcag cggctgttgc cggtgctgtg ccaggaccat    1980

-continued

| | |
|---|---|
| ggcctgaccc cggaccaagt ggtggctatc gccagcaaca agggcggcaa gcaagcgctc | 2040 |
| gaaacggtgc agcggctgtt gccggtgctg tgccaggacc atggcctgac tccggaccaa | 2100 |
| gtggtggcta tcgccagcca cgatggcggc aagcaagcgc tcgaaacggt gcagcggctg | 2160 |
| ttgccggtgc tgtgccagga ccatggcctg actccggacc aagtggtggc tatcgccagc | 2220 |
| cacgatggcg gcaagcaagc gctcgaaacg gtgcagcggc tgttgccggt gctgtgccag | 2280 |
| gaccatggcc tgaccccgga ccaagtggtg gctatcgcca gcaacggtgg cggcaagcaa | 2340 |
| gcgctcgaaa gcattgtggc cagctgagcg ggcctgatcc ggcgttggcg cgcgttgacc | 2400 |
| aacgaccacc tcgtcgcctt ggcctgcctc ggcggacgtc ctgccatgga tgcagtgaaa | 2460 |
| aagggattgc cgcacgcgcc ggaattgatc agaagagtca atcgccgtat tggcgaacgc | 2520 |
| acgtcccatc gcgttgccga ctacgcgcaa gtggttcgcg tgctggagtt tttccagtgc | 2580 |
| cactcccacc cagcgtacgc atttgatgag gccatgacgc agttcgggat gagcaggaac | 2640 |
| gggttggtac agctctttcg cagagtgggc gtcaccgaac tcgaagcccg cggtggaacg | 2700 |
| ctcccccccag cctcgcagcg ttgggaccgt atcctccagg catcagggat gaaaagggcc | 2760 |
| aaaccgtccc ctacttcagc tcaaacaccg gatcaggcgt ctttgcatgc attcgccgat | 2820 |
| tcgctggagc gtgaccttga tgcgcccagc ccaatgcacg agggagatca gacgcgggca | 2880 |
| agcagccgta acggtcccg atcggatcgt gctgtcaccg gcccctccgc acagcaggct | 2940 |
| gtcgaggtgc gcgttcccga acagcgcgat gcgctgcatt tgcccctcag ctggagggta | 3000 |
| aaacgcccgc gtaccaggat ctggggcggc ctcccggatc cgatatctag atcccagcta | 3060 |
| gtgaaatctg aattggaaga aagaaatct gaacttagac ataaattgaa atatgtgcca | 3120 |
| catgaatata ttgaattgat tgaaatcgca agaaattcaa ctcaggatag aatccttgaa | 3180 |
| atgaaggtga tggagttctt tatgaaggtt tatggttatc gtggtaaaca tttgggtgga | 3240 |
| tcaaggaaac cagacggagc aatttatact gtcggatctc ctattgatta cggtgtgatc | 3300 |
| gttgatacta aggcatattc aggaggttat aatcttccaa ttggtcaagc agatgaaatg | 3360 |
| caaagatatg tcgaagagaa tcaaacaaga acaagcata tcaaccctaa tgaatggtgg | 3420 |
| aaagtctatc catcttcagt aacagaattt aagttcttgt tgtgagtgg tcatttcaaa | 3480 |
| ggaaactaca agctcagct tacaagattg aatcatatca ctaattgtaa tggagctgtt | 3540 |
| cttagtgtag aagagctttt gattggtgga gaaatgatta agctggtac attgacactt | 3600 |
| gaggaagtga aaggaaatt taataacggt gagataaact tttaa | 3645 |

<210> SEQ ID NO 31
<211> LENGTH: 706
<212> TYPE: DNA
<213> ORGANISM: Artificial Sequence
<220> FEATURE:
<223> OTHER INFORMATION: Left Am of Donor

<400> SEQUENCE: 31

| | |
|---|---|
| gcctgtgagc cctgtaacag acctgcaagc caccgagctg cccgggcagc gggtgcgagt | 60 |
| gtcctggagc ccagtccctg gtgccaccca gtaccgcatc attgtgcgca gcacccaggg | 120 |
| tgaggtggac gcagccagca cccccaccac acacactgaa gttccagcct gaggggtctg | 180 |
| agtgtacctc cagccctctc cttccacacc tgggtcccta gtctcctc cctgtctcgt | 240 |
| tatccatctg cttcccaaga tggcactgag ccctgaactg tcaacagggt gtgtctgccc | 300 |
| ctaccctacc ccaaccaatc tcctccctgc cccacacccc atcacggct tcacctctg | 360 |
| cacagccaca agctcaatca cctgtctttc tgttacccta gtggtgacca ctgtacacca | 420 |

-continued

| | |
|---|---|
| acctctcatt gcatgtcccc atccagcact gacctctgcc atcccacatc agtgtctgtc | 480 |
| aatggctcat cagttctcac tgcagtccac tgactcctgt catcctacat gctaagatcc | 540 |
| cacagactcc tgtcctccag tgtccctgac catcactggc ccctttcatc ctatgtcctt | 600 |
| gtcttgcact cactttttc agccatatcc cagctctctg gtccccacca ccccacatcc | 660 |
| ccaccccat ggcccttctc actctgcgtc cctgtccatc actgcc | 706 |

<210> SEQ ID NO 32
<211> LENGTH: 32395
<212> TYPE: DNA
<213> ORGANISM: Homo sapiens

<400> SEQUENCE: 32

| | |
|---|---|
| agaggggtg agttacttgg atccaggcca aggggacctt ggtttcccta agaccggccc | 60 |
| agagtcactc atttgccagg gcttcttgcc tgtcaaggag atccgggtgg ggcccaggag | 120 |
| gcccaccaga cagatggctg aatcacagga gtggccggcg ggacccatgg cctgagggct | 180 |
| tgtctgggca cccccactgg attggggtg agtcatcccc aactgcagcc caccccca | 240 |
| cggcgctgct gccttgtggc tctgcaggaa cctgtccact cctcagcctg gtcactgtga | 300 |
| ttgacctaaa gcagccaaga cctgtgacct tagatggagt taggggtact ccctcagcat | 360 |
| ctgcccatgc agaaccttct gggaaattcc cagaagccac ggggggtcgg ggggttata | 420 |
| gttaagtgcg tcatatcgtt tgtctggggg aggggtgggg gggcggcga cctctcaggg | 480 |
| atatgggtga gggcgggtgc ctgggttccc gcctgccgct ccgcccccg agatcaggga | 540 |
| ctttctctg ctctgcccga gagactgcag cggcggcggc gggagcgggc ggacgcgcag | 600 |
| gcaagaccag gactcgggct ggagggggcgc tgggctcgga cctgccaagg ccacggggga | 660 |
| gcaagggaca gaggcggggg tcctagctga cggcttttac tgcctaggat gacgctgcgg | 720 |
| cttctggtgg ccgcgctctg cgccgggatc ctggcagagg cgccccgagt gcgagcccag | 780 |
| cacagggaga gaggtgggca ccgcaaggga ggacccggcc cggggcactg caccgtgcca | 840 |
| ccctccgctc cactcggcct tcatccccaa caccccccgc ccacaaccca gccaactcca | 900 |
| cgacgccccg cggattcctc ctaattctgg gactccccga accctccgcg atcggtgctg | 960 |
| ggttccctaa accgcctcct atcctgttcc tacccaaatt ctggctccct ggatgcgtgc | 1020 |
| ggggtcccct gccttatgcc aatccacgcc ggccctaga ggctgacctc agtcccaagt | 1080 |
| ccacacccgt gctggcgact ctccctcccc cgcacacccc caaccctccg cgggagtctg | 1140 |
| ctctgggacc caccgagctc aactcctcc aaggccctca ggctcaggcc gattcggccc | 1200 |
| tggtttgcat aagatgaggc ctactctccc caccatccca agtcccagtg aggccaccgt | 1260 |
| gcgggtaggc gggtggttgg cctcccagaa gaggccctga tctctcctgc ccgccccagt | 1320 |
| gacctgcacg cgcctttacg ccgctgacat tgtgttctta ctggatggct cctcatccat | 1380 |
| tggccgcagc aatttccgcg aggtccgcag ctttctcgaa gggctggtgc tgcctttctc | 1440 |
| tggagcagcc agtgcacagg gtgtgcgctt gccacagtg cagtacagcg atgacccacg | 1500 |
| gtgagtaggg gcctgggggg ctggggacca cgagatcccc accaagactc cttccccaga | 1560 |
| gagggaggag accctggaaa ccccaggcca ggtctttgca gaaacaagtt ttggggaacc | 1620 |
| tagagacccc ctagccagga cctcctttgg agacagaggt aaggattccc taggtagaac | 1680 |
| cttcgtgccc tgaggcacct ccaggctact gcaagacagg aaggtgcaag acagtgaggc | 1740 |
| tgtgttttct gatctggaga tggggagccc aggaggggc ccccacgcct gttggattct | 1800 |
| ccacgttcta gccctctaac ccttgcagcc gttcaccaga ggtgctccat ctggccagca | 1860 |

-continued

```
tccactttcc tacatctgga cccctcctcc tgcaattatt taattaagca gcatcttgtt      1920
ccccacagac tgtgagcccc taagggctcc ttcaggtctg cccaggccca cctgcagatg      1980
gtgcacaaag agcccctggg ggagtttgtt aacctggggg ttccagaggc aagtgggtgt      2040
ggagaatgac agaacgaagg gaccccctcaa gagagcctga tacccgtaac cctcacccta     2100
gaggcctcct caaggccagg gccagaagag atcctgagtc ctagcctgtt gccaccccta      2160
ccctccaaca ggacagagtt cggcctggat gcacttggct ctgggggtga tgtgatccgc      2220
gccatccgtg agcttagcta caaggggggc aacactcgca caggggctgc aattctccat      2280
gtggctgacc atgtcttcct gcccagctg gcccgacctg tgtcccaa ggtgatccct         2340 accccctacca tgcctcccaa gatgacccca aatgaagtgt ccaggggaac cgtgatttga    2400 ccctgcacc tgtcccaggt ctgcatcctg atcacagacg ggaagtccca ggacctggtg     2460
gacacagctg cccaaaggct gaaggggcag gggtcaagc tatttgctgt gggtaaggac     2520
cgagcaggag tgacaggtca gctgggggt gggggcagtc agagagcatg tgggtgactg     2580
agtcctgatg ggtcgtcact tcaggggatca agaatgctga ccctgaggag ctgaagcgag  2640
ttgcctcaca gcccaccagt gacttcttct tcttcgtcaa tgacttcagc atcttgagga    2700
cactactgcc cctcgtttcc cggagagtgt gcacgactgc tggtggcgtg cctgtgaccc    2760
gacctcgtga gttcctgccc acacggtgta ccctgaccta gccccggac cccaatcccc     2820 acttggcagt gctgattcca tcctatgtgc tcctgacccc gaccccaact ctgcatcata    2880
catgcccacc ccaatcctcc tgcctgatcc cctgatcccg cattcccagc ggatgactcg    2940
acctctgctc cacgagacct ggtgctgtct gagccaagca gccaatcctt gagagtacag    3000
tggacagcgg ccagtggccc tgtgactggc tacaaggtcc agtacactcc tctgacgggg    3060
ctgggacagc cactgccgag tgagcggcag gaggtaggat gtcaggagtg ataggtggtg    3120
gctggggact tggctgggca agataaagtg acctcttgcc ctgggcaggt gaacgtccca    3180
gctggtgaga ccagtgtgcg gctgcggggt ctccggccac tgaccgagta ccaagtgact    3240
gtgattgccc tctacgccaa cagcatcggg gaggctgtga gcgggacagc tcggaccagt    3300
gagcaattct gccagcctct gaccccattc acctaacccc cgaccccagt acccctccc     3360 acttctgact ccatgaatcc ctggtgggac tctcccccag ctgccctaga agggccggaa    3420
ctgaccatcc agaataccac agcccacagc ctcctggtgg cctggcggag tgtgccaggt    3480
gccactggct accgtgtgac atggcgggtc ctcagtggtg agtgagagat gtgggctgag    3540
gggagtcccc gcgcctcaga caaggctgta gagtcctgag tctgcaaggc ccactggccc    3600
cttggtgtcc cccatgcagg tgggcccaca cagcagcagg agctgggccc tgggcagggt    3660
tcagtgttgc tgcgtgactt ggagcctggc acggactatg aggtgaccgt gagcacccta    3720
tttggccgca gtgtggggcc cgccacttcc ctgatggctc gcactggtga aaggctggg     3780 cactttcttc aggctgggac gggcaggcag ggcaaggccc ggaggccact gacatcccat    3840
gtgccctggg cagacgcttc tgttgagcag acctgcgcc cggtcatcct gggccccaca    3900
tccatcctcc tttcctggaa cttggtgcct gaggcccgtg gctaccggtt ggaatggcgg    3960
cgtgagactg gtcagtgcgg gggaagggat ggacaggcaa gggtcagggc atggcctctg    4020
ctggtctgac cctgttatct tgcaggcttg gagccaccgc agaaggtggt actgccctct    4080
gatgtgaccc gctaccagtt ggatgggctg cagccgggca ctgagtaccg cctcacactc    4140
tacactctgc tggagggcca cgaggtgcc acccctgcaa ccgtggttcc cactggtgag    4200
ggctctgtgg gctgggccag tgagtggggg aggtgtcgga gccccaggct gcctctatgc    4260
```

```
tgtgctctcc aacaggacca gagctgcctg tgagccctgt aacagacctg caagccaccg    4320
agctgcccgg gcagcgggtg cgagtgtcct ggagcccagt ccctggtgcc acccagtacc    4380
gcatcattgt gcgcagcacc cagggtgagg tggacgcagc cagcaccccc accacacaca    4440
ctgaagttcc agcctgaggg gtctgagtgt acctccagcc ctctccttcc acacctgggt    4500
ccctatagtc tcctccctgt ctcgttatcc atctgcttcc caagatggca ctgagccctg    4560
aactgtcaac agggtgtgtc tgcccctacc ctaccccaac caatctcctc cctgcccac     4620 accccatcca cggctttcac ctctgcacag ccacaagctc aatcacctgt ctttctgtta    4680
ccctagtggt gaccactgta caccaacctc tcattgcatg tccccatcca gcactgacct    4740
ctgccatccc acatcagtgt ctgtcaatgg ctcatcagtt ctcactgcag tccactgact    4800
cctgtcatcc tacatgctaa gatcccacag actcctgtcc tccagtgtcc ctgaccatca    4860
ctggcccctt tcatcctatg tccttgtctt gcactcactt ttttcagcca tatcccagct    4920
ctctggtccc caccacccca catccccacc cccatggccc ttctcactct gcgtccctgt    4980
ccatcactgc catcgtccca catccctgtc tctttctgac ccctgcccac ctaccctgac    5040
ttctctctta ggggttgagc ggaccctggt gcttcctggg agtcagacag cattcgactt    5100
ggatgacgtt caggctgggc ttagctacac tgtgcgggtg tctgctcgag tgggtccccg    5160
tgagggcagt gccagtgtcc tcactgtccg ccggggtgag tactgcagga ggcttgtgga    5220
ggacagctgc ctgcctcact ctggtcctgg ttctgacttc tgacttctgt ctgtaactcc    5280
tagagccgga aactccactt gctgttccag ggctgcgggt tgtggtgtca gatgcaacgc    5340
gagtgagggt ggcctgggga cccgtccctg gagccagtgg atttcggatt agctggagca    5400
caggcagtgg tcagtgtggg gtgtgtgggg ggactgccaa agggaccaat gagggtatgg    5460
gtgccagagg ggacaggcag gagccatgcc agcatttccc tctgacctca ggtccggagt    5520
ccagccagac actgccccca gactctactg ccacagacat cacagggctg cagcctggaa    5580
ccacctacca ggtggctgtg tcggtactgc gaggcagaga ggagggccct gctgcagtca    5640
tcgtggctcg aacgggtcag gccctgcccc cgtcccttgg ctctctgcct ccattgctct    5700
ttcagacccc catgccttcc cttgcagacc cttgcttctc cccagaactc ctgcctcccc    5760
cttcagaatc ccactccctc ctccctcaga gacgctgctt cctcttcagt ttcagctgtc    5820
tccccttaag ccctccccgt attcagattc tccgcttcct ctcctaagac tcccacagcc    5880
tttgccctca aatatccacc acttcaaccc tcagacccc atccttttt tgctggaccc     5940 aaatctcctc tgagatttac actttctcct ccatcagacc tgctcactgc ttcctaaaac    6000
ctccacctcc ccactcctcc actggaccta ttcaccatct cctctatcaa attcccgtct    6060
cctgttagac tccatcatc ttcccctatc agatagcccc actccttcct gcctgttcca     6120
gcagactccc cattgcctct ccccactaga ccactgggc ccagtgagga cggtccatgt     6180
gactcaggcc agcagctcat ctgtcaccat tacctggacc agggttcctg gcgccacagg    6240
atacagggtt tcctggcact cagcccacgg tggggactgg ggtttgggag ggggcaggtc    6300
agggtggaat gggggctggg ggtttattgg gggtccaggt ggggctctgg ggcacagagt    6360
ttgctagccc tggagctgcc tccatccctg ttcccaggcc cagagaaatc ccagttggtt    6420
tctggggagg ccacggtggc tgagctggat ggactggagc cagatactga gtatacggtg    6480
catgtgaggg cccatgtggc tggcgtggat gggcccctg cctctgtggt tgtgaggact     6540
ggtgagtgga ccctggccag ctactagcca caccgcatta gctaccctgc cctgctgtgt    6600
gttcctgatt gcccagctgc ctccacccc ctgctcagtg actgtcctgt ccacactgac     6660
```

```
ccaccccaca ctgattaagt gtccacccac ggtgacctcc tggtggcccc acactgccca    6720
ccccaaggca ctgacctcct cctcctcagg gctgcctaaa gtgacctgtc cacactaacc    6780
tcacactgac tttcagatca cccctgcgtc aaccattcct gcactgcctc tctgttctct    6840
accaggaccc cttaccttgc ctctgtcccc agccctgag cctgtgggtc gtgtgtcgag     6900
gctgcagatc ctcaatgctt ccagcgacgt tctacggatc acctgggtag gggtcactgg    6960
agccacagct tacagactgg cctggggccg gagtgaaggt atggctccct gacgccaccc    7020
ctgtccttcc tggctgggac tgctcacccc taaccattgc tgtatgccca cctggccagg    7080
cggccccatg aggcaccaga tactcccagg aaacacagac tctgcagaga tccgggtct    7140 cgaaggtgga gtcagctact cagtgcgagt gactgcactt gtcggggacc gcgagggcac    7200
acctgtctcc attgttgtca ctacgcgtag gcagagcatg cgctggagag cttcggatgg    7260
gtggtgtgga tggtttgggg atccgggctt gtgctctgga ttggagaaag gaccaggatt    7320
ggtagtgagc ctttggggc agggtctgag aggagggaga ggggtctgag aggctgggcg    7380
gggtgcgtgt gccagggtgg gcctgggatt ggtgcagggg ccatgggggc agagcctccc    7440
tgattcctga gctttctctc cagcgcctga ggctccgcca gccctgggga cgcttcacgt    7500
ggtgcagcgc ggggagcact cgctgaggct gcgctgggag ccggtgccca gagcgcaggg    7560
cttccttctg cactggcaac ctgagggtga gaggtgtccc caggaggaag ttagggacca    7620 ttggggggcag ggctgtggca gactccgcaa ggtaggcgag gacagtgatg gtgggcgggg   7680
tctgtcactg ggggtctgcg ggatccgtga cagtaggtaa gatcaatcaa tgaagtgggt    7740
gggatcaatg agttcatgga gggtcagtct ggcagggtcc gtaaagtggg cagggtcagt    7800
gaggatgagg aagatcagtc aggagggtga acccagttaa cagagccagt gaagtgggca    7860
ggccctttaa tgcccccagg tgtcactatc ccacatgctc ttggcccccca ccctcacgcc    7920 tgccccaggt ggccaggaac agtcccgggt cctggggccc gagctcagca gctatcacct    7980
ggacgggctg gagccagcga cacagtaccg cgtgaggctg agtgtcctag gccagctgg    8040 agaagggccc tctgcagagg tgactgcgcg cactggtaag cctgcctcac cttggcgtgc    8100 tcctccctg ctgatgaccc accctgactt cctgcacccc gactctgagt gactcctcct    8160 gtaccctac ccctcaccct ctgaccctgg gtgacccag catgacctcc catgatgctt      8220
caataagaca aaccggaccc aggatctcag atctctccct tctgggttct caggactcag    8280
cctctgatcc tcgatctttc attcctcctt cagagtcacc tcgtgttcca agcattgaac    8340
tacgtgtggt ggacacctcg atcgactcgg tgactttggc ctggactcca gtgtccaggg    8400
catccagcta catcctatcc tggcggccac tcagaggccc tggccagggt gaggggagg     8460 ccaggatttg ggtgggctgg cagttggggc tctgtggaga cagcttttta atcaagttct    8520
gtctcctgca gaagtgcctg ggtccccgca gacacttcca gggatctcaa gctcccagcg    8580
ggtgacaggg ctagagcctg gcgtctctta catcttctcc ctgacgcctg tcctggatgg    8640
tgtgcggggt cctgaggcat ctgtcacaca gacgccaggt atagtgggcg tagtgggaag    8700
ggcagaaagg tgtgtctggg tgggctgccc gcttcagtaa cttgttcccc ttcctacagt    8760 gtgccccgt ggcctggcgg atgtggtgtt cctaccacat gccactcaag acaatgctca     8820
ccgtgcggag gctacgagga gggtcctgga gcgtctggtg ttggcacttg gcctcttgg     8880 gccacaggca gttcaggttt ggccctgggg cagccagatt ctacctctcc ctgaggcccc    8940
ccacccaggc tccataccag ttaccatctc ctgaccaccc aataggttca ggcattctcc    9000
cagctctctc acaggctcca gacctcacct actgcctggc tccctatcct gccatcactg    9060
```

```
ctgactccct aatagatagg gtttggtcac acacaccctg atgtgtttct ccaggctctg    9120
tgcaccccca tccctgctct gtcatcctcc tcaggctctg tgtttccttc caccccaggt    9180
tggcctgctg tcttacagtc atcggccctc cccactgttc ccactgaatg gctcccatga    9240
ccttggcatt atcttgcaaa ggatccgtga catgccctac atggacccaa gtgggaacaa    9300
cctgggtgag gactgcagca ggcatggact cctggggcta tccactggga gcttggtgcc    9360
ccagggttct gacatgtcct tccttccagg cacagccgtg gtcacagctc acagatacat    9420
gttggcacca gatgctcctg gcgccgcca gcacgtacca ggggtgatgg ttctgctagt    9480
ggatgaaccc ttgagaggtg acatattcag ccccatccgt gaggcccagg cttctggtaa    9540
ggagtaggct gatggggaag gggtctggga ataggggtgg ccctgaaaag gctatcatgc    9600
agccactgga ccccaccttA gggcttaatg tggtgatgtt gggaatggct ggagcggacc    9660
cagagcagct gcgtcgcttg gcgccgggta tggactctgt ccagaccttc ttcgccgtgg    9720
atgatgggcc aagcctggac caggcagtca gtggtctggc cacagccctg tgtcaggcat    9780
ccttcactac tcaggtttgg aagaggcctc tgggggactg ggtggtagaa tataaggggt    9840
ctggggttc ttggtagaaa tgttcaacct caaagagacc ctatgtccgc agccccggcc    9900
agagccctgc ccagtgtatt gtccaaaggt aagagtccct catcgagagg tgaacagagg    9960
ctgcacctgg ggctagccac tctgacccac atctgacatg tctttcccca gggccagaag   10020
ggggaacctg gagagatggt gagtgcccct gcgggcgggg aatagagaat gggttgagtg   10080
tcagtggggc aggagaggtt ggcagcacag gtctcactga ttacccttcc tagggcctga   10140
gaggacaagt tgggcctcct ggcgaccctg gcctcccgt gagtgtcccc cacatctgtc   10200
cctgcaccct gactggctta tccccaccta actgctatct tctttcaggg caggaccggt   10260
gctcccggcc cccaggggcc ccctggaagt gccactgcca agggcgagag ggtgagtgtg   10320
gagaccatcg aggtttctct gaggcactcc tcaaagctgt ctcggggttt ttacaagaga   10380
gaaggaagaa gcagagttag aatcatcggg aattcctaga agcccagctg gaggttataa   10440
accaccacag agactttggg ggacactctg aaatagaagg gccagtgggg cctctagccc   10500
cgctgcagag cctgagcagc agctccaagt cccagaggca gggaagccct ctgccttgtc   10560
gctgcccttg tgcctggaat tgggctctgt gaagctctga ggggccattt ctctgcctca   10620
ctgttccacc cccaataaca cttggggtc agtggggtag gcgacccctt gttgatgggg   10680
tgaggcccct ccagcaaacc aggggccttg ggggagggtc ccttcctgtc ctgacctctt   10740
cacctcctca gggcttccct ggagcagatg ggcgtccagg cagccctggc cgcgccggga   10800
atcctgggac ccctggagcc cctggcctaa aggtgagcaa gccttgtcct gcaggtcagg   10860
gtgggcgctg cctgagtggg tggggtggct ccgactgttc tgcctctggc tccatttgc   10920
agggctctcc agggttgcct ggccctcgtg gggacccggt aaggtgcctt cccttctttg   10980
ctctctaagt gtcttcccag ggttcttcca caggtgggA gcctggggtg gtggtgcagt   11040
gcccacgttg acattcgcct gagcccaagc accaccctct gctctgtttc gtcctcaggg   11100
agagcgagga cctcgaggcc caaggggga ccggtaggt gaaggggga gggaggcggc   11160
cgggatgtcc cagggaggag caggactgcc ccacaccaga ccctgtgcag gcctaaggc   11220
gcgaatagga ataggctggac atgtctaggg gcttcttcca gctcaaggcc cccatagcct   11280
gaatcctgcc cactgctctc tgtccttaca ggggctcccc ggacaagtca tcggaggtga   11340
aggacctggg cttcctgggc ggaaagggga ccctggacca tcggtaagtg caggGtatgt   11400
ggaggcaagt gatgtgtagt ggggggacca acacgagggg ggcgagagtg aggtctgtgg   11460
```

-continued

```
ggttgcacct tatactttgt ctcctccatc agggcccccc tggacctcgt ggaccactgg   11520
gggacccagg accccgtggc ccccagggc ttcctggaac agccatgaag gtgacagcct   11580
catgagtgcc atgtgatgca gagacctggt gaccccattt gaacccacat aaccccgcc   11640 agttactctg gcccttgtga ccctttgatt accccatcc tcaccatgac gcctcagttc   11700
tcccaaaatc cttgaaatcc aattggaccc catgaccctc atcactcctg gtatctttgg   11760
gagtgaggtg tggcccaggg tcatggggtc gtcatctgtt ttctagggtg acaaaggcga   11820
tcgtggggag cgggtaagtg agggacaggt tgtgctaggg gtggcttgga gtctgattcc   11880
cctgttcatt ccctgacctg ctgttctctc ccagggtccc cctggaccag gtgaaggtgg   11940
cattgctcct ggggagcctg ggctgccggt gaggggcctt gaggctctgc tgggggccct   12000
gctcaggggt gtgggtctct cctggggcag tggttgggtg ctgggcttca tagttcttgg   12060
ctcatatttt tactcacttc ttcctagggt cttcccggaa gccctggacc caaggcccc   12120 gttggccccc ctggaaagaa aggagaaaaa gtaggaaggc tgacttgatg atgtcccagt   12180
tctggggtgg gaggctgcgt gctggggca gggcctccct tcggtcttcc cacccgtgtg   12240
tttctccttc agggtgactc tgaggatgga gctccaggcc tcccaggaca acctgggtct   12300
ccgggtgagc aggtgagtgg aggggccagg gattctgaat atggtgggca cagctccagc   12360
ccctacctca atcatcaacc actgctccat cctcatgccc aaacccaaat ctctgaaccc   12420
ccaaattcat cccttccagg gcccacgggg acctcctgga gctattggcc caaagtgag   12480 taccagttgg gggattcagg tgtgaggggt gctactctgg gctccccatg gtgttagggg   12540
aggctggaag ataaggagat aagagttccc tccaggtcag aggtcgtggt tttggagggg   12600
gtggttggag tttgggaccc cttgtctggg gtttgacgtt caagcccgc caccaaccct   12660 ctctctctct gtctttctct cacctctctc cttcagggtg accggggctt tccagggccc   12720
ctgggtgagg ctggagagaa ggtaagtgca acctgggggg tgccaagggc cctggaggat   12780
ctgggcccaa ctcagctctg acctcttctt ttccatcagg gcgaacgtgg acccccaggc   12840
ccagcgggat cccgggtaaa cccactggct gcaatgctca taccagctga cctggctgtg   12900 cccttttctgg ttctgacttc ttgcccttga ccctgctac ccctgctcct cacccctcct   12960
caatgaccac ttatccctgc tgatacaggc tctaaccctc agccccaggg acctggcttt   13020
gaacctctga ccctgctgaa ctgaccttga ttttcactga cctggtctct gttcctgc   13080 caagtcttac ccctgccaac ctaaatccca atcttccctg accctctcc agccccacc   13140 ccagcctcta gccctgtctg tccatatccc ccgtccccac ccacctgcac agctcttccc   13200
ttcctctcct ccagggctg ccaggggttg ctggacgtcc tggagccaag ggtcctgaag   13260
tgagtctgtg actgtggtgg gaccaggagt gggactttttg tgtgtccctc cccttcccct   13320
tcccctcctg ggctcacact ttctctacat tcagggggcca ccaggaccca ctggccgcca   13380
aggagagaag gtgggtcctc ggctgggggt ggcactgtct ggtactaggg atgtggcaga   13440
tgggacactg ggattttggg ctcctaggtg actccctgac ctgtccctgc tcctatcctc   13500
tctccacagg gggagcctgg tcgccctggg gaccctgcag tggtggtgag tgacgggagg   13560
atggcgctct gagcacagca cagccctttga gcagtgaccc tcctatagaa cactatctgg   13620
gctgtgattc cacagtgctg ggcccgtgag caggctggga gctctgcggc tctccttctg   13680
ctagaacctg cccccagact cttggctatg atcctgtgac cccaagaccg ccatgcaggt   13740
catgagctct ttgtgtcagt ccatttttgta taacccccttc cctgctgtca gcggtgactc   13800
tgtgacttct gggcggggac tgagctgtat gacttccaat tccatgtgac ctccattcca   13860
```

-continued

```
atgaagactt tgatcataca accccaaggc agggccaagc tgtatctgtc ctgtttgttt    13920
tcagggacct gctgttgctg gacccaaagg agaaaaggta agcctggtat ggggcaaggg    13980
gaggtttcta cagggttgag gtctaggtca tagggcctat ctatgggact tgggggtca     14040 caggacttgc tgggtcaggg ggttaactgg agcctgggac tagcactgat ggtctttgtc    14100
acctccaggg agatgtgggg cccgctgggc ccagaggagc taccggagtc caaggggaac    14160
gggtaagtga agcgaagtgt ttaggggca gttggtgaag gttgtcttcc tgacttctta     14220
tccttccatc cacagggccc accggcttg gttcttcctg agaccctggg ccccaaggga     14280
gaccctggag accgggtgaa tcaatgtggg aatgggagt gtgacagagg gagatgaggt     14340
ggtgggaccc tgactaagtc ctgccccct tctgtcccct tcagggtccc attggcctta     14400
ctggcagagc aggaccccca gtgagtaccc gttaccctgg gcaacctcaa ggcttctggg    14460
gtccccctcc cttgagaact gcttgcttcg agcgtcctgc atcacctccc tcttgcctcc    14520
tccacagggt gactcagggc ctcctggaga gaagggagac cctgggcggc ctggcccccc    14580
aggacctgtt ggcccccgag gacgagatgt aagaggctgg agtcggggga gtcatggcgg    14640
gtaagggagt agggctgttg ccagcatcat ggggggttctt ggaaccaggg ctgactctca   14700
tgtttcacag ggtgaagttg gagagaaagg tgacgagggt cctccggtga gactccttcc    14760
cactgtggtt tctgatcctt tacccttgaa ctaggatccc agtaggctgg tgctccacca    14820
gttcatccat ccactccctg cctcctgtcc agctgctgct cagacccttc tctgtccct     14880 ctccctgagt gagttagatc ctgactgccc tgtgcagtat gacttttctc tctatcacca    14940
gggtgacccg ggtttgcctg gaaaagcagg cgagcgtggc cttcgggtga gtcttggcag    15000
agagaagtaa cagggggtgat gggaggtggg catgaaggtg ataggaaagg ctgaggggg     15060 taaggggtga tgggagtccc tgcagggagg catgggtga tgggaacctc tgatgtggat     15120
tttggagtaa tggggaacct ggggcagtgt agcgggtcat aggggcacct gcaaaatatt    15180
gggagggtct gtctcaggcc agctgctctt cttaggggc acctggagtt cgggggcctg     15240
tgggtgaaaa gggagaccag ggagatcctg gagaggatgg acgaaatgtg agtcccagcc    15300
tatgactcct caccccaacc ttaaccctcc aaccagccaa ttcccaatac ctgatcctac    15360
cccccaaccc tgtaatgcta aaccctccca atcttcactt cctttgaccc ctgcacacac    15420
gcatctgaag gctaccaaca ttcccatgag tcctcatggt gcttccaaag ctctcccaaa    15480
ctgctgccta ccttgagtgg ccctgacccc tgcctttctg cagggcagcc ctggatcatc    15540
tggacccaag ggtgaccgtg gggagccggt gagtagggct ggtgtcctgg gctcagaagg    15600
gatggagggt cccctggcgc tgctgccagt gtgccttcac acaaggggtc tggaggtcca    15660
ggtgggaagc atggatggcc acccatgcct gctgggggct ggcattgggg tgcttcgggg    15720
aacttggggg cagagttgag cctggggcaa accagagcca tggcctggga cctgagggct    15780
cctattgact ataatcattt cctttcccag ggtcccccag gaccccggg acggctggta     15840 agggctgcgc tgggtctggt cctctgtcat tgttctcact tgccccttg gctccacatc     15900 atgtcccctc attccttcca ctaactccca cttcccccac tgtccctctg aaacctccgc    15960
ggatccctgg agccctcac agaccctgta tccctcgcc aactcctctt cccccttgttg     16020 agccattctt ctcactggtc attcccccca caggtagaca caggacctgg agccagagag    16080
aaggtattag ggtctgtggg tggagggtaa gaaagacccc agtgcccctc ccagcaggtt    16140
ctaccttggg catggcttgg cttcaaggct gttcctcagc aagcttatct ctgccacagg    16200
gagagcctgg ggaccgcgga caagagggtc ctcgagggcc caagggtgat cctggcctcc    16260
```

```
ctggagcccc tggggaaagg gtgagtgtga ttggtcctcg ggggtgcagg catgggaggg   16320
cctgctctga tttcttcctc ccctatcctc agggcattga agggtttcgg ggacccccag   16380
gcccacaggt gagtgatgca cttttgccccg tctgccaagt ccccatctta ccctcacctc   16440
ttatctgacc ctgttccctc caggggggacc caggtgtccg aggcccagca ggagaaaagg   16500
tgagagggtg tgggggtttc tcaggacatg agcctgggtt atcagatcca cctcagcctt   16560
ggtggcctct taccactcta ttttccacag ggtgaccggg gtcccctgg gctggatggc    16620
cggagcggac tggatgggaa accaggagcc gctgggccct ctgggccgaa tgtgagtctt   16680
ggtagtcctg cctggttgtc cccttcccct acccctttcac atgaggaccc tagaccccag   16740
cctcattggt tggtcttggc cttgacgagc tctgggcga gacctgttgt ctgtgtcttc    16800
tcccagagcc ctgcctgggt ggggcatgtt cttgccatgc aggccttagg ctcacaggga   16860
ctagagcccc tgaccccatg accatgatga actgactttg agtctctcct cagggtgctg   16920
caggcaaagc tggggaccca gggagagacg taagtgaggg gagatgctgg gacagagggg   16980
gctcggggct gcgtaagctc caaccagatc atcatagtca cagcatccga gagagttggt   17040
gggggggtcgg ttcagccttg cctttgggag ggtctcagtc cctggcacac aggttttagt   17100
agaatccccc tttctgacct tctttgcctt ggggggtcttc ataggccctc caagtcctgg   17160
gggttcttcc cttgggagtc tcagcagggg ccccccatcca tggggtctgt gcctgaggga   17220
tctcaatggg acctctcagt cctggggggtc tctaccctgg agggagatct ttttgggggtc   17280
ctcttagtcc atggggtgtg ccccaaggga tatctcagag gccctataaa tcttaacaaa   17340
gacttttttcc aggggcttcc aggcctccgt ggagaacagg gcctccctgg ccctctggt   17400
cccctggat taccggtgag accagacttt catgttaccc ccttttcccc cttactaccc    17460
tcacccgatc cccgacatcc aaccagtgat ctgttcccac agggaaagcc aggcgaggat   17520
ggcaaacctg gcctgaatgg aaaaaacgtg agtgtgtcca gggcagctgc ggcgaaacct   17580
gccaagaaac gccagcacac ctacacagcc aagatctgta gcaacacatg aggcacacgt   17640
gtagacacat gcatcctggc ccagacatac agatgcatcc agaaacatag ttttttttttt   17700
tttgagatgg agtttcgctc ttgttgccca ggttggagtg cagtggcaca atctcagctc    17760
actgcaacct tcgactctcg ggttcaagtg attctcctgc ctcaacctcc cgagtaactg   17820
ggattacagg catgcgccac catgcctggc taattttgta ttttttagtag agatgggggtt   17880
tctccatgtt agtcaggctg atcacaaact gacctcaggt gatccgcccg cctcggcctc   17940
ctaaagtgct gggattacag gcgtgagcca ttgcgccagg cctggaaaca tagttctata   18000
tgcacacaca ggcagcctca cagacacata gggagttagg tgaatgggcc aatttatgcc   18060
aggatgggct gacacatgcc cagataaccc acagccatag gcacaggtga agagccacag   18120
acaggtcgac aggcacaaac acactggtgt gtagccacat ttggggcact tagagacatg   18180
ttgatacccca gacacttcca cccagactca tgtgctaaga catggaccca agaccgcatg   18240
tggacctgtg ttgagacatg gtgagacaca catggatggc tctgacctgt gacatgtgct   18300
aggacatgct ggcccatgac tttatatggt cacccacacg cttatggtca tacacattga   18360
gctacacaca agagttgcag acagatgcca agacacatgg ctctcaaggc atgtataagc   18420
ccatgctctt tggagacatg tataagccca tgcccatatg cagacatggg ccaagatgtg   18480
caaacagacc aggacacaca gacccatggg tacatgtact aagacacaca tggatatgca   18540
cacccccagg acatgtggac gatcaccaac ccagagatgc ataaatgtgg agctacctct   18600
agagagccag agtcaaagga catgtgtgca gttgcctgtt ggggtgagca ggcctatgca   18660
```

```
ggcacaccct tagacatgta gcagctcact cagacggcca caggccatgc tccaagacac    18720
acacaaccat ggagctacag gcacagaaat acagtcacag tcatctgaaa tctagcaagg    18780
tagtgtcttg cagccagaca ccagtgaatg tttgggctga tgtgagtcct ctgcccacag    18840
ggagaacctg ggaccctgg agaagacggg aggaaggtaa agtcccccac ctggggtctc     18900
tctggtctct gcttggagcc atgcctgaag catccttgtc ttccttaggg agagaaagga    18960
gattcaggcg cctctgggag agaagtgagt attggagttt tctgcaacct ctgacccctg    19020
accctgaccc tgggggaata tgactccact cttttctgag gtctcagggt gctgatgctg    19080
gctgcatcct tcacagggtc gtgatggccc aagggtgag cgtggagctc ctggtatcct     19140
tggaccccag gggcctccag gcctcccagg gccagtgggc cctcctggcc aggtgagtgt    19200
cctgggtcat tctgggactt cagagcatta aagccatga tgtttcaatg ggcaaccctc     19260
ctgggaagcc atgggccttt tgtgaccct tgtgttctgc cgtatctcag ggttttcctg     19320
gtgtcccagg aggcacgggc ccaaggtga gtgcggatgt tgggtagggg gcgtggtgag     19380
ggggctgacc aggctggggg ccatttcccc acctggtcat tcttgttttc agggtgaccg    19440
tggggagact ggatccaaag gggagcaggt gaggccccca cctttccac atgcccaggt     19500 agccacagca cccacatgtg cacatgcaca cccataggct ggttcctagc agtttgtctt    19560
catctctcca gggcctccct ggagagcgtg gcctgcgagg agagcctgga agtgtgccgg    19620
tgagccaggc ttgggatgtc cccttgactc tgttttgcat gcccattggg gccaccttgc    19680 catcccttc cccttgccat gaggctccat aggttctgtg ctgtgtgttc agtgccctgc     19740
cccattgggg ttcttgtagc ccacactcaa gggaacttgg gcagtgggga cacaccagaa    19800
aggggctccc aggagtctcc agccatgcct caaccaagtg ctaaagggtg ctctgggcaa    19860
gaggcctagg gaaagggtg tgaaggtgct ttcctgaggc cgtgcgggc agaaggcagg      19920 agcttctctg tcatgggcag cccttcaccc agactttgtc cccagaatgt ggatcggttg    19980
ctggaaactg ctggcatcaa ggtgggttgt ttaggggctg ggggtaggga caagtggggg    20040
cccttggggc tagtggtgcc cacaggcata ggggctgcgg cgacgcaccc cgctcctctg    20100
acctcttgct gtccctcagg catctgccct gcgggagatc gtggagacct gggatgagag    20160
ctctggtagc ttcctgcctg tgcccgaacg gcgtcgaggc cccaaggggg actcaggcga    20220
acagggcccc ccaggcaagg aggtgagcag aagtggctca gtgggttgtg ccccgtggag    20280
tggggtgtag ctgtacagcc accagcattc tctcttccac tcctgcaggg ccccatcggc    20340
tttcctggag aacgcgggct gaagggcgac cgtggagacc ctggccctca ggggccacct    20400
ggtctggccc ttggggagag gggcccccc gggccttccg gccttgccgg ggagcctgga    20460
aagcctggta ttcccgggct ccaggcagg gctgggggtg tgggagaggc aggaaggcca    20520
ggagagaggg tgaggctggg ggctggccag gagagtgagg gaagaggggt tgggaggggt    20580
gggacccccc atgggcttgg ccctcacccg ctatttgcat tcagggaga acggggagag    20640 aaaggagaac gtggagaaca ggtgggctgc gatgggcttc gtggggcagg ctgtctggag    20700
gctgtgctgg ggctgccacc ccatttttctt gtttcctgca gggcagagat ggccctcctg    20760
gactccctgg aaccctggg ccccccggac cccctggccc caaggtgatc acccccatccc    20820 tgccttagtc ctgtgactag tgaccaggaa gccacccctta gcttggtccc cagaaatatg    20880
gtagtgtgtg ccataaccct ggaatttctg accctataac cctctgtgat cctgagatct    20940
gtgatgactc cccatgcct ctatgacaga gacatctctc cctgtgacc ttgtgtttgt      21000 aggtgtctgt ggatgagcca ggtcctggac tctctggaga acagggaccc cctggactca    21060
```

```
agggtgctaa ggtcagtgtg tggaatcagc tcggggccac cctctgccat ggcactaggg    21120
actgacttga catctcatcc ccacaggggg agccgggcag caatggtgac caaggtccca    21180
aaggagacag ggtgaggcct ctctccaccc ttccatagag tccccctcct ttctgggggc    21240
acactagagg tggtgtgcat atgcacctgg gcacgtggca gggactgggg gctcagggca    21300
cgacactctg ccttcagggt gtgccaggca tcaaaggaga ccggggagag cctggaccga    21360
ggggtcagga cggcaacccg gtaagtcctt gcccaacagc cacacatgtg caagaaggtg    21420
gctctcacat gtattgtcct gtgtgcaggg ctggggtctg tactgcctgg gactgtctgg    21480
gtcctgactc tgtctagggg gatggtgggt ggagggaag ttggaactgg gaaactaagg    21540
ccttaaacct attctctgca gggtctacca ggagagcgtg gtatggctgg gcctgaaggg    21600
aagccggtga gtggtggctg aagcacctgg ccccaggctc cggaccctcc gctaggtgct    21660
gctgctgctg tgtgtgtgca tgtctgtgtg tgtgtgtttg tgtgtacctg tgtctgtgtg    21720
cctctctgtg tgtgcctgct tgtgtgtgcc tgtgtctgtg tgtgcctgtg tgtgcctgtg    21780
tctgtgtgtg gttgtatgtg gatgtgtgtg tgcaggcccg tgtgtgctat ctatgagagg    21840
cagtccatgg gtaggtatta tctgtgactg gaaagggtga ggtatggaaa ttgaccccca    21900
aggaaaaagc ccccagaggt tgggaacagg cccaagtgag gcccagattg aggctcatca    21960
gtgccctctc tatgtagggt ctgcagggtc caagaggccc ccctggccca gtggtgagta    22020
cccaagaacc ttcacctgtc ttgccccat cctgtgccct gccccagtga ccagtactgc    22080
ctcagtttcc ttggtggggt gcggctaact ccccctcatc agactctttt tcgccacaac    22140
agggtggtca tggagaccct ggaccactg gtgccccggt gagtgaccag gaacactgc    22200 ctggtgaggg tctggaaggg ctgggatagg cattggccac agctgatgag ccaggccttc    22260
tctgtgttaa tccctgagcc ctgttccctg cccttgaccc ttttctctag ggtcttgctg    22320
gccctgcagg accccaagga ccttctggcc tgaaggtgag tctaggtgtg tggataggag    22380
gaggaggctc cttcaagctg tgtccatgcc tggggtagtg tgcgccaacc tcctgggctg    22440
tcatctcctg caatgaggat gagctccagg agccctggcc acgtgggctc tgctcatgca    22500
gtctctgggt tgtttgcagg gggagcctgg agagacagga cctccaggac gggtgagtgg    22560
cctagctcac aggttagggt catagggaga tgggtggggt tggcactgcc ctgaactttc    22620
tcttcctcca gggcctgact ggacctactg gagctgtggg acttcctgga ccccccggcc    22680
cttcaggcct tgtggtgagt gagtccctgt ggcccctgta gggacaccgt gttttcactc    22740
cttggggccc atgttctctc atgtcgtcct gtgtccattg tcaccctgac atccgacttg    22800
ttctccgtca gggtccacag gggtctccag gtttgcctgg acaagtggtg agttctgggg    22860
gtcaagggtt gggctccagg ggtcaagggt cgacaggcag ccctgacaga gctcttccct    22920
ctcaggggga gacagggaag ccgggagccc caggtcgaga tggtgccagt ggaaaagatg    22980
gagacagagg gagccctggt gtgccagtat gtgttctggg ggcagctcgc tagggtgtgg    23040
tgcccagctg tgggcctgaa atatgaggag tggggcagca ggggtggtgg tggagaggca    23100
ctgagttcct cacgctgctc tgccataggg gtcaccaggt ctgcctggcc ctgtcggacc    23160
taaaggagaa cctggcccca cggggcccc tggacaggta atctttgacc ctgacttcca    23220 cccccctgcag caactcctct gcctcaccca caagcctgtt tccaaatgcc atggggtgg    23280 cagggtgggg gcggggaggg aggaggaaac tcactagcat tccccacagg ctgtggtcgg    23340
gctccctgga gcaaagggag agaaggtgag tgtgtgtggg gctgccagtg agggggggtc    23400
aactggtggg ggccaaggaa tcccactgac ctctcccct taccagggag cccctggagg    23460
```

```
ccttgctgga gacctggtgg gtgagccggt aagtagggaa cttctgacag cagatgttct    23520
gggggtcctg tctctccagt ggcctaactt ctgaccttcg acccatagtt tacccaccct    23580
catgaccctc agctttcata gtagaccgca tatttaagct ctggcccat gcctccctcc     23640 ggagtctcat ctttctgtga ctgatgcctg tgttgcctcc tgacctctgt caacagggag    23700
ccaaaggtga ccgaggactg ccagggccgc gaggcgagaa ggtgaggtgg gttggccctg    23760
gggcctgact actgagcaga gaaggctcag tccagacacc cctcacctgc cattctgtgc    23820
agggtgaagc tggccgtgca ggggagcccg gagaccctgg ggaagatgtg agtccggggc    23880
ctaggcaagg gcgagcctgg cctgaggagt gtgatggcgg gcataagggg ccactcttgg    23940
gccggggcac atgtctgagc ccctgagtcg ggctgcatgt cccaacatcc aggagcctgc    24000
tctctggatc acagggagcc acacactgtc ggcttccaca ctctgagctc tgggggccct    24060
gtcttggctt ctgtgtgccc atccttggtc tgtttctcac cacatctggg cacacgtgtg    24120
ctctggtctg atctcccaga tcccaggaca cacctgagtt cttgtgaacc tctccttggt    24180
cctgtgttta caatcctcct ttcccctgcc cctggctgcc agcgttcagc ctgtggccat    24240
gcctgctcta cccgggagtg gacgtgttgg ggttcccctc tgagcgcccg tgtgtccgca    24300
ctcacgtctg tggagccaga tgtctgcact cgcgtgtggg ctccctgtgc ctgtgccatg    24360
cctgaactcc cacctgtcta tggtagtatc tgagcgtccc tctgtctgtg ctgtcctgag    24420
ataggccatg tcatgtctg agctcctgtg agccaattct tggtcgcatg tctgagttcc    24480
catgtgttca tggtcacatc agaactcccc tgggaatatt ttcagcccgt gtctgaactc    24540
tgtgctcatg ttcctaccct ctcaaatgct gtttgctggg ttttcttagg gtcagaaagg    24600
ggctccagga cccaaaggtt tcaaggtatg tgtacccaga agggtccctg ctggggtcct    24660
ggtcgtgaga ctccctgagc ttgatccgat gcctctttc ctcaaagggt gacccaggag    24720
tcggggtccc gggctcccct gggcctcctg gccctccagg tgtgaaggta agtcaatgcc    24780
ccatcaccag ttgtagggc agcaggccgg gcccccacag gaggaagagg gagttctgat    24840
gagagtcctg ggaggggtcc tgcattgacc attccctccc tttgctgttt ttatttcagg    24900
gagatctggg cctccctggc ctgcccgtg ctcctggtgt tgttggggttc ccgggtcaga    24960 caggccctcg aggagagatg ggtcagccag gccctagtgg agagcgggtg aggggctggg    25020
aacagcatgt aggggcatgg tgaatccatg gtgggtgagg aggggggccct gccttggggg    25080 ttcccagtct tgaggggggca gagggtagga gggttcccaa gtcactctct gcctctcttg    25140
ccccattttt ctggtagggt ctggcaggcc cccagggag agaaggaatc ccaggacccc     25200
tggggccacc tggaccaccg gggtcagtgg tgagtagagg tgccctaaag ccccacgtat    25260
ttgatttcct gtcctcgtga ggacttagga tgggcgggc cacactgtgg ggtgttgggg     25320
gaggcgcttt gagagccaca ggaccctcac ctcactctga cctacaggga ccacctgggg    25380
cctctggact caaaggagac aaggtaggtg ggacaagtgc tgctgactct ctcttgtgcc    25440
ctggtcaccc ccttcagcct ccactgacct cccatgaccc tgcgtccccc actgattccc    25500
ctcactgatc cccggtgtcc tgttggtctc cagggagacc ctggagtagg gctgcctggg    25560
ccccgaggcg agcgtgggga gccaggcatc cgggtacgta tgtcttactc cacagccgaa    25620
ctcccttcat cccagctctt gcctctgatt tccaacctct gagtcaatga acctaatgtc    25680
accatccagg gtgaagatgg ccgcccggc caggagggac cccgaggact cacggtgggt    25740
cccgctgggg aaagtgacag tgctgtgact tcagtcccct gcctgtgccc tttgtacccc    25800
aggactctct gccatcctcc ctagccctct ggccctcctc gtctaccct gtcccctttg     25860
```

```
tctggtcccc actgtttccc tcctcccccct gatcctcctc cgtcctccac tgccctggtt    25920
cctgtagctc acggtcacct tctctcacac aggggccccc tggcagcagg ggagagcgtg    25980
gggagaaggt aggaacgtgg ggaaggtcct ggcatgagtg gggggggtgag tggatcttgt    26040 atgatattag aattcaggtg cggggcctcc ccagtttggg cgggactcac actcttttgc    26100
ccaatagggt gatgttggga gtgcaggact aaagggtgac aaggtgagtg tgggcatggg    26160
gagggcaggg caggggccag ggtgctcccg actcctctga ttcctgcctg cccccctcagg    26220 gagactcagc tgtgatcctg gggcctccag gcccacgggg tgccaagggg gacatggtga    26280
gtgggcccac gtgtggactg ggtctcccct gggtgcgaga gggacccccgt ggggctggcc    26340 cagggcatct gagagctcaa actcccagag ggtgagggac cttcagcccc ttaccgtgac    26400
ttcttaccca aaccaaccca gggtgaacga gggcctcggg gcttggatgg tgacaaagga    26460
cctcggggag acaatgggga ccctggtgac aaggtacagg gaagagggtg gtgtactctc    26520
tgtggggtcc tgtggctgtg gtggttccac agcatctgtg agggcaggag gggaggacag    26580
gaggaggctt tctggggttt aggggaaggg ggttctgtgg ctgactatgg agtggccgag    26640
aggaggggct ctaggagggg ctcaaggcct tggtgtgagg ttaggagagc tctgtggact    26700
ggccctatga aggggcccta tagggacagg aaaggggctc cttgggtgtc cccatctgaa    26760
ggtgcttcag atgggatgag gaacccagtg ataagagggc ggggcaaggg tctggagtcc    26820
ttggggtgag aaatgagcca gtctgtggac tacagccccc agttccaccc gctatggcac    26880
aggctgggag gacgtgctgc tagggccgtt cgggagtgac ttgagctctg ccccagctgg    26940
cgggctcgtt gtattctaag ccccagcct gatctggtcc tgactgaatc cctctcctgg    27000
tcactcccac agggcagcaa gggagagcct ggtgacaagg gctcagccgg gttgccagga    27060
ctgcgtggac tcctgggacc ccaggcaagt tctgccccag gccaggccc aggcccaggt    27120 ccagagccag catcacacac acacatatcc tgggggtcct cttaagtgct gggggttctg    27180
gctcccttgc tgccggcccc atgtgtgttc accccggatc tgtgtgtggc ctgggccctg    27240
gccgctgagc atctgagtgg ccacacatgc agcggatggg ccagtgttgg ggacagtccc    27300
actgaagggc tcccccatct gtgtttctca cagggtcaac ctggtgcagc agggatccct    27360
ggtgacccgg taagatgccc ctgctcccac aggggccccc tgtccccaga gggcccccgt    27420
caccatggtg gtcccaccag tgtggtagct tttgacctta tagtgaccca gtgctctcat    27480
ggtgtcctca tgtcacccag ggtcccccac ctccacagta gccgcctatg atggtgtccc    27540
ctgcctatgg tgaccctgt ccccatggca agcccagtg gctctggcct ccagaggtga    27600
ctcccacccc atggtgttcc ctacccacta tccagggcga ttctctttgg tccctcactg    27660
acctcctctg acctcacatg gaccctctcc ctgctaggga tccccaggaa aggatggagt    27720
gcctggtatc cgaggagaaa aaggagatgt tggcttcatg ggtccccggg gcctcaaggt    27780
aggaaagaaa caagattggt tttttttctgg tcaggaaggc ctaatgttga agggcgaggg    27840 acctgggtc agatattagg gcactgggtc agaggttgga gtagctgagg cctgtttgga    27900
gagttagttt cagggtgaag ggggtcacag agtgaggtgt ctgggaatca cttcttcatc    27960
tgcttttctc cctcagggtg aacgggagt gaagggagcc tgtggccttg atggagaaa    28020 gggagacaag gtacagaggg gatgggggct gggggctac gtggcctggg gcctaaggct    28080
caccccactg cctgatgcct gcagggagaa gctggtcccc caggccgccc cgggctggca    28140
ggacacaaag gagagatggt gagtgtgggc acgctcagaa tgagggggcc acgggtggac    28200
gggggccaag ttcatgtctt ttttttctcca ggggagcct ggtgtgccgg gccagtcggg    28260
```

-continued

```
ggcccctggc aaggagggcc tgatcggtcc caaggtacag ggtctgtgga cagtggacat    28320
gacagggagt caggatgggg cagggaagct catggtcggg tcatgggggt gtagggacaa    28380
ggaaggctgt agagggttgg gactttgggg gctgaagtgg ggctggtctc gaggtgtcaa    28440
ggtgggttgg ggtcacagtg gagttaggat gaaagcatgg gaggtggagg gggcatgtgc    28500
atcagggcag ggggctatag tggagttgga gtcatgggga tcacatctgg ttggctcaca    28560
ggtgcttggg ttacagaagg tttgggcatt aggccaggga gctcatggga gttcagggag    28620
gttccagagc tgagggaggt cagggcagaa ggtctctcat gcttcttctg ttcccagggt    28680
gaccgaggct ttgacgggca gccaggcccc aagggtgacc agggcgagaa aggggagcgg    28740
gtgagttgaa gccatggtca tggtgaattg aggggagcgt gcactttggg agagggtcca    28800
tctctgggc ctctgattac tgactctgtc ctatatctcc ccagggaacc ccaggaattg    28860
ggggcttccc aggcccagt ggaaatgatg gctctgctgg tcccccaggg ccacctggca    28920
gtgttggtcc cagaggcccc gaaggacttc agggccagaa ggtaaggggc cccagctctg    28980
actcctgatc cctgaacctt ccctacccct ccaacctcat aaccatcttc cagcctgcct    29040
gccccaacct ctgaagctgt ggccccaac ctgcctgact ctgatcccca ctgcctctga    29100
ccctgctcac ttggtccctg tgtctgacag ggtgagcgag gtccccccgg agagagagtg    29160
gtggggctc ctgggtccc tggagctcct ggcgagagag gggagcaggt gagtagggat    29220
tccaaggctt gggtcagaga tcgggtgac ttctgttgtc cctgaggtca gaggtcacag    29280
cctggtccca tctgttgcac atagggggcgg ccagggcctg ccggtcctcg aggcgagaag    29340
ggagaagctg cactgacggt gagtgtgggc ctggatgggc ctgggagggc ctgggtgggc    29400
ctgggtgggc tggggcccta cctccctcac ccagcaccct gaccctgggg ccctggctcc    29460
atgcagtctc accatagtcc ctgtattatg tgccctatgt ccttcctgtg ggccatgggt    29520
tctttatggt ccctgtggtc ttctgctccc aggaggatga catccggggc tttgtgcgcc    29580
aagagatgag tcagcactgt ggtgagtggt gcccagcccg cagtctccca ctccacccca    29640
gcaccctagg caagggcagg caggccccta gaacttacag ggcaagcagt caagaagatg    29700
gggggatgga tggatacaca gaaggacaca tgtgctgcag gactgacaca tgacatgtgt    29760
ccccagtgga gggagacaca caggcagatg aggattgcca tgcagtgctc tcagatgtcc    29820
agcttggctg tgtggggagt gggatgatgg tgggagcaga gctggtcccc ttgggcctga    29880
cctggacccg gtgggagggg catcagagtg aagctgtctc ttcccgtctc tgtctgcacc    29940
acctgcctgt ttctgtgtct ggcctgcttc tgtctcttgc cttttgttgg cctgttccca    30000
acttccctct cctctgcctt cttctctttt tccatctctc tatctacctc ccaccctctc    30060
tcttcctctc tctcctgtta ccctctcctg ctatctcttt gtgtatctct acccctctgc    30120
ctgtgtgtct ctgtctgtct ctccatcttc ccatccttct ctctgtcatt gtctctctat    30180
ccctctctgc ccctctagc ctgccagggc cagttcatcg catctggatc acgtgagtag    30240
ttttctactc ccagaacttt cttcaccccca ggccctgccc tgcctatcaa ctgggggtcct    30300
ctcagggggg ttggctggga tggctgccca tggtgacttc agggccctga ggcccctgct    30360
cttggctcca ggacccctcc ctagttatgc tgcagacact gccggctccc agctccatgc    30420
tgtgcctgtg ctccgcgtct ctcatgcaga ggaggaaggt gaggacagct gaacccgtgg    30480
ggcagctatg ggtggggccg agacacgcac atgggtgtcc atgaatgcag ggcacacgcc    30540
aagcacgtag ggtctgcatg cagggcacac gcatgggcac tgtgtgcaca cagtggaaat    30600
cagtgctgcc caccttgccc cggggccagc agccactgct cccagcacac cctgccctac    30660
```

```
ctgcagagcg ggtaccccct gaggatgatg agtactctga atactccgag tattctgtgg   30720
aggagtacca ggaccctgaa gctccttggg atagtgatgg tgagaatggg gggctgccaa   30780
cggggtctgg ggaggggcag gcagggctga gccctgctga cctccccctg acctttcaac   30840
cctctctgat tcccacaaac cctgctgact tgacccatt ggcccagacc cctgttccct   30900
gccactggat gagggctcct gcactgccta caccctgcgc tggtaccatc gggctgtgac   30960
aggcagcaca gaggcctgtc acccttttgt ctatggtggc tgtggaggga atgccaaccg   31020
ttttgggacc cgtgaggcct cgagcgccg ctgcccaccc cgggtggtcc agagccaggg   31080
gacaggtatg ggctgagccc ccaccgtggg gaactgggca ctgagcctgc ctggatcggg   31140
ttctggggga ggagtccttg gccagggtt ccaggtcagg gtcctggagg agacgctccc   31200
tcgcagtagg ggacctgggg cagacgccca gaccaaagag ctgaatatag agccccagcc   31260
gtggagcccc cagtagggtc cccttccatg ttccctcctt taaagaccta agtatggacc   31320
cctctgaggt cagagccccc acttcctgtt gtagcctccg ctccctcccc ttggcggtgc   31380
ctctgcctga gcgtctccgg ggaaggtcag atggctgacg accgtttcca acctgtcctc   31440
accaggtact gcccaggact gaggcccaga taatgagctg agattcagca tcccctggag   31500
gagtcggggt ctcagcagaa ccccactgtc cctccccttg gtgctagagg cttgtgtgca   31560
cgtgagcgtg cgtgtgcacg tccgttattt cagtgacttg gtcccgtggg tctagccttc   31620
ccccctgtgg acaaaccccc attgtggctc ctgccaccct ggcagatgac tcactgtggg   31680
ggggtggctg tgggcagtga gcggatgtga ctggcgtctg acccgcccct tgacccaagc   31740
ctgtgatgac atggtgctga ttctgggggg cattaaagct gctgttttaa aaggctcctg   31800
ttgtgactgt ttgggaagat ggggggtttc aaggggaag gttttccttg gggggttggt   31860
attattctgc atgggtacag agtccctctg cccagtcctg gtcactgtct tgtgattctc   31920
agtccccaac ttgtccccgg aaaagagtag ataggggtgg ggctaaggac accccgggga   31980
gggatgagtc ataggtgggg ggctgcctca tgccaggaag catgtaccag ctcccaccc   32040 aggggggctga gggagataaa tgggccctga agcggggtag agggtcagac cacaggacag   32100
tagtgcctgg ccccagcccc aggcagccac agcaggctgc cttaccccag aagcagctgg   32160
tggcggtagg actgggttgg gtcgggatgg gaagggtctt ggaggttgag tggatgtggg   32220
gtttggcttt atggagggct tggacccagg ggactctggg atctctggct gcttttctgc   32280
ctctgagatc cgattcctgc ccttctgttt cctggatcag ctgcaagctc tcctgctgag   32340
aaccgcctgc cctcctgtgg actctgtgtt tctgtctgaa tctttctttc catca         32395
```

<210> SEQ ID NO 33
<211> LENGTH: 54
<212> TYPE: DNA
<213> ORGANISM: Artificial Sequence
<220> FEATURE:
<223> OTHER INFORMATION: Primer

<400> SEQUENCE: 33
gccagtgtcc tcactgtccg ccggggtgag tactgcagga ggcttgtgga ggac         54

<210> SEQ ID NO 34
<211> LENGTH: 54
<212> TYPE: DNA
<213> ORGANISM: Artificial Sequence
<220> FEATURE:
<223> OTHER INFORMATION: Primer

```
<400> SEQUENCE: 34
cggtcacagg agtgacaggc ggccccactc atgacgtcct ccgaacacct cctg      54

<210> SEQ ID NO 35
<211> LENGTH: 54
<212> TYPE: DNA
<213> ORGANISM: Artificial Sequence
<220> FEATURE:
<223> OTHER INFORMATION: Primer

<400> SEQUENCE: 35
gccagtgtcc tcactgtccg ccggggtgag tactgcagga ggcttgtgga ggac      54

<210> SEQ ID NO 36
<211> LENGTH: 54
<212> TYPE: DNA
<213> ORGANISM: Artificial Sequence
<220> FEATURE:
<223> OTHER INFORMATION: Primer

<400> SEQUENCE: 36
cggtcacagg agtgacaggc ggccccactc atgacgtcct ccgaacacct cctg      54

<210> SEQ ID NO 37
<211> LENGTH: 54
<212> TYPE: DNA
<213> ORGANISM: Artificial Sequence
<220> FEATURE:
<223> OTHER INFORMATION: Primer

<400> SEQUENCE: 37
gccagtgtcc tcactgtccg ccggggtgag tactgcagga ggcttgtgga ggac      54

<210> SEQ ID NO 38
<211> LENGTH: 53
<212> TYPE: DNA
<213> ORGANISM: Artificial Sequence
<220> FEATURE:
<223> OTHER INFORMATION: Primer

<400> SEQUENCE: 38
gccagtgtcc tcactgtccg ccgtgagtac tggcaggaag gcttgtggag gac       53

<210> SEQ ID NO 39
<211> LENGTH: 47
<212> TYPE: DNA
<213> ORGANISM: Artificial Sequence
<220> FEATURE:
<223> OTHER INFORMATION: Primer

<400> SEQUENCE: 39
gccagtgtcc tcactgtccg ccggactgca ggaggcttgt ggaggac               47

<210> SEQ ID NO 40
<211> LENGTH: 46
<212> TYPE: DNA
<213> ORGANISM: Artificial Sequence
<220> FEATURE:
<223> OTHER INFORMATION: Primer

<400> SEQUENCE: 40
gccagtgtcc tcactgtccg ccgggtgcag gaggcttgtg gaggac                46
```

```
<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
gccagtgtcc tcactgtccg ccggggtgag tactggagga c         41

<210> SEQ ID NO 42
<211> LENGTH: 39
<212> TYPE: DNA
<213> ORGANISM: Artificial Sequence
<220> FEATURE:
<223> OTHER INFORMATION: Primer

<400> SEQUENCE: 42
gccagtgtcc tcactgagtg caggaggctt gtggaggac            39

<210> SEQ ID NO 43
<211> LENGTH: 38
<212> TYPE: DNA
<213> ORGANISM: Artificial Sequence
<220> FEATURE:
<223> OTHER INFORMATION: Primer

<400> SEQUENCE: 43
gccagtgtcc tcaccgtagc aggaggcttg tggaggac             38

<210> SEQ ID NO 44
<211> LENGTH: 38
<212> TYPE: DNA
<213> ORGANISM: Artificial Sequence
<220> FEATURE:
<223> OTHER INFORMATION: Primer

<400> SEQUENCE: 44
gccagtgtcc tcactgcagg aggagccttg tggaggac             38

<210> SEQ ID NO 45
<211> LENGTH: 32
<212> TYPE: DNA
<213> ORGANISM: Artificial Sequence
<220> FEATURE:
<223> OTHER INFORMATION: Primer

<400> SEQUENCE: 45
gccagtgtcc tcactgtcct gacttggagg ac                   32

<210> SEQ ID NO 46
<211> LENGTH: 33
<212> TYPE: DNA
<213> ORGANISM: Artificial Sequence
<220> FEATURE:
<223> OTHER INFORMATION: Primer

<400> SEQUENCE: 46
gccagtgtcc tcactgtccg ccgtgaggac agc                  33

<210> SEQ ID NO 47
<211> LENGTH: 24
<212> TYPE: DNA
<213> ORGANISM: Artificial Sequence
<220> FEATURE:
<223> OTHER INFORMATION: Primer
```

<400> SEQUENCE: 47
gtacgcagga ggcttgtgga ggac                                              24

<210> SEQ ID NO 48
<211> LENGTH: 16
<212> TYPE: DNA
<213> ORGANISM: Artificial Sequence
<220> FEATURE:
<223> OTHER INFORMATION: Primer

<400> SEQUENCE: 48
gaggcttgtg gaggac                                                        16

<210> SEQ ID NO 49
<211> LENGTH: 12
<212> TYPE: DNA
<213> ORGANISM: Artificial Sequence
<220> FEATURE:
<223> OTHER INFORMATION: Primer

<400> SEQUENCE: 49
gggcccggga cc                                                            12

<210> SEQ ID NO 50
<211> LENGTH: 10
<212> TYPE: DNA
<213> ORGANISM: Artificial Sequence
<220> FEATURE:
<223> OTHER INFORMATION: Primer

<400> SEQUENCE: 50
gagggccctg                                                               10

<210> SEQ ID NO 51
<211> LENGTH: 10
<212> TYPE: DNA
<213> ORGANISM: Artificial Sequence
<220> FEATURE:
<223> OTHER INFORMATION: Primer

<400> SEQUENCE: 51
gagggacctg                                                               10

<210> SEQ ID NO 52
<211> LENGTH: 37
<212> TYPE: DNA
<213> ORGANISM: Artificial Sequence
<220> FEATURE:
<223> OTHER INFORMATION: Primer

<400> SEQUENCE: 52
tggcccttct cactctgcgt ccctgtccat cactgcc                                 37

<210> SEQ ID NO 53
<211> LENGTH: 12
<212> TYPE: DNA
<213> ORGANISM: Artificial Sequence
<220> FEATURE:
<223> OTHER INFORMATION: Primer

<400> SEQUENCE: 53
gggcccggga cc                                                            12

```
<210> SEQ ID NO 54
<211> LENGTH: 60
<212> TYPE: DNA
<213> ORGANISM: Artificial Sequence
<220> FEATURE:
<223> OTHER INFORMATION: Primer

<400> SEQUENCE: 54
gggtggagag aaccctggtg cttcctggga gccagacggc attcgacttg gatgacgttc    60

<210> SEQ ID NO 55
<211> LENGTH: 60
<212> TYPE: DNA
<213> ORGANISM: Artificial Sequence
<220> FEATURE:
<223> OTHER INFORMATION: Primer

<400> SEQUENCE: 55
gggtggagag aaccctggtg cttcctggga gccagacggc attcgacttg gatgacgttc    60

<210> SEQ ID NO 56
<211> LENGTH: 60
<212> TYPE: DNA
<213> ORGANISM: Artificial Sequence
<220> FEATURE:
<223> OTHER INFORMATION: Primer

<400> SEQUENCE: 56
actccacttg ctgttccagg gctgcgggtt gtggtgtcag atgcaacgcg agtgagggtg    60

<210> SEQ ID NO 57
<211> LENGTH: 60
<212> TYPE: DNA
<213> ORGANISM: Artificial Sequence
<220> FEATURE:
<223> OTHER INFORMATION: Primer

<400> SEQUENCE: 57
actccacttg ctgttccagg gctgcgggtt gtggtgtcag atgcaacgtg agtgagggtg    60

<210> SEQ ID NO 58
<211> LENGTH: 39
<212> TYPE: DNA
<213> ORGANISM: Artificial Sequence
<220> FEATURE:
<223> OTHER INFORMATION: Primer

<400> SEQUENCE: 58
gtggctgtgt cggtactgcg aggcagagag gagggacct                           39

<210> SEQ ID NO 59
<211> LENGTH: 39
<212> TYPE: DNA
<213> ORGANISM: Artificial Sequence
<220> FEATURE:
<223> OTHER INFORMATION: Primer

<400> SEQUENCE: 59
gtggctgtgt cggtactgcg aggcagagag gagggccct                           39

<210> SEQ ID NO 60
<211> LENGTH: 54
<212> TYPE: DNA
<213> ORGANISM: Artificial Sequence
<220> FEATURE:
<223> OTHER INFORMATION: Primer
```

-continued

<400> SEQUENCE: 60
gccagtgtcc tcactgtccg ccggggtgag tactgcagga ggcttgtgga ggac    54

<210> SEQ ID NO 61
<211> LENGTH: 240
<212> TYPE: DNA
<213> ORGANISM: Artificial Sequence
<220> FEATURE:
<223> OTHER INFORMATION: Primer

<400> SEQUENCE: 61
tcgacttgga tgacgttcag ctgggctta gctacactgt gcgggtgtct gctcgagtgg    60
gtccccgtga gggcagtgcc agtgtcctca ctgtccgccg ggagccggaa actccacttg   120
ctgttccagg gctgcgggtt gtggtgtcag atgcaacgcg agtgagggtg gcctggggac   180
cctaccaggt ggctgtgtcg gtactgcgag gcagagagga gggacctgct gcagtcatcg   240

<210> SEQ ID NO 62
<211> LENGTH: 213
<212> TYPE: DNA
<213> ORGANISM: Artificial Sequence
<220> FEATURE:
<223> OTHER INFORMATION: Primer

<400> SEQUENCE: 62
tcgacttgga tgacgttcag ctgggctta gctacactgt gcgggtgtct gctcgagtgg    60
gtccccgtga gggcagtgcc agtgtcctca ctgtccgccg ggggctgcgg gttgtggtgt   120
cagatgcaac gcgagtgagg gtggcctggg gaccctacca ggtggctgtg tcggtactgc   180
gaggcagaga ggagggacct gctgcagtca tcg                              213

<210> SEQ ID NO 63
<211> LENGTH: 12
<212> TYPE: DNA
<213> ORGANISM: Artificial Sequence
<220> FEATURE:
<223> OTHER INFORMATION: Primer

<400> SEQUENCE: 63
gggcccggga cc    12

<210> SEQ ID NO 64
<211> LENGTH: 12
<212> TYPE: DNA
<213> ORGANISM: Artificial Sequence
<220> FEATURE:
<223> OTHER INFORMATION: Primer

<400> SEQUENCE: 64
caacgcgagt ga    12

<210> SEQ ID NO 65
<211> LENGTH: 12
<212> TYPE: DNA
<213> ORGANISM: Artificial Sequence
<220> FEATURE:
<223> OTHER INFORMATION: Primer

<400> SEQUENCE: 65
caacgtgagt ga    12

<210> SEQ ID NO 66
<211> LENGTH: 12
<212> TYPE: DNA
<213> ORGANISM: Artificial Sequence
<220> FEATURE:
<223> OTHER INFORMATION: Primer

<400> SEQUENCE: 66

```
caacgcgagt ga                                                         12
```

<210> SEQ ID NO 67
<211> LENGTH: 227
<212> TYPE: DNA
<213> ORGANISM: Artificial Sequence
<220> FEATURE:
<223> OTHER INFORMATION: Primer

<400> SEQUENCE: 67

```
gtgtcagatg caacgcgagt gagggtggcc tggggacccg tccctggagc cagtggattt     60
cggattagct ggagcacagg cagtggtccg gagtccagcc agacactgcc cccagactct    120
actgccacag acatcacagg gctgcagcct ggaaccacct accaggtggc tgtgtcggta    180
ctgcgaggca gagaggaggg acctgctgca gtcatcgtgg ctcgaac                  227
```

<210> SEQ ID NO 68
<211> LENGTH: 227
<212> TYPE: DNA
<213> ORGANISM: Artificial Sequence
<220> FEATURE:
<223> OTHER INFORMATION: Primer

<400> SEQUENCE: 68

```
gtgtcagatg caacgcgagt gagggtggcc tggggacccg tccctggagc cagtggattt     60
cggattagct ggagcacagg cagtggtccg gagtccagcc agacactgcc cccagactct    120
actgccacag acatcacagg gctgcagcct ggaaccacct accaggtggc tgtgtcggta    180
ctgcgaggca gagaggaggg acctgctgca gtcatcgtgg ctcgaac                  227
```

<210> SEQ ID NO 69
<211> LENGTH: 228
<212> TYPE: DNA
<213> ORGANISM: Artificial Sequence
<220> FEATURE:
<223> OTHER INFORMATION: Primer

<400> SEQUENCE: 69

```
gtgtcagatg caacgcgaag tgagggtggc ctggggaccc gtccctggag ccagtggatt     60
tcggattagc tggagcacag gcagtggtcc ggagtccagc cagacactgc ccccagactc    120
tactgccaca gacatcacag ggctgcagcc tggaaccacc taccaggtgg ctgtgtcggt    180
actgcgaggc agagaggagg gacctgctgc agtcatcgtg gctcgaac                 228
```

<210> SEQ ID NO 70
<211> LENGTH: 228
<212> TYPE: DNA
<213> ORGANISM: Artificial Sequence
<220> FEATURE:
<223> OTHER INFORMATION: Primer

<400> SEQUENCE: 70

```
gtgtcagatg caacgcgaag tgagggtggc ctggggaccc gtccctggag ccagtggatt     60
tcggattagc tggagcacag gcagtggtcc ggagtccagc cagacactgc ccccagactc    120
```

```
tactgccaca gacatcacag ggctgcagcc tggaaccacc taccaggtgg ctgtgtcggt    180
actgcgaggc agagaggagg gacctgctgc agtcatcgtg gctcgaac                228
```

```
<210> SEQ ID NO 71
<211> LENGTH: 31
<212> TYPE: DNA
<213> ORGANISM: Artificial Sequence
<220> FEATURE:
<223> OTHER INFORMATION: Primer

<400> SEQUENCE: 71
agtactcagg aggcttgtgg aggacagctg c                                   31

<210> SEQ ID NO 72
<211> LENGTH: 33
<212> TYPE: DNA
<213> ORGANISM: Artificial Sequence
<220> FEATURE:
<223> OTHER INFORMATION: Primer

<400> SEQUENCE: 72
gatgccgccc caccccgcac ctcagccttc tca                                 33

<210> SEQ ID NO 73
<211> LENGTH: 31
<212> TYPE: DNA
<213> ORGANISM: Artificial Sequence
<220> FEATURE:
<223> OTHER INFORMATION: Primer

<400> SEQUENCE: 73
gtgcagggta atgggagggc tttgcaccac g                                   31

<210> SEQ ID NO 74
<211> LENGTH: 34
<212> TYPE: DNA
<213> ORGANISM: Artificial Sequence
<220> FEATURE:
<223> OTHER INFORMATION: Primer

<400> SEQUENCE: 74
ccagatttca cctttttaacc ttggtgctat atag                               34

<210> SEQ ID NO 75
<211> LENGTH: 33
<212> TYPE: DNA
<213> ORGANISM: Artificial Sequence
<220> FEATURE:
<223> OTHER INFORMATION: Primer

<400> SEQUENCE: 75
caccttggga gttaggattt taacatggat tta                                 33
```